US005759804A

United States Patent [19]
Godiska et al.

[11] Patent Number: 5,759,804
[45] Date of Patent: Jun. 2, 1998

[54] ISOLATED NUCLEIC ACID ENCODING SEVEN TRANSMEMBRANE RECEPTORS

[75] Inventors: Ronald Godiska, Bothell; Patrick W. Gray; Vicki Louise Schweickart, both of Seattle, all of Wash.

[73] Assignee: ICOS Corporation, Bothell, Wash.

[21] Appl. No.: 153,848

[22] Filed: Nov. 17, 1993

Related U.S. Application Data

[63] Continuation-in-part of Ser. No. 977,452, Nov. 17, 1992, abandoned.
[51] Int. Cl.⁶ .................. C07K 14/705; C12N 15/12; C12N 5/10
[52] U.S. Cl. .................. 435/69.1; 435/252.3; 435/370.1; 530/350; 536/23.5
[58] Field of Search .................. 435/69.1; 530/350; 536/23.5

[56] References Cited

FOREIGN PATENT DOCUMENTS

WO 92/17497  10/1992  WIPO.
WO 92/18641  10/1992  WIPO.

OTHER PUBLICATIONS

Birkenbach et al., "Epstein–Barr Virus–Induced Genes: First Lymphocyte–Specific G Protein–Coupled Peptide Receptors," *J. Virology*, 67(4):2209–2220 (Apr. 1993).

Burbach et al., "The Structure of Neuropeptide Receptors," *Eur. J. Pharm.*, 227:1–18 (1992).

Neote et al., "Molecular Cloning, Functional Expression, and Signaling Characteristics of a C–C Chemokine Receptor," *Cell*, 72:415–425 (Feb. 12, 1993).

Sasaki et al., "Cloning and Expression of a Complementary DNA Encoding a Bovine Adrenal Angiotensin II Type–1 Receptor," *Nature*, 351(6323):230–233 (May 16, 1991).

Allen et al., "G–protein–coupled receptor genes as protooncogenes: Constitutively activating mutation of the $\alpha_{1B}$–adrenergic receptor enhances mitogenesis and tumorigenicity", *Proc. Natl. Acad. Sci. USA*, 88:11354–11358 (1991).

Alper, "Oligonucleotides surge into clinical trials", *Bio/Technology*, 11:1225 (1993).

Arai et al., "Cloning and expression of a cDNA encoding an endothelin receptor", *Nature*, 348:730–732 (1990).

Benoist et al., "The ovalbumin gene –sequence of putative control regions", *Nuc. Acids. Res.*, 8:127–142 (1980).

Blin and Stafford,"A general method for isolation of high molecular weight DNA from eukaryotes", *Nucl. Acids Res.*, 3:2303–2308 (1976).

Boulay, "Synthesis and Use of a Novel N–Formyl Peptide Derivative to Isolate a Human N–Formyl Peptide Receptor cDNA", *BBRC*, 168:1103–1109 (1990).

Cherif et al., "Detection of single–copy genes by nonisotopic in situ hybridization on human chromosomes", *Hum. Genet.*, 81:358–362 (1989).

Chirgwin et al., "Isolation of Biologically Active Ribonucleic Acid from Sources Enriched in Ribonuclease", *Biochemistry*, 18:5294–5299 (1979).

Chomczynski and Sacchi, "Single–Step Method of RNA Isolation by Acid Guanidinium Thiocyanate–Phenol–Chloroform Extraction", *Analytical Biochemistry*, 162:156–159 (1986).

Cotecchia et al., "Regions of the $\alpha_1$–adrenergic receptor involved in coupling to phosphatidylinositol hydrolysis and enhanced sensitivity of biological function", *Proc. Natl. Acad. Sci. USA*, 87:2896–2900 (1990).

Crooke et al., "Therapeutic Applications of Oligonucleotides", *Bio/Technology*, 10:882–886 (1992).

Dohlman et al., "Model Systems for the Study of Seven–Transmembrane–Segment Receptors", *Ann. Rev. Biochem.*, 60:653–688 (1991).

Downes et al., "The polyphosphoinositide phosphodiesterase of erythrocyte membranes", *Biochem. J.*, 198:133–140 (1981).

Erlich, Ed., pp. 61–70 in *PCR Technology*, Stockton Press, New York, (1989).

Fan et al., "Mapping small DNA sequences by fluorescence in situ hybridization directly on banded metaphase chromosomes", *Proc. Natl. Acad. Sci. USA*, 87:6223–6227 (1990).

Findeis et al., "Targeted delivery of DNA for gene therapy via receptors", TIBTECH, 11:202–205 (1993).

Gerard and Gerard, "The chemotactic receptor for human C5a anaphylatoxin", *Nature*, 349:614–617 (1991).

Hall et al., "Linkage of Early–Onset Familial Breast Cancer to Chromosome 17q21", *Science*, 250:1684–1689 (1990).

Hirata et al., "Cloning and expression of cDNA for a human thromboxane $A_2$ receptor", *Nature*, 349:617–620 (1991).

Holmes et al., "Structure and Functional Expression of a Human Interleukin–8 Receptor", *Science*, 253:1278–1280 (1991).

Honda et al., "Cloning by functional expression of platelet–activating factor receptor from guinea–pig lung", *Nature*, 349:342–346 (1991).

Julius et al., "Ectopic Expression of the Serotonin 1c Receptor and the Triggering of Malignant Transformation", *Science*, 244:1057–1062 (1989).

Khorana, "Rhodopsin, Photoreceptor of the Rod Cell", *J. Biol. Chem.*, 267:1–4 (1992).

Kozak, "Compilation and analysis of sequences upstream from the translational start site in eukaryotic mRNAs", *Nucl. Acids. Res.*, 12:857–872 (1984).

Lefkowitz, "Turned on to ill effect", *Nature*, 365:603–604 (1993).

(List continued on next page.)

*Primary Examiner*—John Ulm
*Attorney, Agent, or Firm*—Marshall, O'Toole, Gerstein, Murray & Borun

[57] ABSTRACT

DNA sequences encoding seven novel seven transmembrane receptors and variants thereof are disclosed as well as materials and methods for production of the same by recombinant techniques. Antibody substances specific for each of the seven transmembrane receptors are disclosed as useful for the modulation of the ligand/receptor binding reactions of the receptors.

26 Claims, 2 Drawing Sheets

OTHER PUBLICATIONS

Linder et al., "G Proteins: Tucked into the internal surface of the cell's outer membrane, these versatile molecules coordinate cellular responses to a multitude of signals that impinge from without", *Sci. Am.*, 267:56–65 (1992).

Mitani et al., "Delivering therapeutic genes –matching approach and application", *TIBTECH*, 11:162–166 (1993).

Murphy et al., "Cloning of Complementary DNA Encoding a Functional Human Interleukin–8 Receptor", *Science*, 253:1280–1283 (1991).

Naylor et al., "Human Immune Interferon Gene Is Located On Chromosome 12", *J. Exp. Med.*, 57:1020–1027 (1983).

Parma et al., "Somatic mutations in the thyrotropin receptor gene cause hyperfunctioning thyroid adenomas", *Nature*, 365:649–651 (1993).

Probst et al., "Sequence Alignment of the G–Protein Coupled Receptor Superfamily", *DNA and Cell Biology*, 11(1):1–20 (1992).

Rosenthal et al., "Nephrogenic Diabetes Insipidus: A V2 Vasopressin Receptor Unable to Stimulate Adenylyl Cyclase", *J. Biol. Chem.*, 268:13030–13033 (1993).

Ruat et al., "Molecular cloning, characterization, and localization of a high–affinity serotonin receptor ($5HT_7$) activating cAMP formation", *Proc. Natl. Acad. Sci. USA* 90:8547–8551 (1993).

Sasaki et al., "Cloning and expression of a complementary DNA encoding a bovine adrenal angiotensin II type–1 receptor", *Nature*, 351:730–732 (1990).

Shenker et al., "A constitutively activating mutation of the luteinizing hormone receptor in familial male precocious puberty", *Nature*, 365:652–654 (1993).

Sikora, "Gene therapy for cancer", *TIBTECH*, 11:197–201 (1993).

Smith et al., "Single–step purification of polypeptides expressed in *Escherichia coli* as fusions with glutathione S–transferase", *Gene*, 67:31–40 (1988).

Stryer, "Visual Excitation and Recovery", *J. Biol. Chem.*, 266:10711–10714 (1991).

Thomas et al., "Molecular Cloning of the fMet–Leu–Phe Receptor from Neutrophils", *J. Biol. Chem.*, 265:20061–20064 (1990).

Vu et al., "Molecular Cloning of a Functional Thrombin Receptor Reveals a Novel Proteolytic Mechanism of Receptor Activation", *Cell*, 64:1057–1068 (1991).

Wada et al., "Codon usage tabulated from the GenBank genetic sequence data", *Nucl. Acids. Res.*, 19S:1981–1986 (1991).

ISOLATED NUCLEIC ACID ENCODING SEVEN TRANSMEMBRANE RECEPTORS

This application is a continuation-in-part of U.S. patent application Ser. No. 07/977,452 filed on Nov. 17, 1992, now abandoned.

FIELD OF THE INVENTION

The present invention relates generally to a family of cellular receptors involved in signal transduction, the seven transmembrane receptors, and more particularly to the cloning and expression of DNA sequences encoding seven novel seven transmembrane receptors.

BACKGROUND

The seven transmembrane receptors (also known as heptahelical, serpentine, or G protein-coupled receptors) comprise a superfamily of structurally related molecules. Possible relationships among seven transmembrane receptors (7TM receptors) for which amino acid sequence had previously been reported are reviewed in Probst et al., *DNA and Cell Biology*, 11 (1): 1–20 (1992). Briefly, the 7TM receptors exhibit detectable amino acid sequence similarity and all appear to share a number of structural characteristics including: an extracellular amino terminus; seven predominantly hydrophobic a-helical domains (of about 20–30 amino acids) which are believed to span the cell membrane and are referred to as transmembrane domains 1–7; approximately twenty well-conserved amino acids; and a cytoplasmic carboxy terminus. The amino acid similarity among different 7TM receptors ranges from about 10% to more than 80% and receptors which recognize similar or identical ligands generally exhibit high levels of homology. The 7TM receptors can be grouped based on their homology levels and/or the ligands they recognize. For example, the interleukin-8 receptor, the angiotensin II receptor, the thrombin receptor, the endothelin receptors, the N-formyl peptide receptor and the C5a receptor all bind peptide ligands and share 20–40% amino acid similarity.

7TM receptors recognize a great diversity of ligands (for example, light, odorants, neurotransmitters, peptide hormones and small molecules) and transduce their signals via heterotrimeric guanine nucleotide-binding proteins (G-proteins) effecting a broad array of biological activities (including visual excitation, olfactory reception, and neurotransmission) through various intracellular enzymes, ion channels and transporters. Signal transduction pathways have been elucidated for rhodopsin [Khorana, *J. Biol. Chem.*, 267: 1–4 (1992) and Stryer, *J. Biol. Chem.*, 266: 10711–10714 (1991)] and the beta-adrenergic receptors [Dohlman et al., *Ann. Rev. Biochem.*, 60: 653–688 (1991)] and are thought to illustrate the pathways utilized by other 7TM receptors. Each 7TM receptor is predicted to associate with a particular G protein at the intracellular surface of the plasma membrane. The binding of the receptor to its ligand is thought to result in activation (i.e., the exchange of GTP for GDP on the α-subunit) of the G protein which in turn stimulates specific intracellular signal-transducing enzymes and channels. Thus, the function of each 7TM receptor is to discriminate its specific ligand from the complex extracellular milieu and then to activate G proteins to produce a specific intracellular signal. Cotecchia et al., *Proc. Natl. Acad. Sci. USA*, 87: 2896–2900 (1990) reports that the intracellular loop of the third transmembrane domain of the 7TM receptors comprises important determinants for receptor coupling to specific G proteins, however, Lefkowitz, *Nature*, 265: 603–604 (1993) summarizes reports that other regions of 7TM receptors may also be essential in maintaining 7TM receptors in a constrained, inactive conformation until ligand binding occurs.

Recently, several 7TM receptors have been identified which recognize ligands important for immunological and hemostatic activities. Holmes et al., *Science*, 253: 1278–1280 (1991) describes the interleukin 8 receptor (IL8R1) as involved in neutrophil chemotaxis and Sasaki et al., *Nature*, 351: 230–233 (1991) reports the angiotensin II receptor (AT2R) is involved in vascular hemostasis. Similarly, the endothelin receptors [Arai et al., *Nature*, 348: 730–732 (1990)] regulate vasoconstriction and smooth muscle tone. The C5a receptor mediates chemotaxis, granule enzyme release and superoxide generation in vitro and appears to be involved in anaphylaxis and septic shock in vivo [Gerard and Gerard, *Nature*, 349: 614–617 (1991)]. Thrombin is also recognized by a 7TM receptor and is a potent activator of platelet aggregation, monocyte chemotaxis, lymphocyte mitogenesis and mediates inflammatory responses to vascular injury. The N-formyl peptide (f-met-leu-phe) receptor is responsible for neutrophil chemotaxis and activation [Thomas et al., *J. Biol. Chem.*, 265: 20061 (1990)]. While these 7TM receptors all have peptide ligands, other 7TM receptors that recognize small organic compounds also mediate proinflammatory activities. For example, the Platelet Activating Factor receptor recognizes a bioactive phospholipid [Honda et al., *Nature*, 349: 342–346 (1991)] which causes platelet aggregation and endotoxic shock. The thromboxane $A_2$ receptor recognizes an arachidonate metabolite which also stimulates vasoconstriction and platelet aggregation and is implicated in stroke and bronchial asthma [Hirata et al., *Nature*, 349: 617–620 (1991)].

Mutations in the third intracellular loop of one 7TM receptor (the thyrotropin receptor) and in the adjacent sixth transmembrane domain of another 7TM receptor (the luteinizing hormone receptor) have been reported to be the genetic defects responsible for an uncommon form of hyperthyroidism [Parma et al., *Nature*, 365: 649–651 (1993)] and for familial precocious puberty [Shenker et al. *Nature*, 365: 652–654 (1993)], respectively. In both cases the mutations result in constitutive activation of the 7TM receptors. Previously, other studies have shown that mutations that prevent the activation of 7TM receptors are responsible for states of hormone resistance which are responsible for diseases such as congenital nephrogenic diabetes insipidus. See Rosenthal et al., *J. Biol. Chem.*, 268: 13030–13033 (1993). Still other studies have shown that several 7TM receptors can function as protooncogenes and be activated by mutational alteration. See, for example, Allen et al., *Proc. Natl. Acad. Sci. USA*, 88: 11354–11358 (1991) which suggests that spontaneously occurring mutations in some 7TM receptors may alter the normal function of the receptors and result in uncontrolled cell growth associated with human disease states such as neoplasia and atherosclerosis. Therefore, mutations in 7TM receptors may underlie a number of human pathologies.

Because a variety of therapeutic uses may be projected for 7TM receptors involved in immunological processes in both health and disease states and because it is generally believed that numerous proteins are involved in immunological processes, there continues to exist a need in the art for the identification of additional 7TM receptors that participate in such processes and especially a need for information specifically identifying and characterizing such proteins in terms of their amino acid sequence. Isolation of DNA encoding a novel 7TM receptor also provides the basis for determination of the role of receptor in health and disease states. To the extent that such receptors might form the basis for the development of therapeutic and/or diagnostic agents, it is essential that the DNA encoding them be isolated. The isolated DNA would, for example, provide for the large scale production of the 7TM proteins, allow for the identification of cells naturally producing them, and permit the preparation/identification of antibody substances and/or other novel binding substances (including natural ligands, agonists and antagonists) which are specifically reactive with a particular 7TM receptor (or group of receptors) and which have the capacity to modulate the biological activities of the receptor(s).

SUMMARY OF THE INVENTION

The present invention provides purified and isolated polynucleotides (i.e., DNA sequences and RNA transcripts thereof) encoding seven novel 7TM receptors designated V28, V31, V112, R20, R2, R12, and RM3 as well as polypeptide variants (including fragments and analogs) thereof which possess at least one ligand/receptor binding activity or immunological property specific to one of the seven 7TM receptors. Fragments of a 7TM receptor of the invention which correspond to the N-terminal extracellular domain; the transmembrane domains; the individual extracellular and intracellular loops connecting the transmembrane domains; the C-terminal cytoplasmic domain and fusions thereof are specifically contemplated. Preferred DNA sequences of the invention include genomic and cDNA sequences as well as wholly or partially chemically synthesized DNA sequences.

Specifically illustrating polynucleotide sequences of the present invention are the DNA inserts encoding the V28, V31, V112, R2, R12 and R20 7TM receptors in plasmids which were deposited with the American Type Culture Collection (ATCC), 12301 Parklawn Drive, Rockville, Md. 20852, on Oct. 12, 1992 and were respectively assigned ATCC Accession Nos. 75330, 75327, 75326, 75329, 75331 and 75328. Also illustrating polynucleotide sequences of the invention is the DNA insert encoding the RM3 7TM receptor in a plasmid which was deposited with the ATCC on Nov. 2, 1992 and was assigned ATCC Accession No. 75340.

According to another aspect of the invention, biologically active plasmid and viral DNA vectors incorporating DNA sequences of the invention are provided as well as vectors wherein the DNA encoding a 7TM receptor or 7TM receptor variant is operatively linked to an endogenous or heterologous expression control sequence. Also provided by the invention are procaryotic or eucaryotic host cells stably transformed or transfected with a DNA sequence of the invention so that the 7TM receptor polypeptide or variant polypeptide encoded by the DNA sequence is expressed in the host cell. Host cells expressing such 7TM products can serve a variety of purposes. To the extent that the expressed products are "displayed" on host cell surfaces, the cells may constitute a valuable immunogen for the development of antibody substances specifically immunoreactive with 7TM receptors or 7TM receptor variants. Host cells of the invention are conspicuously useful in methods for the large scale production of 7TM receptors when the cells are grown in a suitable culture medium and the 7TM receptor polypeptide products are isolated from the cells or from the medium in which the cells are grown. Host cells expressing the novel 7TM receptors are also useful in assays for identifying antagonists or agonists of 7TM receptor binding.

Novel 7TM receptors of the invention may be obtained as isolates from natural cell sources, but are preferably produced by recombinant procedures involving host cells of the invention. The products may be obtained in fully or partially glycosylated, partially or wholly de-glycosylated, or non-glycosylated forms, depending on the host cell selected for recombinant production and/or post-isolation processing. 7TM receptor variants of the invention may comprise water soluble and insoluble polypeptide or peptide fragments, and may also comprise polypeptide analogs wherein one or more of the naturally specified amino acids is deleted or replaced: (1) without loss, and preferably with enhancement, of one or more biological activities or immunological characteristics specific for the 7TM receptor; or (2) with specific disablement of a particular ligand/receptor binding function. Analog polypeptides including additional amino acid (e.g., lysine) residues that facilitate multimer formation are contemplated.

Also comprehended by the present invention are antibody substances (e.g., monoclonal and polyclonal antibodies, single chain antibodies, chimeric antibodies, CDR-grafted antibodies and the like) or other binding proteins which are specifically reactive with 7TM receptor or 7TM receptor variants of the invention. Antibody substances can be developed using isolated natural or recombinant 7TM receptor products (including peptides) or cells expressing such products on their surfaces. The antibody substances are useful, in turn, in complexes for immunization to generate anti-idiotypic antibodies as well as for purifying polypeptides of the invention and for identifying cells producing the polypeptides on their surfaces. Assays for the detection and quantification of 7TM receptors on cell surfaces and in fluids such as serum may involve a single antibody substance or multiple antibody substances in a "sandwich" assay format. The antibody substances as well as agonists or antagonists of 7TM receptor binding (e.g., small molecules or peptides) are also manifestly useful in modulating (i.e., blocking, inhibiting or stimulating) ligand/receptor binding reactions of 7TM receptors of the invention, especially those reactions involved in immunological and/or inflammatory events in vivo.

The scientific value of the information contributed through the disclosures of DNA and amino acid sequences of the present invention is manifest. As one series of examples, knowledge of the sequence of a cDNA for a 7TM receptor makes possible the isolation by DNA/DNA hybridization of genomic DNA sequences encoding the 7TM receptor and specifying the 7TM receptor gene expression control regulatory sequences such as promoters, operators and the like. DNA/DNA hybridization procedures carried out with DNA sequences of the invention and under stringent conditions are likewise expected to allow the identification of DNAs encoding allelic variants of a 7TM receptor, mutant forms of a 7TM receptor associated with a particular disease state, other structurally related proteins sharing the biological and/or immunological specificity of the 7TM receptor, and non-human species proteins homologous to the 7TM receptor. DNAs of the invention are useful in DNA/RNA hybridization assays to detect the capacity of cells to synthesize a 7TM receptor.

Also made available by the provision of DNA sequences of the invention are therapeutically useful oligonucleotides (e.g., antisense oligonucleotides, oligonucleotides for triplex formation or aptamers) relevant to regulating expression of a 7TM receptor by those cells which ordinarily express the same [as is described for other oligonucleotides in Crooke et al., *BIO/TECHNOLOGY*, 10: 882–886 (1992) and in Alper, *BIO/TECHNOLOGY*, 11: 1225 (1993)]. DNA sequences of the invention may also be used in vectors which have been developed for gene therapy such as those described in Mitani et al., *TIBTECH*, 11: 162–166 (1993) (delivering therapeutic genes); Sikora, *TIBTECH*, 11: 197–201 (1993) (gene therapy for cancer); and Findeis et al., *TIBTECH*, 11: 202–205 (1993) (gene therapy via receptors).

Numerous aspects and advantages of the present invention will be apparent upon consideration of the following drawings and detailed description.

BRIEF DESCRIPTION OF THE DRAWING

The FIGURE is a schematic illustration of a possible conformation of the V31 7TM receptor in a cell membrane wherein transmembrane domain 1 is between points A and B, transmembrane domain 2 is between points C and D, transmembrane domain 3 is between points E and F, transmembrane domain 4 is between points G and H, transmembrane domain 5 is between points I and J, transmembrane domain 6 is between points K and L, and transmembrane domain 7 is between points M and N.

DETAILED DESCRIPTION

Figure 1A:
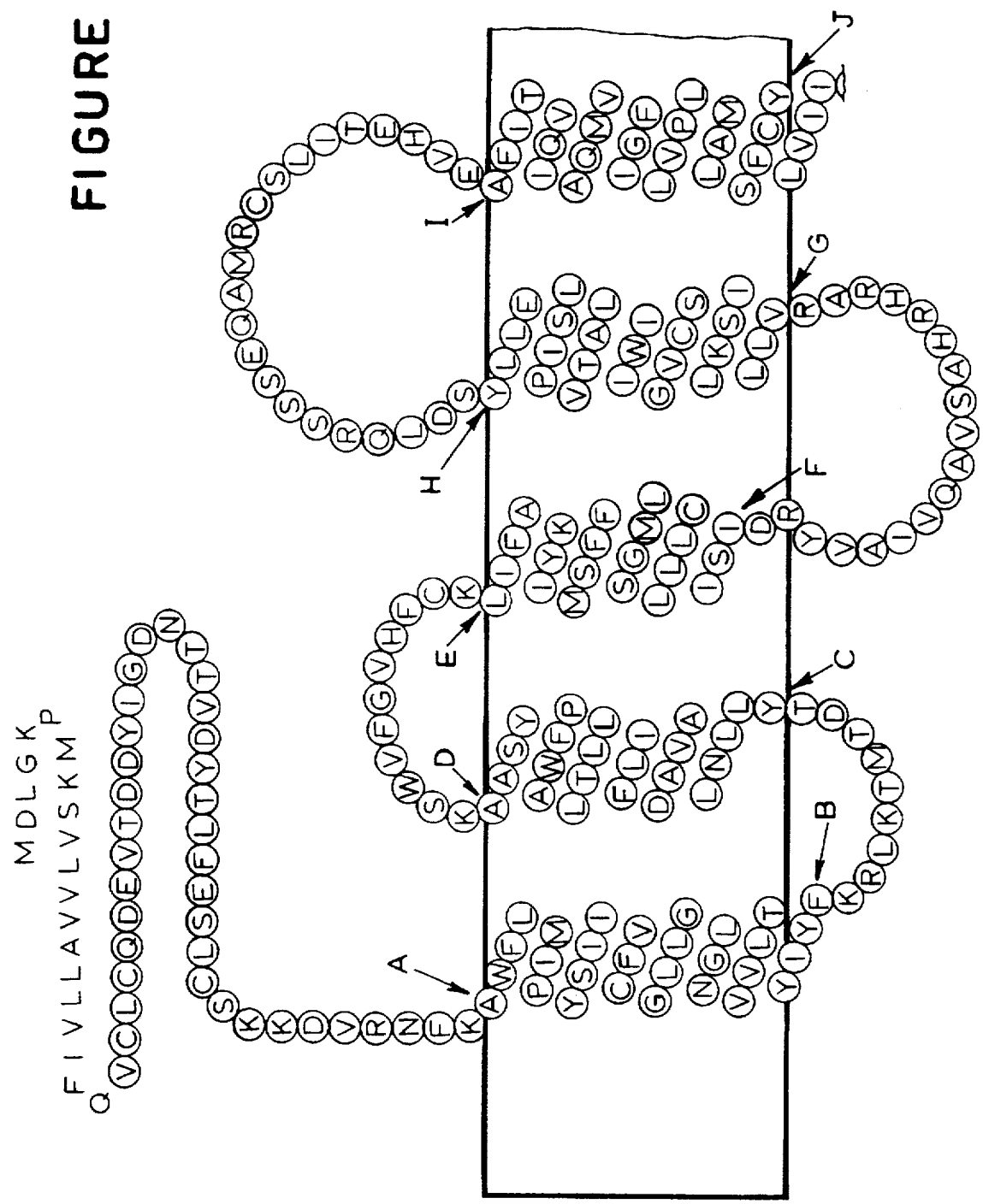

The present invention is illustrated by the following examples relating to the isolation of human genomic and cDNA sequences encoding the novel 7TM receptors herein designated V28, V31, V112, R20, R2, R12 and RM3. More particularly, Example 1 describes the isolation of PCR fragments encoding portions of the R20, V31, V28 and V112 7TM receptors. Example 2 describes the isolation of a full length human V31 genomic clone. Example 3 describes the isolation of a V31 human cDNA clone and further characterization of the V31 genomic clone. Example 4 presents experiments which reveal the chromosomal location of the human V31 gene. Example 5 describes the cloning of a full length murine V31 genomic clone. The cloning of a full length, human genomic clones for V28 is described in Example 6. Example 7 describes the isolation of a full length human V28 cDNA. Example 8 sets out a description of a full length human V112 cDNA. Example 9 describes the isolation of a full length genomic DNA encoding human R20. The isolation of full length R2 and R12 7TM receptor genes from a human genomic fetal liver library is detailed in Example 10. Example 11 describes the cloning of a cDNA encoding the RM3 7TM receptor. Example 12 presents a comparison of the amino acid sequences of 7TM receptors of the invention with amino acid sequences of previously described 7TM receptors. The transfection of human cells with genomic and cDNA sequences encoding the 7TM receptor V31 and the phenotype of the transfected cells are detailed in Example 13. Expression of 7TM receptors of invention in various human tissues and hematopoietic cell lines as assayed by Northern blot and in situ hybridization is described in Example 14. Examples 15 and 16 respectively describe the expression of V31 and R20 genomic sequences as fusion proteins with Glutathione-S-Transferase in *E. coli*, while Example 17 describes the expression of V31 and V28 cDNA sequences as fusion proteins with Glutathione-S-Transferase in *E. coli*. Example 18 describes the generation of polyclonal sera reactive with the V31 fusion proteins and V31 peptides useful for generating monoclonal and polyclonal antibodies specific for V31. Example 19 presents various methods for identifying extracellular and intracellular ligands of the 7TM receptors of the invention.

EXAMPLE 1

The polymerase chain reaction (PCR) was chosen as a method for identifying new members of the 7TM receptor superfamily.

Design and Synthesis of PCR Primers

Initially, eight different degenerate oligonucleotide primer pools were designed based on the amino acid sequence of the Platelet Activating Factor receptor. PCR with the eight primer pools failed to amplify any new 7TM receptor sequences although several Platelet Activating Factor receptor clones were amplified.

A second set of degenerate primers was then designed from regions of amino acid sequence high similarity between IL8R1 and AT2R which have an overall amino acid similarity of 30%. The first region of high similarity occurs in the second transmembrane domain and contains 16 of 20 residues that are identical in both receptors. A 5' degenerate primer pool (where each primer was 45 nucleotides in length plus a cloning site, a longer primer than typically is used for PCR) was synthesized based on this sequence. The sequence of the upstream primer is set out in IUPAC nomenclature below, wherein the underlined nucleotides represent a BamH1 site introduced to facilitate cloning.

Primer pool 1 (SEQ ID NO: 1)
<u>GAC GGA TCC</u> GTT TTT CTG TTG AAT TTG GCT CTG GCT
GAC YTA YKC TTT KYM CTG ACY TTG CCM MTS TGG This oligonucleotide pool was degenerate at ten positions to account for multiple codon choices and the four amino acid differences between IL8R1 and AT2R. Ten positions were not degenerate, but were designed instead with a single 'best guess' nucleotide based on human codon frequency tables in Wada et al., *Nucl. Acids Res.*, 19S: 1981–1986 (1991).

A second region of extended identity between IL8R1 and AT2R occurs in the putative second cytoplasmic domain where eight identical adjacent residues are shared. This region was utilized to design a downstream antisense PCR primer pool (21 nucleotides in length plus a restriction site). The sequence of the downstream primer is set out in IUPAC nomenclature below, wherein the underlined nucleotides represent a HindIII site introduced to facilitate cloning.

Primer pool 2 (SEQ ID NO: 2)
GGC TAA <u>GCT TGI ACI ATI GC</u>(Y or I) AGR TAI CGR TC This oligonucleotide contained the nucleotide inosine at several of the degenerate positions because of its ability to base pair with multiple nucleotides.

Isolation of Genomic DNA Sequences Encoding Novel 7TM Receptors by PCR

Oligonucleotide primer pools 1 and 2 were used to amplify human genomic DNA purified from leukocytes by the method of Blin and Stafford, *Nucl. Acids Res.*, 3: 2303–2308 (1976). PCR was performed in a Perkin-Elmer-Cetus machine with the following thermocycling parameters: an initial four minutes to bring the reaction to 94° C., followed by 25 cycles of (1) 94° C. denaturation step for 30 seconds, (2) 50° C. annealing step for 45 seconds, and (3) 72° C. extension step for two minutes. The reaction mixture contained 1×PCR buffer, 0.25 mM dGTP, 0.25 mM dATP, 0.25 mM dCTP, 0.25 mM TTP, 0.01 µg/µl primer pool 1, 0.01 µg/µl primer pool 2, 0.125 mg/ml human genomic DNA, and 2.5 units Taq polymerase in a total reaction volume of 40 µl. The predominate PCR product observed was the predicted size of 192 base pairs (bp) as determined by electrophoresis on a 1.2% agarose gel. Eight different PCR reactions were performed with increasing amounts of $MgCl_2$ ranging from 0.5 mM to 2.25 mM. The concentration of $MgCl_2$ did not appear to change the quantity of PCR product so all eight reactions were pooled, extracted with phenol and chloroform, ethanol precipitated, and then digested with restriction endonucleases BamHI and HindIII. The digested DNA was electrophoresed on 1.2% agarose and the 192 bp band was excised and eluted from the gel. The recovered DNA was then ligated into BamHI-HindIII digested plasmid Bluescript SK– (Stratagene Cloning Systems, La Jolla, Calif.) and transformed into bacterial host XL-1Blue. Several thousand clones were obtained and most appeared to be recombinants as determined by blue-white color selection.

Twenty different clones were chosen for DNA sequence analysis. Plasmid DNA was prepared and sequenced by the dideoxy chain termination method. Most of the plasmids contained sequences corresponding to IL8R1 or AT2R, but two of the twenty clones contained a unique sequence which encoded a peptide with 28% similarity to IL8R1 and 46% similarity to AT2R. This novel sequence was termed R20 and encoded a series of amino acids consistent with a 7TM receptor: the first 17 residues were generally hydrophilic and contained a highly conserved cysteine residue and the last 22 residues were hydrophobic, corresponding to the third transmembrane domain.

In order to identify additional novel sequences, the clones obtained by PCR using primer pools 1 and 2 were screened by hybridization to eliminate IL8R1, AT2R and R20 clones. Approximately 1000 clones were individually isolated and grown in microtitre wells. With the aid of a pronging device, the colonies were stamped onto plates, grown overnight, and transferred to nitrocellulose. DNA on the blots was denatured and prepared by standard methods. Hybridization was then performed with $^{32}$P-labelled probes specific for IL8R1, AT2R, and R20. Clones which did not hybridize were then chosen for sequence analysis. Three new clones were identified that appeared to encode 7TM receptor segments. The inserts of the clones were designated V31, V28, and V112. The sequence of the insert encoding V112 (ATCC 75326) is set out in SEQ ID NO: 3. Entire genes encoding the putative 7TM receptor genes designated V31, V28 and R20 were isolated from human genomic DNA libraries cloned in lambda phage as described below in Examples 2, 6 and 9, respectively.

EXAMPLE 2

A V31 genomic clone was isolated by PCR using the specific primers set out below.

Primer V31-forward (SEQ ID NO: 4)

TGG GCC TAC AGC GCG GCC AA

Primer V31-reverse (SEQ ID NO: 5)

TC AAT GCT GAT GCA AAG AAG

A human genomic DNA lambda library (ATCC 37333) was fractionated into 150 pools of approximately 3000 clones each. The 150 pools were divided into 15 groups, each containing ~30,000 phage. PCR with the V31 specific primers was performed with the following parameters: an initial four minutes to bring the reaction to 94° C., followed by 30 cycles of (1) 94° C. denaturation step for 30 seconds, (2) 50° C. annealing step for 45 seconds, and (3) 72° C. extension step for two minutes. The reaction mixture contained 1×PCR buffer, 0.25 mM dGTP, 0.25 mM dATP, 0.25 mM dCTP, 0.25 mM TTP, 0.01 µg/µl V31 forward primer, 0.01 µg/µl V31 reverse primer, 1 µl phage pool lysate, and 2.5 units Taq polymerase in a total reaction volume of 50 µl. One of the 15 groups yielded a PCR fragment of the predicted size of 114 bp, and a single pool of this group also produced the same fragment when subjected to the same PCR conditions. Hybridization was then used to identify the V31 coding phage. Approximately 6000 phage were plated on five 15 cm plates. Duplicate filters were absorbed to each plate and processed for hybridization by standard methods. A $^{32}$P labeled probe was prepared from the V31 segment plasmid by incorporating $^{32}$P-dCTP into a PCR reaction with the V31 specific primers. Hybridization with this radiolabeled probe and washing of filters was performed under conditions of reduced stringency. The hybridization solution was 20% formamide, 5×SSC (0.75M sodium chloride, 0.075M sodium citrate), 533 Denhardt's solution [1% polyvinyl pyrolidone (Sigma, St. Louis, Mo.), 1% ficoll, 1% bovine serum albumin-fraction V], 0.05M sodium phosphate, pH 6.5, and 50 ng/ml sonicated salmon sperm DNA (Sigma). After overnight hybridization at 42° C., the filters were washed extensively in 2×SSC at 42° C. A hybridizing clone was chosen for plaque purification, DNA isolation, and restriction endonuclease analysis. Hybridizing EcoRI and KpnI fragments were subcloned and subjected to DNA sequence analysis. The sequence demonstrated that the V31 coding sequence had indeed been isolated and matched completely the 114 bp sequence cloned by PCR. However, the sequence did not contain the entire 5' end of the coding region.

Consequently, more V31 genomic sequences were isolated from a different human placenta genomic library in vector lambda-Fix-II (Stratagene). Approximately 600,000 phage were screened by hybridization with the 5' end of the V31 coding sequence (EcoRI-PstI fragment). The probe was prepared by labeling approximately 100 ng of the denatured V31 DNA fragment in a reaction containing $^{32}$P-dCTP, $^{32}$P-dTTP, dGTP, dATP, random hexamer primers, and the Klenow fragment of DNA Polymerase I. Unincorporated nucleotides were removed by passing the reaction mixture over a G-25 Sephadex Quick Spin Column (Boehringer Mannheim). The probe was denatured by boiling and then incubated with the phage filters overnight at 42° C. in hybridization solution (50% formamide, 5×SSC, 5×Denhardt's, 0.05M sodium phosphate, pH 6.5) and 50 ng/ml sonicated salmon sperm DNA. Filters were washed three times in 0.2×SSC, 0.1% SDS at 42° C. for 10 minutes. Filters were air dried and then autoradiographed. Six independently hybridizing clones were chosen for plaque purification and restriction endonuclease analysis. Four of these clones produced hybridization patterns identical with genomic Southern blots using the V31 coding sequence probe. The hybridizing 1.9 Kb PstI fragment from one of these phage was isolated and subcloned into the PstI site of plasmid Bluescript SK+ (Stratagene). The resulting plasmid was subjected to DNA sequence analysis and was found to contain the entire V31 coding sequence. The predicted ATG initiation codon was preceded immediately by nucleotides agreeing with the Kozak consensus sequence for translation initiation [Kozak, Nucl. Acids Res., 12: 857–872 (1984)]. The DNA and amino acid sequences of the V31 genomic clone (ATCC 75327) are respectively presented in SEQ ID NOS: 6 and 7. The sequence of the V31 clone is more homologous to the IL8R1 (31%) and AT2R (27%) than to other members of the 7TM receptor superfamily (e.g., rhodopsin, the adrenergic receptors or the olfactory receptors).

EXAMPLE 3

Isolation of a Human V31 cDNA

A human cDNA encoding the 7TM receptor V31 was isolated. First, a partial cDNA clone was amplified by PCR from a human tonsil cDNA library made by standard methods in vector pCDM8 [Invitrogen, San Diego, Calif.]. The primers utilized in the PCR reaction were:

Primer V31-G+ (SEQ ID NO: 8)

GGTGAATTCAGGCTTTAAAGTTCCGCAC
Primer CDM8-Down (SEQ ID NO: 9)
GCAGAACTGGTAGGTATGGA Primer V31-G+ corresponds to the complement of nucleotides 418 to 437 of SEQ ID NO: 6 and includes an EcoR1 site (underlined) and three additional nucleotides at its 5' end to facilitate cloning. Primer CDM8-Down annealed to the polylinker of the vector pCDM8. The resulting PCR products were blotted to nitrocellulose and probed with a radioactive V31-specific probe. The radioactive probe was produced by annealing two oligonucleotides, the sequences of which are set out in SEQ ID NOS: 10 and 11, and filling in the ends of the annealled oligonucleotides with 32P-labelled nucleotides. A hybridizing band was isolated from the gel and cloned in Bluescript (SK–) (Stratagene). The resulting clone was named pV31-5' end and its DNA sequence is set out in SEQ ID NO: 12. Nucleotides 58–117 of pV31-5' end comprise coding sequences that are different from the original genomic clone set out in SEQ ID NO: 6, while nucleotides 118–232 are identical to nucleotides 322 to 437 of SEQ ID NO: 6.

A full length cDNA clone was isolated from a peripheral blood mononuclear cell cDNA library. PCR using V31-specific oligonucleotide primers was performed to identify fractions of the library containing V31 clones. The primers utilized were:

Primer V31-B1 (SEQ ID NO: 13)
GCACAGCCTTCCTGTGTGG

Primer V31-reverse (SEQ ID NO: 5) Primer V31-B1 corresponds to nucleotides 18 to 36 of SEQ ID NO: 12. Individual fractions positive for V31 were plated out and probed with the V31-specific radioactive probe described above for isolation of the V31-5' end clone. Clone PBMC75 was isolated and included a poly-A tail but was five nucleotides shorter at the 5' end than the partial tonsil cDNA set out in SEQ ID NO: 12. The V31 cDNA insert in clone PBMC75, which includes the complete coding sequences for the V31 7TM receptor, was named cDNA V31-B.

RACE PCR performed using a 5'-Amplifinder RACE kit (Clonetech) was used to amplify and clone the 5' end of the V31 cDNA. Primers V31-F (SEQ ID NO: 52) and V31-G+ (SEQ ID NO: 8) were utilized in the reactions along with primers included in the kit to clone cDNAs which included seventeen additional noncoding nucleotides (five of which were the same as the additional five identified in the original tonsil clone) upstream of the V31-B cDNA. A composite sequence including the seventeen nucleotides and the V31-B cDNA sequence is presented in SEQ ID NO: 14 and the amino acid sequence deduced therefrom is presented in SEQ ID NO: 15. The predicted seven transmembrane domains of the V31 7TM receptor (schematically marked in FIG. 1 as regions A to B, C to D, E to F, G to H, I to J, K to L, and M to N) correspond to amino acid residues 58 to 86, 96 to 119, 131 to 152, 171 to 196, 219 to 247, 264 to 285 and 306 to 331 of SEQ ID NO: 15.

Recharacterization of the Human V31 Genomic Clone

A comparison of the amino acid sequence deduced from V31-B with the amino acid sequence deduced from the V31 genomic clone described in Example 2 revealed that the two sequences differed at the amino terminus. The first fifty-two amino acids deduced from the genomic clone (residues 1 to 52 of SEQ ID NO: 7) were not present in the amino acid sequence deduced from V31-B cDNA and were replaced instead with twenty different amino acids (residues 1–20 of SEQ ID NO: 15). This result indicated that that the 5' end of the genomic clone was likely to contain an intron or introns.

Consequently, the V31-B cDNA sequence was used to identify three exons in the human V31 genomic clone described in Example 2. The DNA and deduced amino acid sequences of exons 1 and 3 (along with partial intron sequences) of the V31 genomic clone are set out in SEQ ID NOS: 16 and 17, and 18 and 19, respectively. Nucleotides 151–156 of SEQ ID NO: 16 (exon 1) comprise a putative TATA box while nucleotide 180 appears to be the site of transcription initiation and nucleotides 243–245 appear to comprise the start codon. Another promoter region, a CAAT box, which is thought to modulate transcription by RNA polymerase II [Benoist et al., *Nuc. Acids. Res.*, 8: 127–142 (1980)] has the consensus sequence GG(C/T)CAATCT (SEQ ID NO: 21). A similar sequence sequence is found at nucleotides 104–113 of SEQ ID NO: 16. The DNA and deduced amino acid sequences of the second exon of V31, as inferred from cDNA V31-B, are respectively set out in SEQ ID NOS: 21 and 22. Amino acids 6–15 of SEQ ID NO: 22 (exon 2) comprise a hydrophobic sequence shorter than, but similar to, that identified in a corresponding region of the serotonin receptor [Ruat et al., *Proc. Natl. Acad. Sci. USA*, 90: 8547–8551 (1993)] as a possible additional transmembrane domain or a cleavalble signal sequence. The intron sequences set out in SEQ ID NO: 18 (exon 3) include a stretch of nucleotides encoding an alu repeat.

EXAMPLE 4

The chromosomal position of the V31 gene was determined by Southern blot analysis of human-murine somatic cell hybrids [Naylor et al., *J. Exp. Med.*, 57: 1020–1027 (1983)] and in situ hybridization of metaphase chromosomes [Cherif et al., *Hum. Genet.*, 81: 358–362 (1989) and Fan et al., *Proc. Natl. Acad. Sci. USA*, 87: 6223–6227 (1990)].

DNA was isolated from human-mouse somatic cell hybrids, digested with EcoRI, and hybridized on Southern blots using the human V31 gene (the 1.9 Kb PstI fragment described in Example 2) as a probe. Hybridization of the V31 gene consistently segregated with human chromosome 17. To localize the V31 gene more specifically, in situ hybridization was performed on human metaphase chromosomes with a fluorescently labelled V31 gene probe (again the 1.9 Kb PstI fragment described in Example 2). Fluorescent in situ hybridization to metaphase chromosomes was used to localize the V31 genomic clone to the q12-q21.2 region of chromosome 17. Metaphase chromosomes were prepared from 5-bromodeoxyuridine synchronized lymphocyte cultures. The probe was biotinylated, hybridized to the chromosome spreads and detected by fluorescein-conjugated avidin (Vector Labs). Slides were evaluated with a Nikon fluorescence microscope. Forty-five metaphase preparations were examined. Q- (DAPI counterstaining) and R-banding (propidium iodide counterstaining) were used to confirm the identity of the chromosome. Fluorescent signal was detected at 17q12-q21.2 on both chromatids of chromosome 17 in eighteen out of the forty-five cells. This is the same chromosomal localization identified for inherited familial breast cancer [Hall et al., *Science*, 250: 1684–1689 (1990)].

EXAMPLE 5

A V31 genomic clone was isolated from a mouse genomic library library made by standard methods from a mouse cell line named C6VL using the 1.9 Kb V31 gene as a probe. The library was probed at reduced stringency (30% formamide at 42° C.). The DNA and deduced amino acid sequences of the murine V31 genomic clone isolated are set out in SEQ ID NOS: 23 and 24, respectively.

EXAMPLE 6

The PCR fragment, the isolation of which was described in Example 1, encoding the 7TM receptor V28 was used to design synthetic oligonucleotides probes specific for V28. Two overlapping oligonucleotides were synthesized as shown below which represented coding and non-coding strands of the fragment with a 9 bp overlap in the center.

Primer V28L (SEQ ID NO: 25)

TGG ACT CAC TAT TTG ATA AAT GAA AAG GGC CTC CAC

AAT GCC ATG TGC AAA TTC ACT ACC

Primer V28R (SEQ ID NO: 26)

AAT GCT GAT GAC GGT GAT GAA GAA TAT GCT TCC AAA

AAA GCC GAT GAA GAA GAA GGC GGT AGT GAA

The two synthetic DNAs were annealed, and Klenow polymerase was used to incorporate 32P radiolabeled nucleotides into the resulting V28 specific probe (114 bp in length following reaction). The reaction contained 0.76 µg of each V28 oligonucleotide. 1X Klenow Buffer, 0.015 mM dATP, 0.015 mM dGTP, 10 µl 32P-dCTP (Amersham), 10 µl α-$^{32}$P-dTTP (Amersham) and 1.5 µl Klenow polymerase. The reaction was incubated at room temperature for 15 minutes and unincorporated counts were removed with the aid of a Quick-Spin G25 column.

The V28 probe (46×10$^6$ cpm) was denatured by boiling for 2 minutes and hybridized to the human placenta genomic library (Stratagene). The library contained 360,000 phage on 12 nitrocellulose filters and hybridization was performed overnight at 42° C. in the hybridization solution described above containing 30% formamide. Filters were washed extensively in 2×SSC at 32° C. and then exposed three days. Several strongly hybridizing signals were observed and plaque purified. The V28 probe hybridized to single restriction endonuclease fragments in Southern blots of the phage DNA and human genomic DNA. Both HindIII (about 2 kbp) and Pst I (about 3.5 kbp) fragments were isolated, subcloned in pBluescript and sequenced. The DNA and deduced amino acid sequences of the full length V28 genomic clone (ATCC 75330) are respectively set out in SEQ ID NOS: 27 and 28. The gene contained the exact V28 sequence isolated by PCR. The encoded amino acid sequence predicts a structure consistent with typical 7TMR structure: there are seven hydrophobic domains separated by hydrophilic domains and highly conserved residues are found in their typical positions. The predicted seven transmembrane domains of the V28 7TM receptor correspond to amino acid residues 26 to 56, 68 to 92, 107 to 125, 146 to 167, 197 to 219, 232 to 253, and 273 to 297 of SEQ ID NO: 28. The V28 coding sequence is 29% homologous with IL8R1 and 27% homologous to AT2R.

EXAMPLE 7

A human V28 cDNA was isolated from a peripheral blood mononuclear cell cDNA library generated by standard methods in vector pRc/CMV (Stratagene). PCR using V28-specific oligonucleotide primers was performed to identify fractions of the library containing V28 clones. The primers utilized were:

Primer V28F (SEQ ID NO: 29)

TGG ACT CAC TAT TTG ATA AA

Primer V28X (SEQ ID NO: 30)

AAG ATT TGA GAG TCA GAG

Primer V28F corresponds to nucleotides 852 to 871 of SEQ ID NO: 27, while primer V28X corresponds to the complement of nucleotides 2047 to 2064 of SEQ ID NO: 27. The PCR reaction produced a 1.2 Kb DNA product that was labelled with $^{32}$P by random priming and then used as a probe to identify individual V28 clones. Hybridization and washing conditions were similar to the stringent methods described in Example 2.

The DNA and deduced amino acid sequences of the V28 cDNA clone are set out in SEQ ID NOS: 31 and 32, respectively. A comparison of the V28 genomic and cDNA clones revealed that there is an intron in the 5' untranslated portion of the V28 gene, the splice junction for which appear at nucleotides 84 to 85 of SEQ ID NO: 31.

EXAMPLE 8

A human V112 cDNA corresponding to the V112 genomic fragment described in Example 1 was isolated from a macrophage cDNA library made by standard procedures in vector pRc/CMV (Stratagene). PCR using V112-specific oligonucleotide primers was performed to identify fractions of the library containing V112 clones. The primers utilized were:

Primer V112-F (SEQ ID NO: 33)

TGGGTGGATAAAGAAGCATCTC

Primer V112-R (SEQ ID NO: 34)

AACACTCATGCAAGTGAGCA

Primer V112-F corresponds to nucleotides 1 to 19 of SEQ ID NO: 3, while primer V112-R corresponds to the complement of nucleotides 101 to 120 of SEQ ID NO: 3. The PCR reaction produced a 123 bp DNA product that was labelled with $^{32}$P by random priming and then used as a probe to identify individual V112 clones. Hybridization and washing conditions were similar to the reduced stringency methods described in Example 2.

Partial DNA and deduced amino acid sequences of the approximately 850 bp V112 cDNA clone are set out in SEQ ID NOS: 35 and 36, respectively. The partial sequence presented in SEQ ID NO: 35 contains V112 5' untranslated sequence and encodes the amino terminal portion of V112 up to the fourth transmembrane domain. The predicted seven transmbrane domains 1–3 of the V112 7TM receptor correspond to amino acid residues 36 to 58, 70 to 90, and 108 to 127 of SEQ ID NO: 36.

EXAMPLE 9

The R20 sequence isolated by PCR as described in Example 1 was used to screen a genomic library for the entire gene. A probe specific for R20 was prepared by amplifying the R20 partial sequence by PCR using the specific primer sequences set out below and $^{32}$P-labeled nucleotides, wherein primer R20-61 corresponds to the first 21 bases of the coding strand and primer R20-153RC corresponds to the first 20 bases of the non-coding strand.

Primer R20-61 (SEQ ID NO: 37)

CTA CAC GTA CCG GGA CTA TGA

Primer R20-153RC (SEQ ID NO: 38)

AGA AGA CGC TGG CGT ACA TG

The PCR reaction contained 0.07 µg R20 target sequence (Hind III-Bam fragment isolated from the R20 plasmid cloned in pBluescript SK–), 0.25 mM dATP, 0.25 mM dGTP, 0.25 mM dTTP, 1 µM dCTP, 4 µl $^{32}$P-dCTP (Amersham), 0.01 mg/ml R20 specific primers, 1×PCR buffer, and 0.5 µl Taq polymerase in a volume of 40 µl. The PCR was performed with the following thermocycling parameters: an initial four minutes to bring the reaction to 94° C., followed by 12 cycles of (1) 93° C. denaturation step for 30 seconds, (2) 50° C. annealing step for 30 seconds, and (3) 72° C. extension step for one minute. The unincorporated counts were removed with a Quick-Spin G25 column.

The probe was denatured by boiling for 2 minutes and then used to screen the human placenta genomic DNA library (Stratagene). Filters were hybridized overnight at 42° C. in hybridization solution containing 40% formamide, washed at 42° C. in 0.2×SSC and exposed overnight. Four strongly hybridizing signals were plaque purified, subcloned and sequenced. The R20 sequence identified by PCR was present in the isolated gene. The gene encodes a protein that has a structure similar to other 7TM receptors. The DNA and deduced amino acid sequences of the full length genomic R20 clone (ATCC 75328) are respectively set out in SEQ ID NOS: 39 and 40. The predicted seven transmbrane domains of the R20 7TM receptor correspond to amino acid residues 28 to 54, 66 to 90, 107 to 125, 146 to 167, 208 to 232, 246 to 267, and 285 to 312 of SEQ ID NO: 40. The R20 gene product is 28% homologous with the IL8R1 and 29% homologous with the AT2R.

EXAMPLE 10

During the isolation of the R20 gene, two weakly hybridizing sequences were identified which have significant homology to other 7TM receptor genes. The R20 specific probe (described in Example 9) was used to screen a human genomic fetal liver DNA library (ATCC 37333) by the methods described in Example 9. While the R20 gene could not be identified in this library, several weakly hybridizing clones were plaque purified, subcloned, and sequenced. The two clones were designated R2 (ATCC 75329) and R12 (ATCC 75331). The full length DNA and deduced amino acid sequences of R2 and R12 (which are respectively presented in SEQ ID NOS: 41 and 42, and 43 and 44) exhibit homology with other 7TM receptors. The predicted seven transmbrane domains of the R2 7TM receptor correspond to amino acid residues 41 to 69, 77 to 104, 120 to 138, 161 to 186, 207 to 226, 247 to 270, and 294 to 318 of SEQ ID NO: 42, while the predicted seven transmbrane domains of the R12 7TM receptor correspond to amino acid residues 33 to 57, 68 to 90, 106 to 127, 145 to 168, 193 to 217, 233 to 251, and 290 to 312 of SEQ ID NO: 44. R2 is 25% homologous to the IL8R1 and 24% homologous to the AT2R, while R12 is 26% homologous to the IL8R1 and 19% homologous to the AT2R.

EXAMPLE 11

Another novel 7TM receptor was identified by methods similar to those described in Example 1. The two degenerate primer pools (having SEQ ID NOS: 1 and 2, respectively) were used in a PCR reaction containing a human macrophage cDNA library in plasmid pRc/CMV (Stratagene). The reaction mixture contained 1×PCR buffer, 0.25mM dGTP, 0.25mM dCTP, 0.25mM dATP, 0.25mM TTP, 0.01 µg/µl primer pool 1, 0.01 µg/µl primer pool 2, 0.2 µg human macrophage cDNA library and 2.5 µl Taq polymerase in a reaction volume of 40 µl. When the PCR products were subjected to agarose gel electrophoresis a faint band of 180–200 bp was observed. To facilitate cloning, this DNA was eluted from the gel and re-amplified by PCR under the same conditions. Substantially more DNA was isolated following the second PCR. The re-amplified material was digested with BamHI and HindIII and cloned into the plasmid Bluescript SK–, as described in Example 1. Of sixteen clones sequenced, fourteen corresponded to R20 and two contained a unique sequence termed RM3. Specific primers for the partial RM3 clone were used to identify a full length RM3 cDNA clone by the PCR methods described in Example 2. The DNA and deduced amino acid sequence of the RM3 cDNA are respectively presented in SEQ ID NOS: 45 and 46. The predicted seven transmbrane domains of the RM3 7TM receptor correspond to amino acid residues 48 to 69, 82 to 100, 115 to 136, 159 to 179, 198 to 220, 246 to 274, and 287 to 311 of SEQ ID NO: 46. The sequence of the RM3 partial clone (ATCC 75340) is represented in SEQ ID NO: 45 as nucleotides 438 to 551. The RM3 deduced amino acid sequence exhibits 34% identity to the IL-8R and 32% identity to the AT2R.

EXAMPLE 12

Amino acid identity values among five of the seven novel 7TM receptors described in Examples 1 to 11 as well as values in comparison to various previously identified 7TM receptors are presented in Table 1 below, wherein fMLP is the N-formyl peptide receptor and ThrR is the thrombin receptor. The amino acid sequences of the previously identified 7TM receptors have been published as follows: IL8R1 in Holmes et al., supra; IL8R2 receptor in Murphy et al., Science, 253: 1280–1283 (1991); AT2R in Sasaki et al., supra; C5aR in Gerard and Gerard, supra; fMLPR in Boulay, BBRC, 168: 1103–1109 (1990); ThrR in Vu et al., Cell, 64: 1057–1068 (1991); and PAFR in Honda et al., supra.

TABLE 1

|       | V31-B | V28 | RM3 | R20 | R12 | R2 |
|-------|-------|-----|-----|-----|-----|-----|
| IL8R1 | 33    | 30  | 35  | 28  | 25  | 23  |
| IL8R2 | 34    | 32  | 34  | 30  | 27  | 27  |
| AT2R  | 28    | 28  | 32  | 29  | 28  | 24  |
| C5aR  | 27    | 24  | 26  | 25  | 26  | 27  |
| fMLPR | 25    | 24  | 29  | 24  | 23  | 29  |
| ThrR  | 19    | 25  | 20  | 21  | 29  | 21  |
| PAFR  | 27    | 25  | 23  | 24  | 27  | 20  |
| R2    | 27    | 24  | 24  | 24  | 25  | —   |
| R12   | 23    | 25  | 25  | 29  | —   | —   |
| R20   | 25    | 25  | 26  | —   | —   | —   |
| RM3   | 32    | 33  | —   | —   | —   | —   |
| V28   | 31    | —   | —   | —   | —   | —   |

EXAMPLE 13

V31 genomic DNA was transfected into CHO/DHFR⁻ cells (ATCC CRL9096) and 293 cells (ATCC CRL1573) and the cells were assayed for expression of V31 by Northern blot.

Vector Constructs for Expression of V31 in Mammalian Cells

The V31 coding sequence was excised from the full length lambda genomic clone described in Example 2 (λS-V31-3) as a 1.9 kb PstI fragment and ligated into commercial plasmid Bluescript SK+ (Stratagene) cut with PstI, to create an intermediate construct designated pV31-Pst. The entire V31 fragment plus 60 bp of flanking polylinker sequence was then cut out of pV31-Pst with HindIII and XbaI and ligated into commercial mammalian expression plasmid pRc/CMV (Invitrogen Corporation, San Diego, Calif.) cut with HindIII and XbaI.

Transfection of CHO and 293 Cells

The V31 expression construct, pV3 1XP, was transfected into CHO and 293 cells by lipofection using the commercial transfection reagent DOTAP (Boehringer Mannheim Corporation, Indianapolis, Ind.). Following selection for G418 resistance, individual V31 transfectants were subcloned.

Northern Blot Analysis

Specific expression of the V31 mRNA in transfected cells was assayed by Northern blot hybridization with a $^{32}$P- labelled V31 probe. Transfectants were grown to log phase, then centrifuged and washed one time with Phosphate Buffered Saline. mRNA was isolated from cells using the commercial Micro-Fast Track mRNA isolation kit (Invitrogen Corporation). mRNA species were separated by electrophoresis through 1% agarose gels with 2.2M formaldehyde. Samples were first denatured by incubating 15 minutes at 65° C. in 50% formamide and 2.2M formaldehyde, then bromphenol blue and ethidium bromide were added prior to loading the gel. mRNA was electrophoresed at 50 V for approximately 4 hours. After visualizing by UV trans-illumination and photography, mRNA in the gel was transferred to nitrocellulose (Schleicher & Schuell, Keene, N.H.) by capillary action overnight in 20×SSC. Nitrocellulose blots were baked at 80° C. in a vacuum oven for 1–2 hours prior to hybridizing with probes.

To generate the radiolabelled V31 probe, template DNA (1.9 kb HindIII-XbaI fragment containing entire V31 coding sequence) was denatured by boiling, then annealed to a mixture of random hexamer primers. Primers were extended for 30 minutes at room temperature using Klenow enzyme and a mixture of $^{32}$P-dCTP, $^{32}$P-dTTP, dATP, and dGTP. Unincorporated nucleotides were removed by passing the reaction mixture over a G-25 Sephadex Quick Spin Column (Boehringer Mannheim). Incorporation of $^{32}$P was assessed by Cherenkov counting. The probe was denatured by boiling and then incubated with the mRNA blot overnight at 42° C. in hybridization solution (50% formamide, 5×SSC, 5×Denhardts, 50 mM NaPO4, 10 ug/ml denatured salmon DNA). Blots were washed in 2×SSC, 0.1% SDS at room temperature 2 times for 10 minutes each, and then in 0.1×SSC at 50° C. 3–4 times for 10 minutes each. Blots were air dried and then exposed to X-ray film for varying lengths of time.

Only one of twelve transfected CHO clones expressed V31 mRNA as determined by hybridization. This cell line was designated CHO-V31-10. The signal from this cell line was observable within eight hours, while the other lines failed to produce significant amounts of signal.

Of the nine transfected 293 cell lines, two expressed V31 mRNA at very high levels (designated 293-V31-1 and 293-V31-6), three expressed at moderate levels (designated 293-V31-5, 293-V31-7, and 293-V31-9) and four failed to express significantly.

Phenotype of Transfected 293 Cells Expressing V31 mRNA

The phenotype of transfected 293 cells expressing V31 mRNA is altered in comparison to parental 293 cells. Parental 293 cells contain processes which protrude from the cellular surface. Such protrusions (or "spikes") are a common feature of many transformed cell types. The cells do not flatten out onto plastic but show a high profile with localized points of adhesion (thus the spikey description) and do not form a smooth epithelial sheet. In contrast, 293 transfectants expressing high levels of V31 mRNA (293-V31-1 and 293-V31-6) appear flat and smooth in culture. The cells make close and continuous contact with each other to form a smooth epithelial sheet with a cobbled appearance. The V31 transfected 293 cells also exhibit a marked decrease in their growth rate compared with the parental 293 cell line. These morphological and growth rate differences are consistent with a "less transformed" phenotype for V31 gene expression. These results are in marked contrast to other 7TM receptor-transfected cells. For example, the serotonin receptor confers a more transformed phenotype when transfected into mammalian cells [Julius et al., *Science*, 244: 1057 (1989)].

Expression of V31 cDNA in Mammalian Cells

The V31-B cDNA was also engineered for mammalian cell expression in pRc/CMV by methods similar to those described above. The resulting expression plasmid was designated pRcV31-B. The 293 cells transfected with the expression plasmid which were expressing V31-B mRNA exhibited a phenotype similar to parental 293 cells rather than to 293 cells transfected with the V31 genomic DNA constructs.

EXAMPLE 14

Expression of mRNA of the novel 7TM receptors V31, V28 and R20 was assayed by Northern blot analysis and in situ hybridization with radio-labelled probes in a variety of human tissues and hematopoietic cell lines.

Hybridization of V31 Probes to Human Tissues in situ

Frozen sections from various human tissues were hybridized in situ with radiolabelled single-stranded RNA probes derived from V31. Tissue samples obtained from lymph node, spleen, thymus, and tonsil were frozen in OTC blocks and stored at −70° C. Blocks were cut into 6 micron sections using a cryostat 2800M (Leica) and applied to slides coated in Vectabond (Vector Laboratories, Burlingame, Calif.). Slides were air dried overnight at room temperature than placed at −70° C. for storage. Prior to use, slides were removed from 70° C. and placed at 55° C. for 5 minutes. Sections were then fixed in 4% paraformaldehyde for 20 minutes at 4° C., rinsed 3 times in PBS, dehydrated (70–95–100% ethanol, one minute each at room temperature), and then allowed to dry for 30 minutes. Sections were denatured in 70% formamide, 2×SSC for 2 minutes at 70° C., rinsed in 2×SSC, dehydrated, and then air dried for 30 minutes. The sections were then incubated in prehybridization solution (50% formamide, 0.3M NaCl, 20 mM Tris pH 8.0, 10% dextran sulfate, 1×Denhardt's solution, 100 mM DTT and 5 mM EDTA) for 2 hours at 42° C., radiolabelled probe was added to the solution (6×10$^5$ cpm/section) and the sections allowed to hybridize for 12–16 hours at 50° C. To generate sense and anti-sense V31 probes, T7 and T3 RNA polymerases were used to synthesize $^{35}$S-labelled transcripts from a linearized, gel purified plasmid containing a 727 bp HincII fragment of V31.

After hybridization, sections were washed in 4×SSC, 10 mM DTT for 1 hour at room temperature, then in 50% formamide, 1×SSC, 10 mM DTT for 40 minutes at 60° C., and finally in 2×SSC and 0.1×SSC for 30 minutes each at room temperature. After alcohol dehydration, the air dried slides were dipped in Kodak NTB2 Nuclear Emulsion (heated to 42° C.) and allowed to dry for 2 hours at room temperature in complete darkness until time of development. Slides were then placed in Kodak D19 developer for 4 minutes at 4° C., dipped 4 times in Acid Stop (1 ml Glacial acetic acid/500ml distilled water) and then placed in Kodak fixer for 4 minutes at 4° C. The slides were rinsed 3 times in tap water and then counterstained with hematoxylin/eosin.

The V31 antisense probe hybridized intensely with each of the four human tissue samples (lymph node, spleen, thymus, and tonsil). In contrast, the control probe produced from the V31 sense strand did not hybridize significantly to these tissues.

Northern Blot Analysis of V31 Expression in Human Tissues

Specific expression of V31 mRNA in normal human tissues was also assayed by Northern blot hybridization. RNA was prepared from human tissues by standard methods [see, for example, Chirgwin et al., *Biochemistry*, 18:

5294–5299 (1979)] and fractionated on oligo-dT cellulose for enrichment of mRNA. The mRNA samples were separated on a formaldehyde-agarose gel, transferred to nitrocellulose, and hybridized to the V31 $^{32}$P-labeled probe as described in Example 13. The V31 probe clearly hybridized to the human lymphoid tissues, tonsil, lymph node and spleen. No hybridization was observed to adrenal gland, brain, heart, kidney, liver, lung, pancreas or testis. Small amounts of hybridization were observed to small intestine, which may represent lymphoid projections into this tissue.

Northern Blot Analysis of V31 Expression in Hematopoietic Cell Lines

Cells from several hematopoietic cell lines were grown to log phase, harvested by centrifugation, washed two times with 150 mM NaCl, and the pellets stored frozen at –70° C. To extract RNA, pellets were resuspended in guanidinium isothiocyanate buffer (GIT) and sheared in a polytron mixer for 20 seconds. RNA/GIT mixtures were layered on top of CsCl and centrifuged at 35,000 rpm (179,000×g) for 21 hours. RNA pellets were resuspended in $H_2O$, ethanol precipitated, and treated with Proteinase K to remove any RNase contamination. After a phenol/chloroform extraction, the RNA, was reprecipitated, resuspended in $H_2O$ and quantitated spectrophotometrically.

10ug of each RNA sample was used for northern blot analysis. Samples were denatured and electrophoresed through a formaldehyde/agarose gel, transferred to nitrocellulose and hybridized to the $^{32}$P-labelled V31 probe essentially as described in Example 13.

The V31 probe hybridized strongly to the T cell line Hut 78 and the B cell lines Raji and Jijoye. The T cell line CEM also hybridized with V31, but less intensely. In contrast the T cell lines SKW3 and Molt4 failed to hybridize to V31, as did the myeloid lines KG1, K562, HL-60, and U937. These results confirm the Northern and in situ hybridization results on human tissues; V31 is expressed specifically in lymphoid cells and tissues. Results of Northern blot assays for expression of V31 mRNA in other hematopoietic cell lines are presented below in Table 2.

TABLE 2

| | V31 Northern Blot Signal |
|---|---|
| T Cell Lines | |
| H9 | ++ |
| MOLT3 | ++ |
| JurkatE6-1 | – |
| J.RT3-T3.5 | – |
| CCRF-HSB-2 | + |
| B Cell Lines | |
| MC116 | + |
| Ramos | – |
| Daudi | – |
| CA46 | – |
| HS602 | ++++ |

Northern Blot Analysis of V28 Expression in Human Tissues and Cell Lines

Expression of V28 mRNA in a variety of human tissues was assayed by northern blot analysis using $^{32}$P-labelled V28 probes. Frozen tissue samples were pulverized in liquid nitrogen using mortar and pestle, and RNA was isolated following the APGC protocol of Chomezynski and Sacchi, *Analytical Biochemistry*, 162: 156–159 (1986). Briefly, samples were homogenized in a 4M guanidium thiocyanate buffer and then subjected to several rounds of acid phenol extraction and isopropanol precipitation. RNA samples were treated with RNase-free DNase (Stratagene Cloning Systems, La Jolla, Calif.) for 30 minutes at 37° C. to remove any contaminating DNA, then phenol/chloroform extracted twice, ethanol precipitated, resuspended in DEPC-treated $H_2O$ and stored at –70° C. until further use. RNA from cell lines was prepared as described above for the analysis of V31.

Ten to 30 µg of each RNA sample were denatured by incubating in 50% formamide and 3.5M formaldehyde for 10 minutes at 60° C.; bromphenol blue and ethidium bromide were added prior to electrophoresis. Samples were electrophoresed through 1.2% agarose gels containing 2% formaldehyde for 4 hours at 90 volts. After visualizing by UV trans-illumination and photography, RNA was transferred from the gel to nitrocellulose (Schleicher and Schuell) by capillary action overnight in 20×SSC. Nitrocellulose blots were baked at 80° C. in a vacuum over for 1–2 hours prior to hybridization A 1.5 kb Eco RI fragment containing the entire V28 coding sequence was used as a template to generate the radiolabelled V28 probes. Details of the labeling, hybridization and washing are exactly as described in Example 2. Results of the Northern blot analysis are presented in Table 3 below.

TABLE 3

| Tissue or Cell Line | V28 Northern Blot Signal |
|---|---|
| Spleen | + |
| Thymus | + |
| Tonsil | + |
| Lymph Node | +/– |
| Placenta | + |
| Ovary | + |
| Testis | + |
| Kidney | +/– |
| Liver | – |
| Brain | – |
| Heart | – |
| H9 (T cell line) | – |
| MOLT3 (T cell line) | – |
| Daudi (B cell line) | – |
| HL60 (Promyelocytic cell line) | + |
| U937 (Promyelocytic cell line) | + |
| THP.1 (Promyelocytic cell line) | ++++ |

Northern Blot Analysis of R20 in Human Tissues

Expression of the R20 gene in various human tissues was assayed by Northern blot analysis. Poly-A mRNA was isolated from various human tissues, fractionated by denaturing agarose gel electrophoresis, and blotted onto a nitrocellulose membrane.

A probe was prepared from the 1.5 kb HindIII-PstI fragment of R20 as follows. Fifty ng of gel-purified fragment was annealed to 1 µg of random hexamers. The sample was treated with Klenow enzyme in the presence of Klenow buffer (See Example 2), dATP, dGTP, $^{32}$P-dCTP, and $^{32}$P-TTP at room temperature for 75 minutes. The labelled fragment was separated from unincorporated nucleotides by passage through a G-25 Quickspin column (Boehringer Mannheim), denatured by boiling, and cooled on ice. This probe was hybridized to the filter for 16 hours at 42° C. in a solution of 5×SSC, 50 mM $NaPO_4$, 5×Denhardt's solution, and 10 µg/ml salmon sperm DNA. The filter was subsequently washed in 0.1×SSC at 50° C. Hybridization was visualized by autoradiography.

Of the tissues analyzed, the strongest signal was detected in placental RNA. A weaker band of the same apparent molecular weight was also visible in RNA from lymph nodes, kidney, and thymus. No hybridization to liver, ovary, or testis RNA was evident.

EXAMPLE 15

The coding sequence for V31 (and fragments thereof) were engineered for expression in *E. coli* as a fusion protein with Glutathione-S-Transferase (GST) [Smith et al., *Gene*, 67: 31–40 (1988)]. Fusion proteins with GST are generally expressed at high levels and can often be easily purified on glutathione-agarose beads. These fusions are useful for providing material for biochemical studies and as immunogens for the preparation of antibodies.

The entire coding sequence of V31 was engineered for expression in the plasmid pGEX-2T such that a fusion protein was produced containing GST at the amino terminal end and V31 at the carboxyl terminal end. The plasmid pGEX-2T contains a lac promoter which drives the expression of GST. The 3' end of the GST gene contains BamHI and EcoRI sites and encodes a thrombin cleavage site. The V31 gene was cloned into pGEX-2T digested with BamHI and EcoRI by first introducing a BamHI site at the 5' end of the V31 gene and an EcoRI site at its 3' end by PCR directed mutagenesis. A 5' oligonucleotide (V31-A, SEQ ID NO: 47) contained a BamHI site encoding residues 225 and 226 of pGEX-2T and 17 bases of the V31 gene, starting with the methionine initiation codon (ATG). The downstream, antisense oligonucleotide (V31-B, SEQ ID NO: 48) contained an EcoRI site and 17 bases of the 3' end of the V31 coding sequence including the natural stop codon. PCR was performed in a Perkin Elmer Cetus machine with the following thermocycling protocol: an initial four minutes to bring the reaction to 94° C., followed by 25 cycles of (1) 94° C. denaturation step for 30 seconds, (2) 60° C. annealing step for 30 seconds, and (3) 72° C. extension step for 30 seconds. The reaction mixture contained 1×PCR buffer, 0.25 mM dGTP, 0.25 mM dATP, 0.25 mM dCTP, 0.25 mM TTP, 0.01 μg/μl of each primer, $3\times10^{-7}$ mg template DNA and 2.5 units Taq polymerase in a total reaction volume of 50 μl. Following PCR, the reaction was extracted with phenol and chloroform and ethanol precipitated. The DNA was then digested at 37° C. with BamHI and EcoRI and electrophoresed on 1% agarose/2% Nusieve agarose gel. The predominant PCR product exhibited an to electrophoretic mobility consistent with the predicted size of 1241 bp. This DNA was electroluted and then ligated to a pGEX-2T DNA fragment that had been treated with BamHI and EcoRI and isolated by electrophoresis. The ligated DNA was transformed into competent *E. coli* and a clone containing the plasmid designated pGEX-V31-F4 was chosen for analysis. The insert DNA coding for the V31 fusion protein was sequenced by the dideoxy chain termination technique.

A shorter fusion protein, containing only the first 90 amino acids of V31 (the predicted first extracellular domain), was also prepared with GST. Similar to the above example, BamHI and EcoRI sites were introduced into the V31 coding sequence by PCR directed mutagenesis. The 5' oligonucleotide (V31-A) was identical to that utilized for the first GST fusion and contained a BamHI site for the GST gene and 17 bases of the V31 gene. The downstream antisense oligonucleotide (V31-C, SEQ ID NO: 49) contained 18 bases of the V31 gene and introduced a stop codon (after V31 amino acid 90) followed by an EcoRI site. PCR conditions were performed exactly as above for the first GST fusion. The PCR products were phenol/chloroform extracted and digested with BamHI and EcoRI. The DNA was electrophoresed on a 1% agarose/2% Nusieve agarose gel and exhibited a mobility consistent with a predicted size of 281 bp. This DNA was electroeluted and also ligated into pGEX-2T. The insert of the resulting plasmid, pGEX-V31-N1, was confirmed by sequence analysis.

A third fusion protein was prepared which contained GST fused to all of the four putative extracellular domains. Regions of the V31 amino acid sequence were defined as domains based on their predicted hydrophillicity and contained one to five hydrophobic residues at each end (forming portions of transmembrane segments); this design provides some separation between domains and yet does not change the general hydrophilic nature of the fusion protein. Four separate PCR reactions were performed to amplify DNA encoding each separate domain. The method used to then fuse the domain coding sequences is outlined in Erlich, Ed., pp. 61–70 in PCR *Technology*, Stockton Press, New York, (1989). The most 5' oligonucleotide (V31-A) used was identical to that used in the two V31 fusions described in the foregoing paragraphs and contained the BamHI site for ligation to the GST gene sequence. The most 3' oligonucleotide (V31-J, SEQ ID NO: 56) contained 17 bases of the V31 gene and introduced a stop codon after V31 amino acid 343, followed by an EcoRi site.

Oligonucleotide V31-D (SEQ ID NO: 50) was paired with the upstream oligonucleotide V31-A to amplify a 294bp fragment that coded for the first extracellular domain; the V31-A oligonucleotide also contains 12 bases which are homologous with the second extracellular domain oligonucleotide (V31-E, SEQ ID NO: 51). The second extracellular domain was amplified with oligonucleotides V31-E and V31-F (SEQ ID NO: 52). Oligonucleotide V31-E contains 12 bases of first extracellular domain followed by 17 bases of second extracellular domain sequence. Consequently the 3' end of the first extracellular domain PCR product contains 24 identical nucleotides when compared with the 5' end of the second extracellular domain PCR product allowing the two PCR products to be annealed together and reamplified as a fused DNA fragment (using PCR and oligonucleotides V31-A and V31-F). This strategy was also applied to the third and fourth extracellular domains: the third extracellular domain was amplified using oligos V31-G (SEQ ID NO: 53) and V31-H (SEQ ID NO; 54) and the fourth extracellular domain was amplified using oligos V31-I (SEQ ID NO: 55) and V31-J, and the resulting PCR fragments were annealed and reamplified using oligos V31-G and V31-J. Finally, the two DNA fragments containing the first/second and third/fourth extracellular domains were fused together by annealing the fragments and amplifying with oligonucleotides V31-A and V31-J in a tertiary PCR reaction. PCR conditions and digestion with BamHI and EcoRI were performed as as described for the first two V31 fusion proteins. Products of the initial four PCR reactions were electrophoresed on 1% agarose/2% Nusieve agarose and each reaction yielded the predicted size fragment (294 bp, 75 bp, 105 bp, and 111 bp for extracellular domains one through four, respectively). Secondary reamplification reactions were performed with the same PCR conditions, but the target sequences came from the electrophoresed gels which had been excised by stabbing the appropriate band with a micropipetor tip. The captured agarose (two or three microliters in volume) was then extruded into the secondary PCR reaction. These reactions produced the predicted size DNA fragments of 345 bp (first/second extracellular domains) and 192 bp (third/fourth extracellular domains). These DNA fragments once annealed were similarly used as template DNA in the final PCR reaction using oligos V31-A and V31-J. The final PCR product was digested with BamHI and EcoRI and exhibited a mobility consistent with the expected 513 bp. The DNA was electroeluted and ligated into pGEX-2T. The resulting plasmid was designated pGEX-V31-X10 and was confirmed to have the predicted DNA sequence.

The amplified sequences and junctions with the GST gene were sequenced to determine that all three designed genes were properly constructed. The three GST/V31 fusion genes were grown in *E. coli* and their synthesis was induced with IPTG. Cultures were grown to late exponential phase and harvested by centrifugation. Cells were resuspended in PBS and disrupted by sonication. Cellular debris was removed by centrifugation and the supernatant was mixed with Glutathione-agarose beads (Sigma). The beads were then extensively washed in PBS. Proteins bound to the beads were eluted with reduced glutathione (Sigma). Aliquots from each stage of purification were analyzed for protein by SDS-polyacrylamide gel electrophoresis. GST is easily purified by this method and represents the major (greater than 90%) protein eluted from glutathione agarose. The GST fusion protein containing the full length V31 coding sequence produced several protein bands of lower molecular weight (1000, 2500, and 4000 Da larger than GST) than that predicted for the full length fusion protein. These products were eluted from glutathione-agarose beads, but were expressed at lower levels than GST. These proteins may be the products of the fusion proteolysis (see below). No protein band was observed at the predicted molecular weight for the full length V31-GST fusion protein.

The GST fusion protein containing the first extracellular domain (pGEX-V31-N1) produced several protein bands that were purified on glutathione-agarose. One of these corresponded with the approximate predicted size (10,000 Da larger than GST) and three smaller bands exhibited mobilities identical with the GST fusion protein containing full length V31.

Purification of the GST fusion protein containing all four extracellular domains (pGEX-V31-X10) was also attempted. Only small amounts of protein were eluted from glutathione-agarose beads, and these had the same mobility as the pGEX-V31-F4 bands and the smaller pGEX-V31-X10 bands. However, a large amount of protein remained associated with the cell pellet and exhibited a mobility consistent with the predicted fusion protein size. Amino terminal amino acid sequencing was performed on this electrophoretically purified material, and the sequence was determined to be the amino terminal sequence of GST. This protein may thus represent the GST fusion protein with the four V31 extracellular domains which may form inclusion bodies during synthesis and therefore be insoluble and associated with the cell pellet.

There are several observations that suggest that V31 may recognize a protease. The structure of V31 is very similar to the thrombin receptor. V31 shares 30% similarity to the thrombin receptor and both molecules have unusually long first extracellular domains (89 residues for V31, 100 for thrombin). The thrombin receptor contains a thrombin cleavage site in this first extracellular domain and the receptor becomes activated following proteolysis. V31 contains a prominent proteolytic recognition sequence including five adjacent lysines (amino acid positions 18-22) that should be a good target for a protease specific for basic residues (several such proteases exist, such as trypsin). Moreover, experimental observations with GST-V31 fusion proteins suggest that the first extracellular domain is an obvious target for an *E. coli* protease. During the isolation of each of the three fusion proteins, some of the material was found to be partially degraded as described in the foregoing paragraphs. The sites of proteolysis are presumably in the first extracellular domain since that is the only sequence common to the three fusion proteins. The size (2500 Da larger than GST) of at least one of these potential degradation products is consistent with cleavage at or near adjacent lysines. This result suggests that the first extracellular domain is accessible to cleavage by *E. coli* proteases; such accessibility to a human protease may result in cleavage and subsequent V31 signal transduction events in vivo.

EXAMPLE 16

The extracellular domains of the R20 sequence were also engineered for expression in E. coli as a fusion protein with GST. As described in Example 15 for V31 domains, the R20 domains were chosen by their predicted hydrophillicity. Four independent PCR reactions were performed to amplify each domain.

The 5' oligonucleotide (R20-X1, SEQ ID NO: 57) encodes a BamHI site for ligation to the GST gene, followed by 15 nucleotides of the R20 gene (beginning with the methionine initiation codon). The most 3' oligonucleotide (R20-Y4, SEQ ID NO: 64) contained 18 residues of the R20 gene (fourth extracellular coding segment), introduced a stop codon after R20 amino acid 286, and was followed by an EcoRI site. The first extracellular domain coding sequence was prepared by PCR with oligonucleotides R20-X1 and R20-Y1 (SEQ ID NO: 58) using conditions described in Example 15. Similarly, the second, third, and fourth extracellular domain coding sequences were amplified with primer pairs R20-X2 (SEQ ID NO: 59) and R20-Y2 (SEQ ID NO: 60); R20-X3 (SEQ ID NO: 61) and R20-Y3 (SEQ ID NO:62); and R20-X4 (SEQ ID NO: 63) and R20-Y4, respectively. The first and second extracellular domain coding sequences were fused together by a secondary PCR reaction, similar to that described in example 15 (primers R20-Y1 and R20-X2 share 30 overlapping nucleotides which allow the two primary PCR products to anneal together for the amplification of a fused DNA fragment; the PCR reaction contains the two primary PCR products and primers R20-X1 and R20-Y2). The third and fourth extracellular domain coding sequences were similarly fused together in a PCR reaction with primers R20-X3 and R20-Y4. Finally, the PCR products from the secondary reactions were annealed and amplified in a tertiary PCR with primers R20-X1 and R20-Y4; this reaction produced a DNA which encoded the four extracellular domains. The DNA was digested with BamHI and EcoRI and then ligated into pGEX-2T as described in Example 15. The resulting plasmid was designated pGEX-RDF6 and the insert was confirmed by DNA sequence analysis.

As described in Example 15, *E. coli* harboring this plasmid were grown and analyzed for production of a GST-R20 domain fusion protein. A protein band of the appropriate mobility was observed on SDS-PAGE of glutathione agarose purified material. Several lower molecular weight species (about 1000 Da smaller) were also observed which may represent proteolytic cleavage products. All of these bands could be cleaved with thrombin to yield a band which co-migrated with GST. This result suggests that the *E. coli* cultures produce GST fusion proteins with R20 extracellular domain sequences. The material purified on glutathione agarose was directly used for immunization of mice for the preparation of antibodies as described below in Example 18.

EXAMPLE 17

By methods similar to those described in Examples 15 and 16, V31-B and V28 coding sequences were engineered to be expressed as GST fusion proteins.

The coding sequence of interest (from the V31-B cDNA described in Example 3 or the V28 cDNA described in Example 7) was cloned into the BamHI and EcoRI sites of pGEX-2T. A single bacterial colony containing this plasmid was used to inoculate 50 ml L broth/carbenicillin and was grown overnight at 37° C. The overnight culture was diluted 10-fold to 500 ml with L broth/carbenicillin and incubated for 1.5 hours at 37° C. IPTG was added to 1 mM and the culture was incubated for 3.5 hours at 37° C. Bacteria were pelleted, resuspended in 15 ml PBS/1% Triton X-100 and sonicated with five 45-second bursts while keeping ice cold. Homogenate was aliquoted and spun in a microfuge at full speed for 5 minutes. Pellets were resuspended in a total of 3 ml PBS/1% Triton X-100. Half of the sample was brought to 10 ml with 3.5 ml $H_2O$, 4.5 ml 2×sample buffer and 0.5 ml 2M DTT. The sample was boiled for 3 minutes and spun before loading on two 10% acrylamide SDS preparative gels. Gels were run at 30 mA for approximately 15 hours then incubated in ice cold 0.4M KCl to visualize protein bands. The induced band was cut out and electroeluted for 4 hours at 50 mA into approximately 10 ml Tris-glycine buffer (no SDS) in dialysis tubing. When necessary, the eluted fusion protein was concentrated in Amicon microconcentrators with 30 kD molecular weight cut-off.

EXAMPLE 18

Generation of Antibodies to V31 Fusion Proteins

The GST-V31 fusion proteins V31-N1 and V31-X10 described in Example 15 were purified on glutathione-agarose and emulsified with an equal volume of Freunds adjuvant (complete for the first injection and incomplete for all subsequent injections). Two Balb/c mice were initially immunized subcutaneously with approximately 200 µl of each construct. Subsequent boosts were made at two week intervals and the mice were bled retro-orbitally after three boosts.

Immunological reactivity was assessed by Western blot analysis. Approximately 25 µg of either the immunizing protein or GST was resolved on a 10% polyacrylamide gel and transferred to nitrocellulose. The filter was blocked in PBS containing 5% non-fat dried milk and 1% BSA for 2–15 hours at 4° C. The sera (either pre-immune or immune) was diluted 1:50 in blocking buffer in a final volume of 2 ml, incubated with the filter strip for 1 hour at 4° C. and washed three times with 50 ml of PBS. Sheep anti-mouse Ig conjugated to horseradish peroxidase (Amersham) was diluted 1:500 in PBS and incubated with each filter for 1 hour at 4° C. The filters were washed 3 times in 100 ml of PBS and placed in 5 ml of 3,3' diaminobenzidine (0.6 mg/ml in 10 mM Tris-HCl; 0.6% $NiCl_2$; 0.06% $H_2O_2$). Immunoreactivity to V31 fusion proteins was observed from sera of mice immunized to V31-N1 and V31-X10. In addition, immunoreactivity was observed to the thrombin cleaved V31-NI products (both GST and the V31 amino terminal domain). Generation of Antibodies to V31 Peptides V31 peptides to be used to generate V31 specific antibodies include, for example:

Peptide ECDN-B (Amino acids 1 to 15 of SEQ ID NO: 15) MDLGKPMKSVLC
Amino acid residue 12 (a cysteine) was added to the peptide to facilitate conjugation of the peptide to an immunogen carrier. Another peptide is:

Peptide ECD2 (Amino acids 116 to 129 of SEQ ID NO: 15 ) YSAAKSWVFGVHFC

Peptide ECDN-B corresponds to the amino terminal end of the first extracellular domain of V31 while peptide ECD2 corresponds to a region of the second extracellular domain of V31.

EXAMPLE 19

Various methods may be used to identify extracellular and intracellular ligands for the 7TM receptors of the invention.

For example, because 7TM receptors are coupled to G proteins to effect biological responses, the secondary signal transduction events [reviewed by Linder et al., Sci. Am., 267: 56–65, (1992)] that are utilized by G proteins can be utilized to assay for recombinant 7TM receptor function. Assays for the activity of G protein effector molecules (e.g., adenylyl cyclase, phospholipase C, ion channels, and phosphodiesterases) have previously been described. For example, concentration of cyclic AMP can be measured by a commercial radioimmunoassay; phosphoinositide production can easily be monitored [Downes et al., Biochem. J., 198: 133–140 (1981)]; and the transient release of intracellular calcium ion stores can be observed with spectrofluorimetry. These assays can be performed on mammalian cells expressing 7TM receptors of the invention in the presence and absence of test compounds to identify or purify potential ligands of the 7TM receptors and such assays may also be used for the identification or purification of agonists or antagonists of 7TM receptors.

As another example, a calcium flux assay can be used to identify solutions or cellular extracts containing ligands for 7TM receptors of the invention. Specifically, 293 cells transfected with DNA sequences of the invention encoding a 7TM receptor are grown in a 10 cm dish to ~90% confluence in MEM+10% serum. Cells are washed with CMF-PBS and loaded with Fura-2 by incubating in 4 ml MEM+10% serum+1 uM Fura-2 AM (Molecular Probes–1 mM stock made in DMSO and frozen in aliquots) for 30 minutes at room temperature. Cells are again washed and removed from plate with versene. Cells are pelleted, washed in D-PBS (containing 1 mM $Ca^{++}$) and resuspended in ~500 ul D-PBS for a concentration of ~$10^7$/ml. Fluorescence changes are monitored in a Hitachi F-4010 fluorescence spectrophotometer. Approximately $10^6$ cells are suspended in a total of 1.8 ml D-PBS with stirring in a cuvette maintained at 37° C. Excitation wavelengths alternate between 340 nm and 380 nm at 4 second intervals while emission is monitored at 510 nm. Test compounds are added through an injection port. At the end of the experiment, ionomycin is added to measure the maximal $Ca^{++}$ flux.

A transient $Ca^{++}$ flux is indicative of the presence of a ligand for the 7TM receptor in the solution being tested.

The foregoing illustrative examples relate to presently preferred embodiments of the invention and numerous modifications and variations thereof will be expected to occur to those in the art. Thus only such limitations as appear in the appended claims should be placed upon the scope of the present invention.

What is claimed is:

1. A purified and isolated polynucleotide encoding the amino acid sequence of V28 seven transmembrane receptor set out in SEQ ID NO: 28.

2. The polynucleotide of claim 1 which is a DNA.

3. The polynucleotide of claim 1 which is a cDNA.

4. The polynucleotide of claim 1 which is a genomic DNA.

5. The polynucleotide of claim 1 which is a wholly or partially chemically synthesized.

6. A host cell stably transformed or transfected with a DNA according to claim 2 in a manner allowing the expression in said host cell of V28 seven transmembrane receptor polypeptide.

7. A purified and isolated DNA encoding V28 seven transmembrane receptor and selected from the group consisting of:

(a) nucleotides 594 to 1658 of SEQ ID NO: 27; and (b) the insert of the plasmid having ATCC Accession No. 75330.

8. A DNA vector comprising a DNA according to claims 2 or 7.

9. The vector of claim 8 wherein said DNA is operatively linked to an expression control DNA sequence.

10. A purified and isolated DNA according to claim 7 comprising the insert of the plasmid having ATTC Accession NO. 75330.

11. A method for producing V28 seven transmembrane receptor polypeptide comprising the steps of growing a host cell in a suitable nutrient medium and isolating said polypeptide from said cell or said medium, wherein said host cell is stably transformed or transfected with a DNA encoding the amino acid sequence of V28 seven transmembrane receptor set out in SEQ ID NO: 28, in a manner allowing the expression in said host cell of V28 seven transmembrane receptor polypeptide.

12. A purified and isolated V28 seven transmembrane receptor comprising the amino acid sequence in SEQ ID NO: 28.

13. A purified and isolated V28 seven transmembrane receptor fragment selected from the group consisting of the N-terminal extracellular domain of V28, transmembrane domains of V28, extracellular loops connecting transmembrane domains of V28, intracellular loops connecting transmembrane domains of V28, the C-terminal cytoplasmic domain of V28, and fusions thereof.

14. A purified and isolated polypeptide comprising the N-terminal extracellular domain of V28.

15. A purified and isolated polypeptide comprising at least one extracellular domain of V28.

16. A purified and isolated polynucleotide comprising a continuous portion of SEQ ID NO: 27, said continuous portion encoding the amino acid sequence of a V28 seven transmembrane receptor fragment, said fragment selected from the group consisting of the N-terminal extracellular domain of V28, transmembrane domains of V28, extracellular loops connecting transmembrane domains of V28, intracellular loops connecting transmembrane domains of V28, the C-terminal cytoplasmic domain of V28, and fusions thereof.

17. The polynucleotide of claim 16 which is a DNA.

18. A DNA according to claim 17 wherein said continuous portion of SEQ ID NO: 27 encodes the amino acid sequence of the N-terminal extracellular domain of V28.

19. A DNA according to claim 17 wherein said continuous portion of SEQ ID NO: 27 encodes the amino acid sequence of an extracellular loop connecting transmembrane domains of V28.

20. A DNA vector comprising a DNA according to claim 17, 18, or 19.

21. A host cell transformed or transfected with a DNA according to claim 17, 18, or 19.

22. A method for producing a recombinant polypeptide comprising the steps of growing a host cell in a suitable medium and isolating said recombinant polypeptide from said cell or said medium, wherein said host cell is a host cell transformed or transfected with a DNA comprising a continuous portion of SEQ ID NO: 27, said continuous portion encoding a V28 seven transmembrane receptor fragment said fragment selected from the group consisting of the N-terminal extracellular domain of V28, transmembrane domains of V28, extracellular loops connecting transmembrane domains of V28, intracellular loops connecting transmembrane domains of V28, the C-terminal cytoplasmic domain of V28, and fusions thereof.

23. A method according to claim 22 wherein said host cell is transformed or transfected with a DNA comprising a continuous portion of SEQ ID NO: 27 that encodes the N-terminal extracellular domain of V28.

24. A method according to claim 22 it wherein said host cell is transformed or transfected with a DNA comprising a continuous portion of SEQ ID NO: 27 that encodes an extracellular loop connecting transmembrane domains of V28.

25. A purified and isolated polynucleotide having a nucleotide sequence comprising a continuous portion of at least 114 nucleotides of SEQ ID NO: 27.

26. A purified and isolated polynucleotide according to claim 25, further comprising a detectable label.

* * * * *

UNITED STATES PATENT AND TRADEMARK OFFICE
CERTIFICATE OF CORRECTION

PATENT NO. : 5,759,804
DATED : June 2, 1998
INVENTOR(S) : Godiska et al.

Figure 1B:
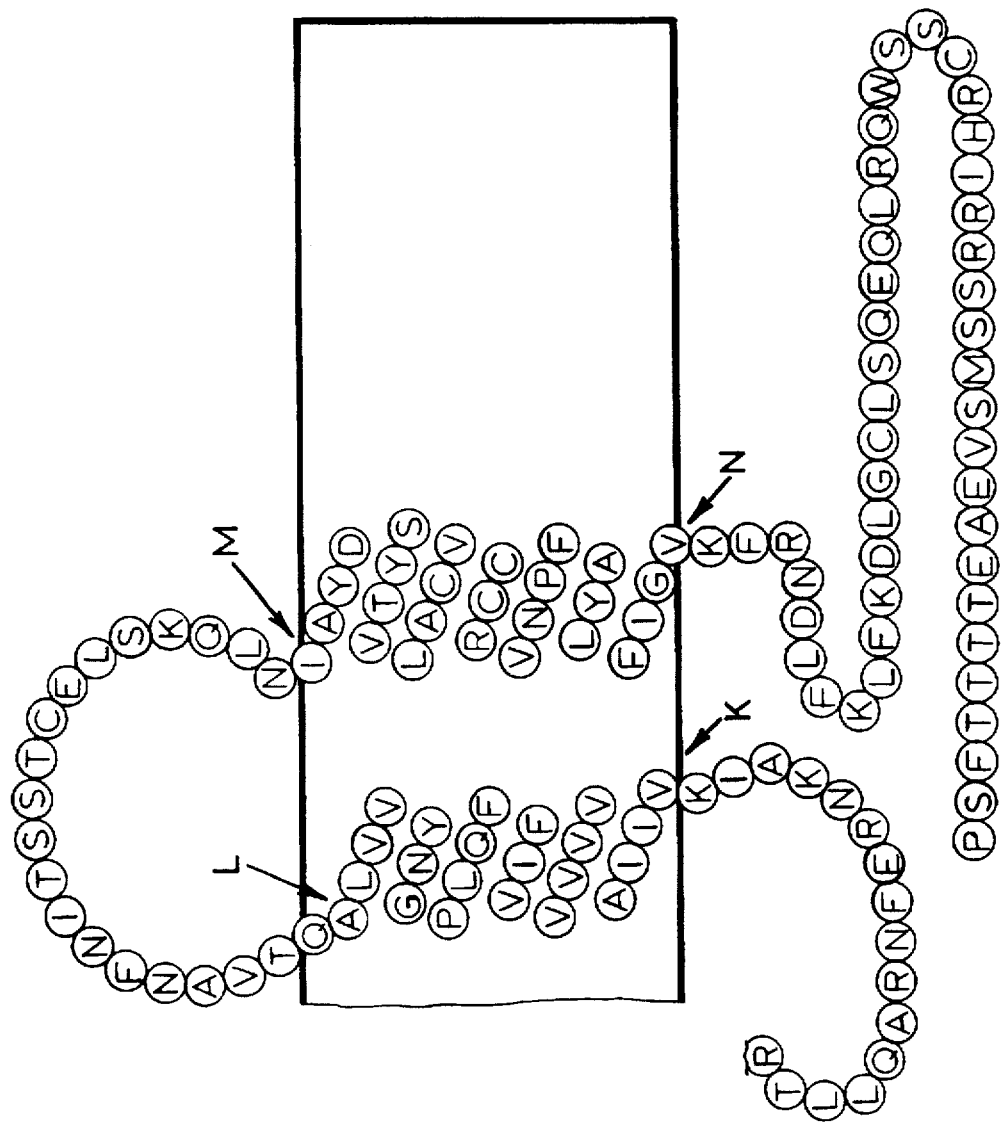

It is certified that error appears in the above-identified patent and that said Letters Patent is hereby corrected as shown below:

Column 5,
Line 11, delete "The FIGURE is" and insert -- Figures 1A and 1B (referred to herein collectively as Figure 1) are --

Column 6,
Line 21, delete "GAC GGA TCC GTT TTT CTG TTG AAT TTG GCT" and insert
-- GAC GGA TCC GTT TTT CTG TTG AAT TTG GCT --.
Line 40, delete "GGC TAA GCT TGI ACI ATI GC(Y or I) AGR TAI CGR" and insert
-- GGC TAA GCT TGI ACI GC(Y or I) AGR TAI CGR --.

Column 8,
Line 9, delete "533" and insert -- 5X --.

Column 9,
Line 1, delete "GGTGAATTCAGGCTTTAAAGTTCCGCAC" and insert
-- GGTGAATTCAGGCTTTAAAGTTCCGCAC --.
Line 13, delete "32P-labelled" and insert -- $^{32}$P-labelled --.

Column 11,
Line 14, delete "32P" and insert -- $^{32}$P --.
Line 18, delete "32P-dCTP" and insert -- $^{32}$P-dCTP --.

Column 17,
Line 63, delete "Chomezynski" and insert -- Chomczynski --.

Column 101,
Line 39, after "synthesized" insert -- DNA --.
Line 56, delete "ATTC" and insert -- ATCC --.

UNITED STATES PATENT AND TRADEMARK OFFICE
CERTIFICATE OF CORRECTION

PATENT NO. : 5,759,804
DATED : June 2, 1998
INVENTOR(S) : Godiska et al.

It is certified that error appears in the above-identified patent and that said Letters Patent is hereby corrected as shown below:

Column 103,
Line 4, after "suitable" insert -- nutrient --.
Line 9, after "encoding" insert -- a polypeptide which is --.
Line 9, delete "fragment" and insert -- fragment, --.

Signed and Sealed this

Seventeenth Day of September, 2002

*Attest:*

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

GACGGATCCG TTTTCTGTT GAATTGGCT CTGGCTGACY TAYKCTTTKY MCTGACYTTG    60

CCMMTSTGG    69

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: modified_base
        ( B ) LOCATION: 12
        ( D ) OTHER INFORMATION: /note="The modified base at this
            position is an inosine."

( i x ) FEATURE:
        ( A ) NAME/KEY: modified_base
        ( B ) LOCATION: 15
        ( D ) OTHER INFORMATION: /note="The modified base at this
            position is an inosine."

( i x ) FEATURE:
        ( A ) NAME/KEY: modified_base
        ( B ) LOCATION: 18
        ( D ) OTHER INFORMATION: /note="The modified base at this
            position is an inosine."

( i x ) FEATURE:
        ( A ) NAME/KEY: misc_difference
        ( B ) LOCATION: replace(21, "")
        ( D ) OTHER INFORMATION: /note="The nucleotide at this
            position may also be an inosine."

( i x ) FEATURE:
        ( A ) NAME/KEY: modified_base
        ( B ) LOCATION: 27
        ( D ) OTHER INFORMATION: /note="The modified base at this
            position is an inosine."

( x i ) SEQUENCE DESCRIPTION: SEQ ID NO:2:

GGCTAAGCTT GNACNATNGC YAGRTANCGR TC    32

( 2 ) INFORMATION FOR SEQ ID NO:3:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (genomic)

-continued ( x i ) SEQUENCE DESCRIPTION: SEQ ID NO:3:

| | | | | | |
|---|---|---|---|---|---|
| GTGGATAAAG | AAGCATCTCT | AGGACTGTGG | AGGACGGGCT | CCTTCCTGTG | CAAAGGGAGC | 60 |
| TCCTACATGA | TCTCCGTCAA | TATGCACTGC | AGTGTCCTCC | TGCTCACTTG | CATGAGTGTT | 120 |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TGGGCCTACA GCGCGGCCAA                                                                                                                 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TCAATGCTGA TGCAAAGAAG                                                                                                                 20

( 2 ) INFORMATION FOR SEQ ID NO:6:

( i ) SEQUENCE CHARACTERISTICS:
        ( A ) LENGTH: 2058 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 166..1395

( x i ) SEQUENCE DESCRIPTION: SEQ ID NO:6:

| | | | | | |
|---|---|---|---|---|---|
| GATGAACCAC | TATTCCTCCG | CCTGGGCAAC | ATGGCAGAAT | CCCATCTCTA | CTAAAAATAC | 60 |
| AAAAATTCGC | TGGGGTGTGG | TGGCATAAGG | CTGTGGTCCC | AGCTACTCAG | GAGGCTGAAG | 120 |
| TGGAAGGATC | ACCTGAGCCT | GGAGAGGCCG | AGGCTGCAGG | GAGCC ATG ATT GCA | | 174 |
| | | | | Met Ile Ala | |
| | | | | 1 | |

| CCA | CTG | CAC | TCC | AGC | CTG | GGC | AAC | AGA | GTG | AGA | CCA | TGT | CTC | AAG | AAA | 222 |
|---|---|---|---|---|---|---|---|---|---|---|---|---|---|---|---|---|
| Pro | Leu | His | Ser | Ser | Leu | Gly | Asn | Arg | Val | Arg | Pro | Cys | Leu | Lys | Lys | |
| | 5 | | | | 10 | | | | | 15 | | | | | | |

| AAA | AAA | AAA | GAA | AGA | AAC | CAC | TGC | TCT | AGG | CTA | AAT | CCC | AGC | CAG | AGT | 270 |
|---|---|---|---|---|---|---|---|---|---|---|---|---|---|---|---|---|
| Lys | Lys | Lys | Glu | Arg | Asn | His | Cys | Ser | Arg | Leu | Asn | Pro | Ser | Gln | Ser | |
| 20 | | | | | 25 | | | | 30 | | | | | | 35 | |

| TGG | AGC | CAC | CCA | GCT | AAA | CTG | GCC | TGT | TTT | CCC | TCA | TTT | CCT | TCC | CCG | 318 |
|---|---|---|---|---|---|---|---|---|---|---|---|---|---|---|---|---|
| Trp | Ser | His | Pro | Ala | Lys | Leu | Ala | Cys | Phe | Pro | Ser | Phe | Pro | Ser | Pro | |
| | | | 40 | | | | | 45 | | | | | 50 | | | |

| AAG | GTA | TGC | CTG | TGT | CAA | GAT | GAG | GTC | ACG | GAC | GAT | TAC | ATC | GGA | GAC | 366 |
|---|---|---|---|---|---|---|---|---|---|---|---|---|---|---|---|---|
| Lys | Val | Cys | Leu | Cys | Gln | Asp | Glu | Val | Thr | Asp | Asp | Tyr | Ile | Gly | Asp | |
| | | | 55 | | | | | 60 | | | | | 65 | | | |

| AAC | ACC | ACA | GTG | GAC | TAC | ACT | TTG | TTC | GAG | TCT | TTG | TGC | TCC | AAG | AAG | 414 |
|---|---|---|---|---|---|---|---|---|---|---|---|---|---|---|---|---|
| Asn | Thr | Thr | Val | Asp | Tyr | Thr | Leu | Phe | Glu | Ser | Leu | Cys | Ser | Lys | Lys | |
| | 70 | | | | | 75 | | | | | 80 | | | | | |

| | | | | | | | | | | | | | | | | |
|---|---|---|---|---|---|---|---|---|---|---|---|---|---|---|---|---|
| GAC | GTG | CGG | AAC | TTT | AAA | GCC | TGG | TTC | CTC | CCT | ATC | ATG | TAC | TCC | ATC | 462 |
| Asp | Val 85 | Arg | Asn | Phe | Lys 90 | Ala | Trp | Phe | Leu | Pro | Ile 95 | Met | Tyr | Ser | Ile | |
| ATT | TGT | TTC | GTG | GGC | CTA | CTG | GGC | AAT | GGG | CTG | GTC | GTG | TTG | ACC | TAT | 510 |
| Ile 100 | Cys | Phe | Val | Gly | Leu 105 | Leu | Gly | Asn | Gly | Leu 110 | Val | Val | Leu | Thr | Tyr 115 | |
| ATC | TAT | TTC | AAG | AGG | CTC | AAG | ACC | ATG | ACC | GAT | ACC | TAC | CTG | CTC | AAC | 558 |
| Ile | Tyr | Phe | Lys | Arg 120 | Leu | Lys | Thr | Met | Thr 125 | Asp | Thr | Tyr | Leu | Leu 130 | Asn | |
| CTG | GCG | GTG | GCA | GAC | ATC | CTC | TTC | CTC | CTG | ACC | CTT | CCC | TTC | TGG | GCC | 606 |
| Leu | Ala | Val | Ala 135 | Asp | Ile | Leu | Phe | Leu 140 | Leu | Thr | Leu | Pro | Phe 145 | Trp | Ala | |
| TAC | AGC | GCG | GCC | AAG | TCC | TGG | GTC | TTC | GGT | GTC | CAC | TTT | TGC | AAG | CTC | 654 |
| Tyr | Ser | Ala 150 | Ala | Lys | Ser | Trp | Val 155 | Phe | Gly | Val | His | Phe 160 | Cys | Lys | Leu | |
| ATC | TTT | GCC | ATC | TAC | AAG | ATG | AGC | TTC | TTC | AGT | GGC | ATG | CTC | CTA | CTT | 702 |
| Ile | Phe 165 | Ala | Ile | Tyr | Lys | Met 170 | Ser | Phe | Phe | Ser | Gly 175 | Met | Leu | Leu | Leu | |
| CTT | TGC | ATC | AGC | ATT | GAC | CGC | TAC | GTG | GCC | ATC | GTC | CAG | GCT | GTC | TCA | 750 |
| Leu 180 | Cys | Ile | Ser | Ile | Asp 185 | Arg | Tyr | Val | Ala | Ile 190 | Val | Gln | Ala | Val | Ser 195 | |
| GCT | CAC | CGC | CAC | CGT | GCC | CGC | GTC | CTT | CTC | ATC | AGC | AAG | CTG | TCC | TGT | 798 |
| Ala | His | Arg | His | Arg 200 | Ala | Arg | Val | Leu | Leu 205 | Ile | Ser | Lys | Leu | Ser 210 | Cys | |
| GTG | GGC | ATC | TGG | ATA | CTA | GCC | ACA | GTG | CTC | TCC | ATC | CCA | GAG | CTC | CTG | 846 |
| Val | Gly | Ile | Trp 215 | Ile | Leu | Ala | Thr | Val 220 | Leu | Ser | Ile | Pro | Glu 225 | Leu | Leu | |
| TAC | AGT | GAC | CTC | CAG | AGG | AGC | AGC | AGT | GAG | CAA | GCG | ATG | CGA | TGC | TCT | 894 |
| Tyr | Ser | Asp 230 | Leu | Gln | Arg | Ser | Ser 235 | Ser | Glu | Gln | Ala | Met 240 | Arg | Cys | Ser | |
| CTC | ATC | ACA | GAG | CAT | GTG | GAG | GCC | TTT | ATC | ACC | ATC | CAG | GTG | GCC | CAG | 942 |
| Leu | Ile | Thr | Glu 245 | His | Val | Glu | Ala | Phe 250 | Ile | Thr | Ile | Gln | Val 255 | Ala | Gln | |
| ATG | GTG | ATC | GGC | TTT | CTG | GTC | CCC | CTG | CTG | GCC | ATG | AGC | TTC | TGT | TAC | 990 |
| Met 260 | Val | Ile | Gly | Phe | Leu 265 | Val | Pro | Leu | Leu | Ala 270 | Met | Ser | Phe | Cys | Tyr 275 | |
| CTT | GTC | ATC | ATC | CGC | ACC | CTG | CTC | CAG | GCA | CGC | AAC | TTT | GAG | CGC | AAC | 1038 |
| Leu | Val | Ile | Ile | Arg 280 | Thr | Leu | Leu | Gln | Ala 285 | Arg | Asn | Phe | Glu | Arg 290 | Asn | |
| AAG | GCC | ATC | AAG | GTG | ATC | ATC | GCT | GTG | GTC | GTG | GTC | TTC | ATA | GTC | TTC | 1086 |
| Lys | Ala | Ile | Lys 295 | Val | Ile | Ile | Ala | Val 300 | Val | Val | Val | Phe | Ile 305 | Val | Phe | |
| CAG | CTG | CCC | TAC | AAT | GGG | GTG | GTC | CTG | GCC | CAG | ACG | GTG | GCC | AAC | TTC | 1134 |
| Gln | Leu | Pro 310 | Tyr | Asn | Gly | Val | Val 315 | Leu | Ala | Gln | Thr | Val 320 | Ala | Asn | Phe | |
| AAC | ATC | ACC | AGT | AGC | ACC | TGT | GAG | CTC | AGT | AAG | CAA | CTC | AAC | ATC | GCC | 1182 |
| Asn | Ile 325 | Thr | Ser | Ser | Thr | Cys 330 | Glu | Leu | Ser | Lys | Gln 335 | Leu | Asn | Ile | Ala | |
| TAC | GAC | GTC | ACC | TAC | AGC | CTG | GCC | TGC | GTC | CGC | TGC | TGC | GTC | AAC | CCT | 1230 |
| Tyr | Asp | Val | Thr 340 | Tyr | Ser | Leu | Ala | Cys 345 | Val | Arg | Cys | Cys | Val 350 | Asn | Pro 355 | |
| TTC | TTG | TAC | GCC | TTC | ATC | GGC | GTC | AAG | TTC | CGC | AAC | GAT | CTC | TTC | AAG | 1278 |
| Phe | Leu | Tyr | Ala | Phe 360 | Ile | Gly | Val | Lys | Phe 365 | Arg | Asn | Asp | Leu | Phe 370 | Lys | |
| CTC | TTC | AAG | GAC | CTG | GGC | TGC | CTC | AGC | CAG | GAG | CAG | CTC | CGG | CAG | TGG | 1326 |
| Leu | Phe | Lys | Asp 375 | Leu | Gly | Cys | Leu | Ser 380 | Gln | Glu | Gln | Leu | Arg 385 | Gln | Trp | |
| TCT | TCC | TGT | CGG | CAC | ATC | CGG | CGC | TCC | TCC | ATG | AGT | GTG | GAG | GCC | GAG | 1374 |
| Ser | Ser | Cys | Arg | His 390 | Ile | Arg | Arg | Ser | Ser 395 | Met | Ser | Val | Glu | Ala 400 | Glu | |

```
ACC ACC ACC ACC TTC TCC CCA TAGGCGACTC TTCTGCCTGG ACTAGAGGGA        1425
Thr Thr Thr Thr Phe Ser Pro
        405              410

CCTCTCCCAG GGTCCCTGGG GCGGGGATAG GGAGNAGATG CAATGACTCA GGACATCCCC   1485

CCGCCAAAAG CTGCTCAGGG AAAAGCAGCT CTCCCCTCAG AGTGCAAGCC CTGCTCCAGA   1545

AGTTAGCTTC ACCCCAATCC CAGCTACCTC AACCAATGCC GAAAAGACA GGGCTGATAA    1605

GCTAACACCA GACAGACAAC ACTGGGAAAC AGAGGCTATT GTCCCTAAA CCAAAAACTG    1665

AAAGTGAAAG TCCAGAAACT GTTCCCACCT GCTGGAGTGA AGGGGCCAAG GAGGGTGAGT   1725

GCAAGGGGCN GTGGGAGTGG CCTGAAGAGT CCTCTGAATG AACCTTCTGG CCTCCCACAG   1785

ACTCAAATGC TCAGACCAGC TCTTCCGAAA ACCAGGCCTT ATCTCCAAGA CCAGAGATAG   1845

TGGGGAGACT TCTTGGCTTG GTGAGGAAAA GCGGACATCA GCAGCTGGTC AAACAAACTC   1905

TCTGAACCCC TCCCTCCATC GTTTCTTCA CTGTCCTCCA AGCCAGCGGG AATGCAGCTG    1965

CCACGCCGCC CTAAAAGCAC ACTCATCCCC TCACTTGCCG CGTCGCCCTC CCAGGCTCTC   2025

AACAGGGGAG AGTGTGGTGT TTCCTTCCTG CAG                                2058
```

( 2 ) INFORMATION FOR SEQ ID NO:7:

( i ) SEQUENCE CHARACTERISTICS:
( A ) LENGTH: 410 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Ile Ala Pro Leu His Ser Ser Leu Gly Asn Arg Val Arg Pro Cys
  1               5                  10                  15

Leu Lys Lys Lys Lys Glu Arg Asn His Cys Ser Arg Leu Asn Pro
             20                  25                  30

Ser Gln Ser Trp Ser His Pro Ala Lys Leu Ala Cys Phe Pro Ser Phe
         35                  40                  45

Pro Ser Pro Lys Val Cys Leu Cys Gln Asp Glu Val Thr Asp Asp Tyr
     50                  55                  60

Ile Gly Asp Asn Thr Thr Val Asp Tyr Thr Leu Phe Glu Ser Leu Cys
 65                  70                  75                  80

Ser Lys Lys Asp Val Arg Asn Phe Lys Ala Trp Phe Leu Pro Ile Met
                 85                  90                  95

Tyr Ser Ile Ile Cys Phe Val Gly Leu Leu Gly Asn Gly Leu Val Val
                100                 105                 110

Leu Thr Tyr Ile Tyr Phe Lys Arg Leu Lys Thr Met Thr Asp Thr Tyr
             115                 120                 125

Leu Leu Asn Leu Ala Val Ala Asp Ile Leu Phe Leu Leu Thr Leu Pro
         130                 135                 140

Phe Trp Ala Tyr Ser Ala Ala Lys Ser Trp Val Phe Gly Val His Phe
145                 150                 155                 160

Cys Lys Leu Ile Phe Ala Ile Tyr Lys Met Ser Phe Phe Ser Gly Met
                165                 170                 175

Leu Leu Leu Leu Cys Ile Ser Ile Asp Arg Tyr Val Ala Ile Val Gln
                180                 185                 190

Ala Val Ser Ala His Arg His Arg Ala Arg Val Leu Leu Ile Ser Lys
             195                 200                 205

Leu Ser Cys Val Gly Ile Trp Ile Leu Ala Thr Val Leu Ser Ile Pro
         210                 215                 220
```

| Glu<br>225 | Leu | Leu | Tyr | Ser | Asp<br>230 | Leu | Gln | Arg | Ser<br>235 | Ser | Glu | Gln | Ala | Met<br>240 |
|---|---|---|---|---|---|---|---|---|---|---|---|---|---|---|
| Arg | Cys | Ser | Leu | Ile<br>245 | Thr | Glu | His | Val | Glu<br>250 | Ala | Phe | Ile | Thr | Ile<br>255 | Gln |
| Val | Ala | Gln | Met<br>260 | Val | Ile | Gly | Phe | Leu<br>265 | Val | Pro | Leu | Leu<br>270 | Ala | Met | Ser |
| Phe | Cys | Tyr<br>275 | Leu | Val | Ile | Ile | Arg<br>280 | Thr | Leu | Leu | Gln<br>285 | Ala | Arg | Asn | Phe |
| Glu | Arg<br>290 | Asn | Lys | Ala | Ile<br>295 | Lys | Val | Ile | Ile | Ala<br>300 | Val | Val | Val | Val | Phe |
| Ile<br>305 | Val | Phe | Gln | Leu | Pro<br>310 | Tyr | Asn | Gly | Val | Val<br>315 | Leu | Ala | Gln | Thr | Val<br>320 |
| Ala | Asn | Phe | Asn | Ile<br>325 | Thr | Ser | Ser | Thr | Cys<br>330 | Glu | Leu | Ser | Lys | Gln<br>335 | Leu |
| Asn | Ile | Ala | Tyr<br>340 | Asp | Val | Thr | Tyr | Ser<br>345 | Leu | Ala | Cys | Val | Arg<br>350 | Cys | Cys |
| Val | Asn | Pro<br>355 | Phe | Leu | Tyr | Ala | Phe<br>360 | Ile | Gly | Val | Lys | Phe<br>365 | Arg | Asn | Asp |
| Leu | Phe<br>370 | Lys | Leu | Phe | Lys | Asp<br>375 | Leu | Gly | Cys | Leu | Ser<br>380 | Gln | Glu | Gln | Leu |
| Arg<br>385 | Gln | Trp | Ser | Ser | Cys<br>390 | Arg | His | Ile | Arg<br>395 | Arg | Ser | Ser | Met | Ser | Val<br>400 |
| Glu | Ala | Glu | Thr | Thr<br>405 | Thr | Thr | Phe | Ser | Pro<br>410 |

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGTGAATTCA GGCTTTAAAG TTCCGCAC        28

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GCAGAACTGG TAGGTATGGA        20

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GTATGCCTGT GTCAAGATGA GGTCACGGAC GATTACATCG GAGACAACAC CACAGTGGAC 60

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TTAAAGTTCC GCACGTCCTT CTTGGAGCAC AAAGACTCGA ACAAAGTGTA GTCCACTGTG 60

( 2 ) INFORMATION FOR SEQ ID NO:12:

( i ) SEQUENCE CHARACTERISTICS:
        ( A ) LENGTH: 238 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GAATTCTGCG AGGCCGGGCA CAGCCTTCCT GTGTGGTTTT ACCGCCCAGA GAGCGTCATG 60
GACCTGGGGA AACCAATGAA AAGCGTGCTG GTGGTGGCTC TCCTTGTCAT TTTCCAGGTA 120
TGCCTGTGTC AAGATGAGGT CACGGACGAT TACATCGGAG ACAACACCAC AGTGGACTAC 180
ACTTTGTTCG AGTCTTTGTG CTCCAAGAAG GACGTGCGGA ACTTTAAAGC CTGAATTC 238

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GCACAGCCTT CCTGTGTGG 19

( 2 ) INFORMATION FOR SEQ ID NO:14:

( i ) SEQUENCE CHARACTERISTICS:
        ( A ) LENGTH: 2160 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 64..1197

( x i ) SEQUENCE DESCRIPTION: SEQ ID NO:14:

```
AGACAGGGGT AGTGCGAGGC CGGGCACAGC CTTCCTGTGT GGTTTTACCG CCCAGAGAGC          60

GTC ATG GAC CTG GGG AAA CCA ATG AAA AGC GTG CTG GTG GTG GCT CTC          108
    Met Asp Leu Gly Lys Pro Met Lys Ser Val Leu Val Val Ala Leu
    1               5                   10                  15

CTT GTC ATT TTC CAG GTA TGC CTG TGT CAA GAT GAG GTC ACG GAC GAT          156
Leu Val Ile Phe Gln Val Cys Leu Cys Gln Asp Glu Val Thr Asp Asp
                20              25                  30
```

| | | | | | | | | | | | | | | | | |
|---|---|---|---|---|---|---|---|---|---|---|---|---|---|---|---|---|
| TAC | ATC | GGA | GAC | AAC | ACC | ACA | GTG | GAC | TAC | ACT | TTG | TTC | GAG | TCT | TTG | 204 |
| Tyr | Ile | Gly | Asp 35 | Asn | Thr | Thr | Val 40 | Asp | Tyr | Thr | Leu | Phe | Glu 45 | Ser | Leu | |
| TGC | TCC | AAG | AAG | GAC | GTG | CGG | AAC | TTT | AAA | GCC | TGG | TTC | CTC | CCT | ATC | 252 |
| Cys | Ser | Lys 50 | Lys | Asp | Val | Arg | Asn 55 | Phe | Lys | Ala | Trp | Phe 60 | Leu | Pro | Ile | |
| ATG | TAC | TCC | ATC | ATT | TGT | TTC | GTG | GGC | CTA | CTG | GGC | AAT | GGG | CTG | GTC | 300 |
| Met | Tyr 65 | Ser | Ile | Ile | Cys | Phe 70 | Val | Gly | Leu | Leu | Gly 75 | Asn | Gly | Leu | Val | |
| GTG | TTG | ACC | TAT | ATC | TAT | TTC | AAG | AGG | CTC | AAG | ACC | ATG | ACC | GAT | ACC | 348 |
| Val | Leu 80 | Thr | Tyr | Ile | Tyr 85 | Phe | Lys | Arg | Leu | Lys 90 | Thr | Met | Thr | Asp | Thr 95 | |
| TAC | CTG | CTC | AAC | CTG | GCG | GTG | GCA | GAC | ATC | CTC | TTC | CTC | CTG | ACC | CTT | 396 |
| Tyr | Leu | Leu | Asn 100 | Leu | Ala | Val | Ala | Asp 105 | Ile | Leu | Phe | Leu | Leu 110 | Thr | Leu | |
| CCC | TTC | TGG | GCC | TAC | AGC | GCG | GCC | AAG | TCC | TGG | GTC | TTC | GGT | GTC | CAC | 444 |
| Pro | Phe | Trp | Ala 115 | Tyr | Ser | Ala | Ala | Lys 120 | Ser | Trp | Val | Phe | Gly 125 | Val | His | |
| TTT | TGC | AAG | CTC | ATC | TTT | GCC | ATC | TAC | AAG | ATG | AGC | TTC | TTC | AGT | GGC | 492 |
| Phe | Cys | Lys 130 | Leu | Ile | Phe | Ala | Ile 135 | Tyr | Lys | Met | Ser | Phe 140 | Phe | Ser | Gly | |
| ATG | CTC | CTA | CTT | CTT | TGC | ATC | AGC | ATT | GAC | CGC | TAC | GTG | GCC | ATC | GTC | 540 |
| Met | Leu 145 | Leu | Leu | Leu | Cys | Ile 150 | Ser | Ile | Asp | Arg | Tyr 155 | Val | Ala | Ile | Val | |
| CAG | GCT | GTC | TCA | GCT | CAC | CGC | CAC | CGT | GCC | CGC | GTC | CTT | CTC | ATC | AGC | 588 |
| Gln 160 | Ala | Val | Ser | Ala | His 165 | Arg | His | Arg | Ala | Arg 170 | Val | Leu | Leu | Ile | Ser 175 | |
| AAG | CTG | TCC | TGT | GTG | GGC | ATC | TGG | ATA | CTA | GCC | ACA | GTG | CTC | TCC | ATC | 636 |
| Lys | Leu | Ser | Cys | Val 180 | Gly | Ile | Trp | Ile | Leu 185 | Ala | Thr | Val | Leu | Ser 190 | Ile | |
| CCA | GAG | CTC | CTG | TAC | AGT | GAC | CTC | CAG | AGG | AGC | AGC | AGT | GAG | CAA | GCG | 684 |
| Pro | Glu | Leu | Leu 195 | Tyr | Ser | Asp | Leu | Gln 200 | Arg | Ser | Ser | Ser | Glu 205 | Gln | Ala | |
| ATG | CGA | TGC | TCT | CTC | ATC | ACA | GAG | CAT | GTG | GAG | GCC | TTT | ATC | ACC | ATC | 732 |
| Met | Arg | Cys 210 | Ser | Leu | Ile | Thr | Glu 215 | His | Val | Glu | Ala | Phe 220 | Ile | Thr | Ile | |
| CAG | GTG | GCC | CAG | ATG | GTG | ATC | GGC | TTT | CTG | GTC | CCC | CTG | CTG | GCC | ATG | 780 |
| Gln | Val | Ala | Gln 225 | Met | Val | Ile | Gly | Phe 230 | Leu | Val | Pro | Leu | Leu 235 | Ala | Met | |
| AGC | TTC | TGT | TAC | CTT | GTC | ATC | ATC | CGC | ACC | CTG | CTC | CAG | GCA | CGC | AAC | 828 |
| Ser 240 | Phe | Cys | Tyr | Leu | Val 245 | Ile | Ile | Arg | Thr | Leu 250 | Leu | Gln | Ala | Arg | Asn 255 | |
| TTT | GAG | CGC | AAC | AAG | GCC | ATC | AAG | GTG | ATC | ATC | GCT | GTG | GTC | GTG | GTC | 876 |
| Phe | Glu | Arg | Asn | Lys 260 | Ala | Ile | Lys | Val | Ile 265 | Ile | Ala | Val | Val | Val 270 | Val | |
| TTC | ATA | GTC | TTC | CAG | CTG | CCC | TAC | AAT | GGG | GTG | GTC | CTG | GCC | CAG | ACG | 924 |
| Phe | Ile | Val | Phe 275 | Gln | Leu | Pro | Tyr | Asn 280 | Gly | Val | Val | Leu | Ala 285 | Gln | Thr | |
| GTG | GCC | AAC | TTC | AAC | ATC | ACC | AGT | AGC | ACC | TGT | GAG | CTC | AGT | AAG | CAA | 972 |
| Val | Ala | Asn | Phe 290 | Asn | Ile | Thr | Ser | Ser 295 | Thr | Cys | Glu | Leu | Ser 300 | Lys | Gln | |
| CTC | AAC | ATC | GCC | TAC | GAC | GTC | ACC | TAC | AGC | CTG | GCC | TGC | GTC | CGC | TGC | 1020 |
| Leu | Asn | Ile 305 | Ala | Tyr | Asp | Val | Thr 310 | Tyr | Ser | Leu | Ala | Cys 315 | Val | Arg | Cys | |
| TGC | GTC | AAC | CCT | TTC | TTG | TAC | GCC | TTC | ATC | GGC | GTC | AAG | TTC | CGC | AAC | 1068 |
| Cys 320 | Val | Asn | Pro | Phe | Leu 325 | Tyr | Ala | Phe | Ile | Gly 330 | Val | Lys | Phe | Arg | Asn 335 | |
| GAT | CTC | TTC | AAG | CTC | TTC | AAG | GAC | CTG | GGC | TGC | CTC | AGC | CAG | GAG | CAG | 1116 |
| Asp | Leu | Phe | Lys | Leu 340 | Phe | Lys | Asp | Leu | Gly 345 | Cys | Leu | Ser | Gln | Glu 350 | Gln | |

-continued

| | | | | | | | | | | | | | | | | |
|---|---|---|---|---|---|---|---|---|---|---|---|---|---|---|---|---|
| CTC | CGG | CAG | TGG | TCT | TCC | TGT | CGG | CAC | ATC | CGG | CGC | TCC | TCC | ATG | AGT | 1164 |
| Leu | Arg | Gln | Trp<br>355 | Ser | Ser | Cys | Arg | His<br>360 | Ile | Arg | Arg | Ser | Ser<br>365 | Met | Ser | |
| GTG | GAG | GCC | GAG | ACC | ACC | ACC | ACC | TTC | TCC | CCA | TAGGCGACTC | | | TTCTGCCTGG | | 1217 |
| Val | Glu | Ala<br>370 | Glu | Thr | Thr | Thr | Thr<br>375 | Phe | Ser | Pro | | | | | | |

| | | | | |
|---|---|---|---|---|
| ACTAGAGGGA | CCTCTCCCAG | GGTCCCTGGG | GTGGGGATAG | GGAGCAGATG | CAATGACTCA | 1277 |
| GGACATCCCC | CCGCCAAAAG | CTGCTCAGGG | AAAAGCAGCT | CTCCCCTCAG | AGTGCAAGCC | 1337 |
| CTGCTCCAGA | AGTTAGCTTC | ACCCCAATCC | CAGCTACCTC | AACCAATGCC | GAAAAAGACA | 1397 |
| GGGCTGATAA | GCTAACACCA | GACAGACAAC | ACTGGGAAAC | AGAGGCTATT | GTCCCCTAAA | 1457 |
| CCAAAAACTG | AAAGTGAAAG | TCCAGAAACT | GTTCCCACCT | GCTGGAGTGA | AGGGGCCAAG | 1517 |
| GAGGGTGAGT | GCAAGGGGCG | TGGGAGTGGC | CTGAAGAGTC | CTCTGAATGA | ACCTTCTGGC | 1577 |
| CTCCCACAGA | CTCAAATGCT | CAGACCAGCT | CTTCCGAAAA | CCAGGCCTTA | TCTCCAAGAC | 1637 |
| CAGAGATAGT | GGGGAGACTT | CTTGGCTTGG | TGAGGAAAAG | CGGACATCAG | CAGCTGGTCA | 1697 |
| AACAAACTCT | CTGAACCCCT | CCCTCCATCG | TTTTCTTCAC | TGTCCTCCAA | GCCAGCGGGA | 1757 |
| ATGCAGCTGC | CACGCCGCCC | TAAAAGCACA | CTCATCCCCT | CACTTGCCGC | GTCGCCCTCC | 1817 |
| CAGGCTCTCA | ACAGGGAGA | GTGTGGTGTT | TCCTGCAGGC | CAGGCCAGCT | GCCTCCGCGT | 1877 |
| GATCAAAGCC | ACACTCTGGG | CTCCAGAGTG | GGGATGACAT | GCACTCAGCT | CTTGGCTCCA | 1937 |
| CTGGGATGGG | AGGAGAGGAC | AAGGGAAATG | TCAGGGGCGG | GGAGGGTGAC | AGTGGCCGCC | 1997 |
| CAAGGCCCAC | GAGCTTGTTC | TTTGTTCTTT | GTCACAGGGA | CTGAAAACCT | CTCCTCATGT | 2057 |
| TCTGCTTTCG | ATTCGTTAAG | AGAGCAACAT | TTTACCCACA | CACAGATAAA | GTTTCCCTT | 2117 |
| GAGGAAACAA | CAGCTTTAAA | AGAAAAAAA | AAAAAAGAA | TTC | | 2160 |

( 2 ) INFORMATION FOR SEQ ID NO:15:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| Met<br>1 | Asp | Leu | Gly | Lys<br>5 | Pro | Met | Lys | Ser | Val<br>10 | Leu | Val | Val | Ala | Leu<br>15 | Leu |
|---|---|---|---|---|---|---|---|---|---|---|---|---|---|---|---|
| Val | Ile | Phe | Gln<br>20 | Val | Cys | Leu | Cys | Gln<br>25 | Asp | Glu | Val | Thr | Asp<br>30 | Asp | Tyr |
| Ile | Gly | Asp<br>35 | Asn | Thr | Thr | Val | Asp<br>40 | Tyr | Thr | Leu | Phe | Glu<br>45 | Ser | Leu | Cys |
| Ser | Lys<br>50 | Lys | Asp | Val | Arg | Asn<br>55 | Phe | Lys | Ala | Trp | Phe<br>60 | Leu | Pro | Ile | Met |
| Tyr<br>65 | Ser | Ile | Ile | Cys | Phe<br>70 | Val | Gly | Leu | Leu | Gly<br>75 | Asn | Gly | Leu | Val | Val<br>80 |
| Leu | Thr | Tyr | Ile | Tyr<br>85 | Phe | Lys | Arg | Leu | Lys<br>90 | Thr | Met | Thr | Asp | Thr<br>95 | Tyr |
| Leu | Leu | Asn | Leu<br>100 | Ala | Val | Ala | Asp | Ile<br>105 | Leu | Phe | Leu | Leu | Thr<br>110 | Leu | Pro |
| Phe | Trp | Ala<br>115 | Tyr | Ser | Ala | Ala | Lys<br>120 | Ser | Trp | Val | Phe | Gly<br>125 | Val | His | Phe |
| Cys | Lys<br>130 | Leu | Ile | Phe | Ala | Ile<br>135 | Tyr | Lys | Met | Ser | Phe<br>140 | Phe | Ser | Gly | Met |
| Leu | Leu | Leu | Leu | Cys | Ile | Ser | Ile | Asp | Arg | Tyr | Val | Ala | Ile | Val | Gln |

|     |     |     |     |     |     |     |     |     |     |     |     |     |     |     |     |
| --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |
| Ala | Val | Ser | Ala | His | Arg | His | Arg | Ala | Arg | Val | Leu | Leu | Ile | Ser | Lys |
|     |     |     |     | 165 |     |     |     |     | 170 |     |     |     |     | 175 |     |
| Leu | Ser | Cys | Val | Gly | Ile | Trp | Ile | Leu | Ala | Thr | Val | Leu | Ser | Ile | Pro |
|     |     |     |     | 180 |     |     |     |     | 185 |     |     |     |     | 190 |     |
| Glu | Leu | Leu | Tyr | Ser | Asp | Leu | Gln | Arg | Ser | Ser | Ser | Glu | Gln | Ala | Met |
|     |     |     | 195 |     |     |     |     | 200 |     |     |     |     | 205 |     |     |
| Arg | Cys | Ser | Leu | Ile | Thr | Glu | His | Val | Glu | Ala | Phe | Ile | Thr | Ile | Gln |
|     |     | 210 |     |     |     |     | 215 |     |     |     |     | 220 |     |     |     |
| Val | Ala | Gln | Met | Val | Ile | Gly | Phe | Leu | Val | Pro | Leu | Leu | Ala | Met | Ser |
| 225 |     |     |     |     | 230 |     |     |     |     | 235 |     |     |     |     | 240 |
| Phe | Cys | Tyr | Leu | Val | Ile | Ile | Arg | Thr | Leu | Leu | Gln | Ala | Arg | Asn | Phe |
|     |     |     |     | 245 |     |     |     |     | 250 |     |     |     |     | 255 |     |
| Glu | Arg | Asn | Lys | Ala | Ile | Lys | Val | Ile | Ala | Val | Val | Val | Val | Val | Phe |
|     |     |     | 260 |     |     |     |     | 265 |     |     |     |     | 270 |     |     |
| Ile | Val | Phe | Gln | Leu | Pro | Tyr | Asn | Gly | Val | Val | Leu | Ala | Gln | Thr | Val |
|     |     | 275 |     |     |     |     | 280 |     |     |     |     | 285 |     |     |     |
| Ala | Asn | Phe | Asn | Ile | Thr | Ser | Ser | Thr | Cys | Glu | Leu | Ser | Lys | Gln | Leu |
|     | 290 |     |     |     |     | 295 |     |     |     |     | 300 |     |     |     |     |
| Asn | Ile | Ala | Tyr | Asp | Val | Thr | Tyr | Ser | Leu | Ala | Cys | Val | Arg | Cys | Cys |
| 305 |     |     |     |     | 310 |     |     |     |     | 315 |     |     |     |     | 320 |
| Val | Asn | Pro | Phe | Leu | Tyr | Ala | Phe | Ile | Gly | Val | Lys | Phe | Arg | Asn | Asp |
|     |     |     |     | 325 |     |     |     |     | 330 |     |     |     |     | 335 |     |
| Leu | Phe | Lys | Leu | Phe | Lys | Asp | Leu | Gly | Cys | Leu | Ser | Gln | Glu | Gln | Leu |
|     |     |     | 340 |     |     |     |     | 345 |     |     |     |     | 350 |     |     |
| Arg | Gln | Trp | Ser | Ser | Cys | Arg | His | Ile | Arg | Arg | Ser | Ser | Met | Ser | Val |
|     |     | 355 |     |     |     |     | 360 |     |     |     |     | 365 |     |     |     |
| Glu | Ala | Glu | Thr | Thr | Thr | Thr | Phe | Ser | Pro |     |     |     |     |     |     |
| 370 |     |     |     |     | 375 |     |     |     |     |     |     |     |     |     |     |

( 2 ) INFORMATION FOR SEQ ID NO:16:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 253..360

( i x ) FEATURE:
        ( A ) NAME/KEY: CDS
        ( B ) LOCATION: 243..251

( i x ) FEATURE:
        ( A ) NAME/KEY: TATA_signal
        ( B ) LOCATION: 151..156

( i x ) FEATURE:
        ( A ) NAME/KEY: 5'UTR
        ( B ) LOCATION: 180..242

( x i ) SEQUENCE DESCRIPTION: SEQ ID NO:16:

```
GGATCCTATG ACCAGCGACT GTCACCCTCT GTCACCTTTC TTCTGCCCTT TATCTCTGAA      60
GGCATTGAAG GGGCCCTGCA TGAGTCAGGG AGGGCTGGGG GGAGGAGCAA GGGTGGGAGG     120
GGCAGGGAAG AGGGTGGCTT CTCCGACAAC TTAAAGGGG CTTGAACCAC TTCCTCCCCA      180
GACAGGGGTA GTGCGAGGCC GGGCACAGCC TTCCTGTGTG GTTTTACCGC CAGAGAGCG      240
```

```
TC ATG GAC CTG GGTGAGTGAG CCTCTTCATG TGAGAAGGAA CAGTACCAGG          291
   Met Asp Leu
    1

GTCTTGGACA CCCAGACTGA CCCTGTGGAA TGGGGGTGGA GGATGCGGGT GGAGCGCATA   351

GGGGTGCTT                                                           360
```

(2) INFORMATION FOR SEQ ID NO:17:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asp Leu
 1
```

(2) INFORMATION FOR SEQ ID NO:18:

(i) SEQUENCE CHARACTERISTICS:
        (A) LENGTH: 1900 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..168

(ix) FEATURE:
        (A) NAME/KEY: exon
        (B) LOCATION: 169..1245

(ix) FEATURE:
        (A) NAME/KEY: CDS
        (B) LOCATION: 169..1242

(ix) FEATURE:
        (A) NAME/KEY: 3'UTR
        (B) LOCATION: 1246..1900

(xi) SEQUENCE DESCRIPTION: SEQ ID NO:18:

```
CTGCAGGGAG CCATGATTGC ACCACTGCAC TCCAGCCTGG GCAACAGAGT GAGACCATGT    60

CTCAAGAAAA AAAAAAAAGA AAGAAACCAC TGCTCTAGGC TAAATCCCAG CCAGAGTTGG   120

AGCCACCCAG CTAAACTGGC CTGTTTTCCC TCATTTCCTT CCCCGAAG GTA TGC CTG   177
                                                    Val Cys Leu
                                                     1

TGT CAA GAT GAG GTC ACG GAC GAT TAC ATC GGA GAC AAC ACC ACA GTG    225
Cys Gln Asp Glu Val Thr Asp Asp Tyr Ile Gly Asp Asn Thr Thr Val
     5               10                  15

GAC TAC ACT TTG TTC GAG TCT TTG TGC TCC AAG AAG GAC GTG CGG AAC    273
Asp Tyr Thr Leu Phe Glu Ser Leu Cys Ser Lys Lys Asp Val Arg Asn
 20              25                  30                  35

TTT AAA GCC TGG TTC CTC CCT ATC ATG TAC TCC ATC ATT TGT TTC GTG    321
Phe Lys Ala Trp Phe Leu Pro Ile Met Tyr Ser Ile Ile Cys Phe Val
                 40                  45                  50

GGC CTA CTG GGC AAT GGG CTG GTC GTG TTG ACC TAT ATC TAT TTC AAG    369
Gly Leu Leu Gly Asn Gly Leu Val Val Leu Thr Tyr Ile Tyr Phe Lys
             55                  60                  65

AGG CTC AAG ACC ATG ACC GAT ACC TAC CTG CTC AAC CTG GCG GTG GCA    417
Arg Leu Lys Thr Met Thr Asp Thr Tyr Leu Leu Asn Leu Ala Val Ala
         70                  75                  80
```

| | | | | | | | | | | | | | | | | |
|---|---|---|---|---|---|---|---|---|---|---|---|---|---|---|---|---|
| GAC | ATC | CTC | TTC | CTC | CTG | ACC | CTT | CCC | TTC | TGG | GCC | TAC | AGC | GCG | GCC | 465 |
| Asp | Ile | Leu | Phe | Leu | Leu | Thr | Leu | Pro | Phe | Trp | Ala | Tyr | Ser | Ala | Ala | |
| | 85 | | | | 90 | | | | | 95 | | | | | | |
| AAG | TCC | TGG | GTC | TTC | GGT | GTC | CAC | TTT | TGC | AAG | CTC | ATC | TTT | GCC | ATC | 513 |
| Lys | Ser | Trp | Val | Phe | Gly | Val | His | Phe | Cys | Lys | Leu | Ile | Phe | Ala | Ile | |
| 100 | | | | | 105 | | | | | 110 | | | | | 115 | |
| TAC | AAG | ATG | AGC | TTC | TTC | AGT | GGC | ATG | CTC | CTA | CTT | CTT | TGC | ATC | AGC | 561 |
| Tyr | Lys | Met | Ser | Phe | Phe | Ser | Gly | Met | Leu | Leu | Leu | Leu | Cys | Ile | Ser | |
| | | | | 120 | | | | | 125 | | | | | 130 | | |
| ATT | GAC | CGC | TAC | GTG | GCC | ATC | GTC | CAG | GCT | GTC | TCA | GCT | CAC | CGC | CAC | 609 |
| Ile | Asp | Arg | Tyr | Val | Ala | Ile | Val | Gln | Ala | Val | Ser | Ala | His | Arg | His | |
| | | | 135 | | | | 140 | | | | | 145 | | | | |
| CGT | GCC | CGC | GTC | CTT | CTC | ATC | AGC | AAG | CTG | TCC | TGT | GTG | GGC | ATC | TGG | 657 |
| Arg | Ala | Arg | Val | Leu | Leu | Ile | Ser | Lys | Leu | Ser | Cys | Val | Gly | Ile | Trp | |
| | | 150 | | | | | 155 | | | | | 160 | | | | |
| ATA | CTA | GCC | ACA | GTG | CTC | TCC | ATC | CCA | GAG | CTC | CTG | TAC | AGT | GAC | CTC | 705 |
| Ile | Leu | Ala | Thr | Val | Leu | Ser | Ile | Pro | Glu | Leu | Leu | Tyr | Ser | Asp | Leu | |
| | 165 | | | | | 170 | | | | | 175 | | | | | |
| CAG | AGG | AGC | AGC | AGT | GAG | CAA | GCG | ATG | CGA | TGC | TCT | CTC | ATC | ACA | GAG | 753 |
| Gln | Arg | Ser | Ser | Ser | Glu | Gln | Ala | Met | Arg | Cys | Ser | Leu | Ile | Thr | Glu | |
| 180 | | | | | 185 | | | | | 190 | | | | | 195 | |
| CAT | GTG | GAG | GCC | TTT | ATC | ACC | ATC | CAG | GTG | GCC | CAG | ATG | GTG | ATC | GGC | 801 |
| His | Val | Glu | Ala | Phe | Ile | Thr | Ile | Gln | Val | Ala | Gln | Met | Val | Ile | Gly | |
| | | | | 200 | | | | | 205 | | | | | 210 | | |
| TTT | CTG | GTC | CCC | CTG | CTG | GCC | ATG | AGC | TTC | TGT | TAC | CTT | GTC | ATC | ATC | 849 |
| Phe | Leu | Val | Pro | Leu | Leu | Ala | Met | Ser | Phe | Cys | Tyr | Leu | Val | Ile | Ile | |
| | | | 215 | | | | | 220 | | | | | 225 | | | |
| CGC | ACC | CTG | CTC | CAG | GCA | CGC | AAC | TTT | GAG | CGC | AAC | AAG | GCC | ATC | AAG | 897 |
| Arg | Thr | Leu | Leu | Gln | Ala | Arg | Asn | Phe | Glu | Arg | Asn | Lys | Ala | Ile | Lys | |
| | | 230 | | | | | 235 | | | | | 240 | | | | |
| GTG | ATC | ATC | GCT | GTG | GTC | GTG | GTC | TTC | ATA | GTC | TTC | CAG | CTG | CCC | TAC | 945 |
| Val | Ile | Ile | Ala | Val | Val | Val | Val | Phe | Ile | Val | Phe | Gln | Leu | Pro | Tyr | |
| | 245 | | | | | 250 | | | | | 255 | | | | | |
| AAT | GGG | GTG | GTC | CTG | GCC | CAG | ACG | GTG | GCC | AAC | TTC | AAC | ATC | ACC | AGT | 993 |
| Asn | Gly | Val | Val | Leu | Ala | Gln | Thr | Val | Ala | Asn | Phe | Asn | Ile | Thr | Ser | |
| 260 | | | | | 265 | | | | | 270 | | | | | 275 | |
| AGC | ACC | TGT | GAG | CTC | AGT | AAG | CAA | CTC | AAC | ATC | GCC | TAC | GAC | GTC | ACC | 1041 |
| Ser | Thr | Cys | Glu | Leu | Ser | Lys | Gln | Leu | Asn | Ile | Ala | Tyr | Asp | Val | Thr | |
| | | | | 280 | | | | | 285 | | | | | 290 | | |
| TAC | AGC | CTG | GCC | TGC | GTC | CGC | TGC | TGC | GTC | AAC | CCT | TTC | TTG | TAC | GCC | 1089 |
| Tyr | Ser | Leu | Ala | Cys | Val | Arg | Cys | Cys | Val | Asn | Pro | Phe | Leu | Tyr | Ala | |
| | | | 295 | | | | | 300 | | | | | 305 | | | |
| TTC | ATC | GGC | GTC | AAG | TTC | CGC | AAC | GAT | CTC | TTC | AAG | CTC | TTC | AAG | GAC | 1137 |
| Phe | Ile | Gly | Val | Lys | Phe | Arg | Asn | Asp | Leu | Phe | Lys | Leu | Phe | Lys | Asp | |
| | | 310 | | | | | 315 | | | | | 320 | | | | |
| CTG | GGC | TGC | CTC | AGC | CAG | GAG | CAG | CTC | CGG | CAG | TGG | TCT | TCC | TGT | CGG | 1185 |
| Leu | Gly | Cys | Leu | Ser | Gln | Glu | Gln | Leu | Arg | Gln | Trp | Ser | Ser | Cys | Arg | |
| | 325 | | | | | 330 | | | | | 335 | | | | | |
| CAC | ATC | CGG | CGC | TCC | TCC | ATG | AGT | GTG | GAG | GCC | GAG | ACC | ACC | ACC | ACC | 1233 |
| His | Ile | Arg | Arg | Ser | Ser | Met | Ser | Val | Glu | Ala | Glu | Thr | Thr | Thr | Thr | |
| 340 | | | | | 345 | | | | | 350 | | | | | 355 | |
| TTC | TCC | CCA | TAGGCGACTC | | TTCTGCCTGG | | ACTAGAGGGA | | CCTCTCCCAG | | | | | | | 1282 |
| Phe | Ser | Pro | | | | | | | | | | | | | | |

```
GGTCCCTGGG GTGGGGATAG GGAGCAGATG CAATGACTCA GGACATCCCC CCGCCAAAAG    1342

CTGCTCAGGG AAAAGCAGCT CTCCCCTCAG AGTGCAAGCC CTGCTCCAGA AGTTAGCTTC    1402

ACCCCAATCC CAGCTACCTC AACCAATGCC GAAAAAGACA GGGCTGATAA GCTAACACCA    1462

GACAGACAAC ACTGGGAAAC AGAGGCTATT GTCCCCTAAA CCAAAAACTG AAAGTGAAAG    1522
```

| TCCAGAAACT | GTTCCCACCT | GCTGGAGTGA | AGGGGCCAAG | GAGGGTGAGT | GCAAGGGGCG | 1582 |
| TGGGAGTGGC | CTGAAGAGTC | CTCTGAATGA | ACCTTCTGGC | CTCCCACAGA | CTCAAATGCT | 1642 |
| CAGACCAGCT | CTTCCGAAAA | CCAGGCCTTA | TCTCCAAGAC | CAGAGATAGT | GGGGAGACTT | 1702 |
| CTTGGCTTGG | TGAGGAAAAG | CGGACATCAG | CAGCTGGTCA | AACAAACTCT | CTGAACCCCT | 1762 |
| CCCTCCATCG | TTTTCTTCAC | TGTCCTCCAA | GCCAGCGGGA | ATGCAGCTGC | CACGCCGCCC | 1822 |
| TAAAAGCACA | CTCATCCCCT | CACTTGCCGC | GTCGCCCTCC | CAGGCTCTCA | ACAGGGGAGA | 1882 |
| GTGTGGTGTT | TCCTGCAG   |            |            |            |            | 1900 |

(2) INFORMATION FOR SEQ ID NO:19:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:19:

```
Val Cys Leu Cys Gln Asp Glu Val Thr Asp Asp Tyr Ile Gly Asp Asn
 1               5                  10                  15

Thr Thr Val Asp Tyr Thr Leu Phe Glu Ser Leu Cys Ser Lys Lys Asp
             20                  25                  30

Val Arg Asn Phe Lys Ala Trp Phe Leu Pro Ile Met Tyr Ser Ile Ile
         35                  40                  45

Cys Phe Val Gly Leu Leu Gly Asn Gly Leu Val Val Leu Thr Tyr Ile
     50                  55                  60

Tyr Phe Lys Arg Leu Lys Thr Met Thr Asp Thr Tyr Leu Leu Asn Leu
 65                  70                  75                  80

Ala Val Ala Asp Ile Leu Phe Leu Leu Thr Leu Pro Phe Trp Ala Tyr
             85                  90                  95

Ser Ala Ala Lys Ser Trp Val Phe Gly Val His Phe Cys Lys Leu Ile
        100                 105                 110

Phe Ala Ile Tyr Lys Met Ser Phe Phe Ser Gly Met Leu Leu Leu Leu
        115                 120                 125

Cys Ile Ser Ile Asp Arg Tyr Val Ala Ile Val Gln Ala Val Ser Ala
    130                 135                 140

His Arg His Arg Ala Arg Val Leu Leu Ile Ser Lys Leu Ser Cys Val
145                 150                 155                 160

Gly Ile Trp Ile Leu Ala Thr Val Leu Ser Ile Pro Glu Leu Leu Tyr
            165                 170                 175

Ser Asp Leu Gln Arg Ser Ser Ser Glu Gln Ala Met Arg Cys Ser Leu
        180                 185                 190

Ile Thr Glu His Val Glu Ala Phe Ile Thr Ile Gln Val Ala Gln Met
        195                 200                 205

Val Ile Gly Phe Leu Val Pro Leu Leu Ala Met Ser Phe Cys Tyr Leu
    210                 215                 220

Val Ile Ile Arg Thr Leu Leu Gln Ala Arg Asn Phe Glu Arg Asn Lys
225                 230                 235                 240

Ala Ile Lys Val Ile Ile Ala Val Val Val Phe Ile Val Phe Gln
            245                 250                 255

Leu Pro Tyr Asn Gly Val Val Leu Ala Gln Thr Val Ala Asn Phe Asn
            260                 265                 270

Ile Thr Ser Ser Thr Cys Glu Leu Ser Lys Gln Leu Asn Ile Ala Tyr
        275                 280                 285
```

-continued

| Asp | Val | Thr | Tyr | Ser | Leu | Ala | Cys | Val | Arg | Cys | Cys | Val | Asn | Pro | Phe |
|     | 290 |     |     |     | 295 |     |     |     |     | 300 |     |     |     |     |     |

| Leu | Tyr | Ala | Phe | Ile | Gly | Val | Lys | Phe | Arg | Asn | Asp | Leu | Phe | Lys | Leu |
| 305 |     |     |     |     | 310 |     |     |     |     | 315 |     |     |     |     | 320 |

| Phe | Lys | Asp | Leu | Gly | Cys | Leu | Ser | Gln | Glu | Gln | Leu | Arg | Gln | Trp | Ser |
|     |     |     |     | 325 |     |     |     |     | 330 |     |     |     |     | 335 |     |

| Ser | Cys | Arg | His | Ile | Arg | Arg | Ser | Ser | Met | Ser | Val | Glu | Ala | Glu | Thr |
|     |     |     | 340 |     |     |     |     | 345 |     |     |     |     | 350 |     |     |

| Thr | Thr | Thr | Phe | Ser | Pro |
|     |     | 355 |     |     |     |

(2) INFORMATION FOR SEQ ID NO:20:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GGYCAATCT      9

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..50

(xi) SEQUENCE DESCRIPTION: SEQ ID NO:21:

| GG | AAA | CCA | ATG | AAA | AGC | GTG | CTG | GTG | GTG | GCT | CTC | CTT | GTC | ATT | TTC | 47 |
|    | Lys | Pro | Met | Lys | Ser | Val | Leu | Val | Val | Ala | Leu | Leu | Val | Ile | Phe |    |
|    | 1   |     |     |     | 5   |     |     |     |     | 10  |     |     |     |     | 15  |    |

CAG      50
Gln (2) INFORMATION FOR SEQ ID NO:22:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:22:

| Lys | Pro | Met | Lys | Ser | Val | Leu | Val | Val | Ala | Leu | Leu | Val | Ile | Phe | Gln |
| 1   |     |     |     | 5   |     |     |     |     | 10  |     |     |     |     | 15  |     |

(2) INFORMATION FOR SEQ ID NO:23:

(i) SEQUENCE CHARACTERISTICS:
        (A) LENGTH: 2751 base pairs
        (B) TYPE: nucleic acid
        (C) STRANDEDNESS: single
        (D) TOPOLOGY: linear (ii) MOLECULE TYPE: DNA (genomic)

( i x ) FEATURE:
: (A) NAME/KEY: intron
: (B) LOCATION: 1..691

( i x ) FEATURE:
: (A) NAME/KEY: exon
: (B) LOCATION: 692..1771

( i x ) FEATURE:
: (A) NAME/KEY: CDS
: (B) LOCATION: 692..1768

( i x ) FEATURE:
: (A) NAME/KEY: polyA_signal
: (B) LOCATION: 2341..2348

( x i ) SEQUENCE DESCRIPTION: SEQ ID NO:23:

```
CTGCAGGGCC AGACGTTTAC ATCTTAACTA GATCCTCCCT GAGTAATTCA TACATGTGCT      60
AACATCGTTA CTTAGATTTA TTTTTGTTT  TGGTTTGGTT TTTTGGCTTT TTAAGATTTT     120
TTTATTCATT GAACGTAAAT GCATACACTG TAGCTATCTT TAGACACATG AGAAGAAGGT     180
ATCAGACCCA TTACAGATGG TTGTGAGCCA CCGTGGTGTT TGCTGGGAAT TGAACCCAGG     240
ACTTTTGGAA GAGCAGTCCG TATTCTTAAC CTATTAGATA TTATTTATGG GTATAAACAT     300
TTTGCCTGCG TGCATAGAAG TACACCACAT GCACAGAGGA GGTCAGAGTT GGGCATCAGA     360
GCCCATGGAA CTAGAGTTAC AGAGAGCCAC GACGCACCGT GTGGGTGCTG GGAACCGAAC     420
CGGCCTTCTC TACCAGAGCT ACACGCACTC TGCTCTTAAC CCCTGAGCCA GTTCTTCAGC     480
CCCACATGCT GAGGCTTAAG AGGTGTGGAT TTCTAGTCAA AGACTCACTT GGGGTTTGAG     540
GGGGAAACTA TAGTTTCCTG GGCTCCTCCG TCTAAGATGC TGACCCAAAG GGTCTAAGGT     600
CTGAGAGTCT GCAAGAGAAC AGAAGCCCCG GGCAATGTCC TGACTGTGAG ATCCGGACTG     660
TGAGCTCATC AGGTGCTTCC TTCCCCCGGA G GTG TGC TTC TGC CAA GAT GAG        712
                                 Val Cys Phe Cys Gln Asp Glu
                                  1               5
GTC ACG AGT GAC TAC ATC GGC GAG AAT ACC ACG GTG GAC TAC ACC CTG      760
Val Thr Ser Asp Tyr Ile Gly Glu Asn Thr Thr Val Asp Tyr Thr Leu
         10                  15                  20
TAC GAG TCG GTG TGC TTC AAG AAG GAT GTG CGG AAC TTT AAG GCC TGG      808
Tyr Glu Ser Val Cys Phe Lys Lys Asp Val Arg Asn Phe Lys Ala Trp
     25                  30                  35
TTC CTG CCT CTC ATG TAT TCT GTC ATC TGC TTC GTG GGC CTG CTC GGC      856
Phe Leu Pro Leu Met Tyr Ser Val Ile Cys Phe Val Gly Leu Leu Gly
 40                  45                  50                  55
AAC GGG CTG GTG ATA CTG ACG TAC ATC TAT TTC AAG AGG CTC AAG ACC      904
Asn Gly Leu Val Ile Leu Thr Tyr Ile Tyr Phe Lys Arg Leu Lys Thr
                 60                  65                  70
ATG ACG GAT ACC TAC CTG CTC AAC CTG GCC GTG GCA GAC ATC CTT TTC      952
Met Thr Asp Thr Tyr Leu Leu Asn Leu Ala Val Ala Asp Ile Leu Phe
             75                  80                  85
CTC CTA ATT CTT CCC TTC TGG GCC TAC AGC GAA GCC AAG TCC TGG ATC     1000
Leu Leu Ile Leu Pro Phe Trp Ala Tyr Ser Glu Ala Lys Ser Trp Ile
         90                  95                 100
TTT GGC GTC TAC CTG TGT AAG GGC ATC TTT GGC ATC TAT AAG TTA AGC     1048
Phe Gly Val Tyr Leu Cys Lys Gly Ile Phe Gly Ile Tyr Lys Leu Ser
     105                 110                 115
TTC TTC AGC GGG ATG CTG CTC CTA TGC ATC AGC ATT GAC CGC TAC         1096
Phe Phe Ser Gly Met Leu Leu Leu Cys Ile Ser Ile Asp Arg Tyr
 120                 125                 130                 135
GTA GCC ATC GTC CAG GCC GTG TCG CGT CAT CGC CAC CGC GCC CGC GTG     1144
Val Ala Ile Val Gln Ala Val Ser Arg His Arg His Arg Ala Arg Val
                 140                 145                 150
```

| | | | | | | | | | | | | | | | | |
|---|---|---|---|---|---|---|---|---|---|---|---|---|---|---|---|---|
| CTT | CTC | ATC | AGC | AAG | CTG | TCC | TGT | GTG | GGC | ATC | TGG | ATG | CTG | GCC | CTC | 1192 |
| Leu | Leu | Ile | Ser 155 | Lys | Leu | Ser | Cys | Val 160 | Gly | Ile | Trp | Met | Leu 165 | Ala | Leu | |
| TTC | CTC | TCC | ATC | CCG | GAG | CTG | CTC | TAC | AGC | GGC | CTC | CAG | AAG | AAC | AGC | 1240 |
| Phe | Leu | Ser 170 | Ile | Pro | Glu | Leu | Leu 175 | Tyr | Ser | Gly | Leu | Gln 180 | Lys | Asn | Ser | |
| GGC | GAG | GAC | ACG | CTG | AGA | TGC | TCA | CTG | GTC | AGT | GCC | CAA | GTG | GAG | GCC | 1288 |
| Gly | Glu | Asp 185 | Thr | Leu | Arg | Cys | Ser 190 | Leu | Val | Ser | Ala | Gln 195 | Val | Glu | Ala | |
| TTG | ATC | ACC | ATC | CAA | GTG | GCC | CAG | ATG | GTT | TTT | GGG | TTC | CTA | GTG | CCT | 1336 |
| Leu 200 | Ile | Thr | Ile | Gln | Val 205 | Ala | Gln | Met | Val | Phe 210 | Gly | Phe | Leu | Val | Pro 215 | |
| ATG | CTG | GCT | ATG | AGT | TTC | TGC | TAC | CTC | ATT | ATC | ATC | CGT | ACC | TTG | CTC | 1384 |
| Met | Leu | Ala | Met | Ser 220 | Phe | Cys | Tyr | Leu | Ile 225 | Ile | Ile | Arg | Thr | Leu 230 | Leu | |
| CAG | GCA | CGC | AAC | TTT | GAG | CGG | AAC | AAG | GCC | ATC | AAG | GTG | ATC | ATT | GCC | 1432 |
| Gln | Ala | Arg | Asn 235 | Phe | Glu | Arg | Asn | Lys 240 | Ala | Ile | Lys | Val | Ile 245 | Ile | Ala | |
| GTG | GTG | GTA | GTC | TTC | ATA | GTC | TTC | CAG | CTG | CCC | TAC | AAT | GGG | GTG | GTC | 1480 |
| Val | Val | Val 250 | Val | Phe | Ile | Val | Phe 255 | Gln | Leu | Pro | Tyr | Asn 260 | Gly | Val | Val | |
| CTG | GCT | CAG | ACG | GTG | GCC | AAC | TTC | AAC | ATC | ACC | AAT | AGC | AGC | TGC | TGC | 1528 |
| Leu | Ala 265 | Gln | Thr | Val | Ala | Asn 270 | Phe | Asn | Ile | Thr | Asn 275 | Ser | Ser | Cys | Cys | |
| GAA | ACC | AGC | AAG | CAG | CTC | AAC | ATT | GCC | TAT | GAC | GTC | ACC | TAC | AGC | CTG | 1576 |
| Glu 280 | Thr | Ser | Lys | Gln | Leu 285 | Asn | Ile | Ala | Tyr | Asp 290 | Val | Thr | Tyr | Ser | Leu 295 | |
| GCC | TCC | GTC | CGC | TGC | TGC | GTC | AAC | CCT | TTC | TTG | TAT | GCC | TTC | ATC | GGC | 1624 |
| Ala | Ser | Val | Arg | Cys 300 | Cys | Val | Asn | Pro | Phe 305 | Leu | Tyr | Ala | Phe | Ile 310 | Gly | |
| GTC | AAG | TTC | CGC | AGC | GAC | CTC | TTC | AAG | CTC | TTC | AAG | GAC | TTG | GGC | TGC | 1672 |
| Val | Lys | Phe | Arg 315 | Ser | Asp | Leu | Phe | Lys 320 | Leu | Phe | Lys | Asp | Leu 325 | Gly | Cys | |
| CTC | AGC | CAG | GAA | CGG | CTC | CGG | CAC | TGG | TCT | TCC | TGC | CGG | CAT | GTA | CGG | 1720 |
| Leu | Ser | Gln 330 | Glu | Arg | Leu | Arg | His 335 | Trp | Ser | Ser | Cys | Arg 340 | His | Val | Arg | |
| AAC | GCG | TCG | GTG | AGC | ATG | GAG | GCG | GAG | ACC | ACC | ACA | ACC | TTC | TCC | CCG | 1768 |
| Asn | Ala 345 | Ser | Val | Ser | Met | Glu 350 | Ala | Glu | Thr | Thr | Thr 355 | Thr | Phe | Ser | Pro | |

| | | | | | |
|---|---|---|---|---|---|
| TAGGGGGCTC | CCCTGCCCGG | ACTACAAGGA | CCTCTCCCAG | GAGCCTTAAT | GTGGTGCACA | 1828 |
| CATGCACAGA | CTCTCCATCC | ACCGAATTGC | TGCTGAGGGA | AGAGCAATTC | TGGCCAGTCA | 1888 |
| GGTTGACATG | AGGACCTAAG | AAACTGCTTA | ACCCCATCCC | ACTTATAACT | ACCTCAACCA | 1948 |
| AAGCTGTAAA | AGATATGGCT | GAGAAGTTAA | CACTCAAGCC | AAGACAGCTA | TCCCCAAAAC | 2008 |
| GACAGCCAAA | AGTGAAAGTG | AGAGGCTCCA | CACTTTCCGG | AGTGAGGGAT | GTGGGGCCAG | 2068 |
| TGAACACCCT | GGTTGAGTAG | TCTTCGGAGG | CCTCTGAATG | AACCTGCTTC | TAGCTTAGAG | 2128 |
| AGATGTCCCG | GAGATTCAAG | ACAGAGCTTA | TCTCCACACT | TAGCAAGCAA | GCAAGAGATG | 2188 |
| ACAGTCTCTC | TAAATGCTCC | CACAGAGCAC | CCCTGCCCCT | CCCTTCTGCC | TCTCCACCGC | 2248 |
| CTTTCCTGAG | GTCCAGGCCA | CACCATGACG | CTGAGGCAGT | CCCAGCTGGG | GCTCTGGATG | 2308 |
| GCAATGACAA | GTAGTTGGGT | CTCTATGATG | GGAATAAAAA | GGTAGGGGAA | AGGTGACAGG | 2368 |
| AAGGAGAGAA | GGTGACCCTG | CTGGCTGACA | GAGGCCAGCA | AGCTACTTCT | TTGTTCTCTG | 2428 |
| TCAGCCAGCC | ACTGATACCT | TTCCTCATGT | TCTGCTTTTG | ATTCATATAT | CTTTTATGAA | 2488 |
| GAAACAAATA | AAAAAAAAAT | TTTCCCTCGA | GGAAACAACT | TGGAAAGAAG | GGAGGTAAAT | 2548 |
| TCCTTGGTTA | AATGGCGAGT | GAGTGAGTTG | TCCCCCCATT | CCACCTGAGA | GTCCTGCGCC | 2608 |

```
CCACACCCCT CCGCCCCAGC CTTCCTTTCT CAGCACTCAG AACCATGAGG TCACAGAGCC    2668

TCTCCGGAGA TGCAAACCCA GGAGGCTGCA AGAGGTGGAA AAAGAGCGAA GACAGGATGT    2728

CTGTCTTGCA CATACACCTG CAG                                            2751
```

( 2 ) INFORMATION FOR SEQ ID NO:24:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Val Cys Phe Cys Gln Asp Glu Val Thr Ser Asp Tyr Ile Gly Glu Asn
 1               5                  10                  15

Thr Thr Val Asp Tyr Thr Leu Tyr Glu Ser Val Cys Phe Lys Lys Asp
            20                  25                  30

Val Arg Asn Phe Lys Ala Trp Phe Leu Pro Leu Met Tyr Ser Val Ile
        35                  40                  45

Cys Phe Val Gly Leu Leu Gly Asn Gly Leu Val Ile Leu Thr Tyr Ile
    50                  55                  60

Tyr Phe Lys Arg Leu Lys Thr Met Thr Asp Thr Tyr Leu Leu Asn Leu
65                  70                  75                  80

Ala Val Ala Asp Ile Leu Phe Leu Leu Ile Leu Pro Phe Trp Ala Tyr
                85                  90                  95

Ser Glu Ala Lys Ser Trp Ile Phe Gly Val Tyr Leu Cys Lys Gly Ile
                100                 105                 110

Phe Gly Ile Tyr Lys Leu Ser Phe Phe Ser Gly Met Leu Leu Leu Leu
            115                 120                 125

Cys Ile Ser Ile Asp Arg Tyr Val Ala Ile Val Gln Ala Val Ser Arg
    130                 135                 140

His Arg His Arg Ala Arg Val Leu Leu Ile Ser Lys Leu Ser Cys Val
145                 150                 155                 160

Gly Ile Trp Met Leu Ala Leu Phe Leu Ser Ile Pro Glu Leu Leu Tyr
                165                 170                 175

Ser Gly Leu Gln Lys Asn Ser Gly Glu Asp Thr Leu Arg Cys Ser Leu
                180                 185                 190

Val Ser Ala Gln Val Glu Ala Leu Ile Thr Ile Gln Val Ala Gln Met
            195                 200                 205

Val Phe Gly Phe Leu Val Pro Met Leu Ala Met Ser Phe Cys Tyr Leu
    210                 215                 220

Ile Ile Ile Arg Thr Leu Leu Gln Ala Arg Asn Phe Glu Arg Asn Lys
225                 230                 235                 240

Ala Ile Lys Val Ile Ile Ala Val Val Val Phe Ile Val Phe Gln
                245                 250                 255

Leu Pro Tyr Asn Gly Val Val Leu Ala Gln Thr Val Ala Asn Phe Asn
                260                 265                 270

Ile Thr Asn Ser Ser Cys Cys Glu Thr Ser Lys Gln Leu Asn Ile Ala
            275                 280                 285

Tyr Asp Val Thr Tyr Ser Leu Ala Ser Val Arg Cys Cys Val Asn Pro
    290                 295                 300

Phe Leu Tyr Ala Phe Ile Gly Val Lys Phe Arg Ser Asp Leu Phe Lys
305                 310                 315                 320

Leu Phe Lys Asp Leu Gly Cys Leu Ser Gln Glu Arg Leu Arg His Trp
                325                 330                 335
```

Ser Ser Cys Arg His Val Arg Asn Ala Ser Val Ser Met Glu Ala Glu
            340                 345                 350
Thr Thr Thr Thr Phe Ser Pro
            355

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

TGGACTCACT ATTTGATAAA TGAAAGGGC CTCCACAATG CCATGTGCAA ATTCACTACC    60

( 2 ) INFORMATION FOR SEQ ID NO:26:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

AATGCTGATG ACGGTGATGA AGAATATGCT TCCAAAAAAG CCGATGAAGA AGAAGGCGGT    60

AGTGAA    66

( 2 ) INFORMATION FOR SEQ ID NO:27:

( i ) SEQUENCE CHARACTERISTICS:
        ( A ) LENGTH: 2254 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 593..1657

( x i ) SEQUENCE DESCRIPTION: SEQ ID NO:27:

AAGCTTCAAA AAGCCTAGAG CTGGCTGGGC GCTGTGGCTC ACGCCTGTAA TCCTAGCATT    60

TTGGGAGGCT GAGGCGGAAG GATAACTGAG GTCAGGAGTT TGAGACCAGC CTGGCTAACA    120

TGATGAAACC CCATCTCTAC TAAAAATACA AAAATTAGCC AGGCATGGTA GTGCACGCTA    180

TAANCCCAGC TATTTGGGAG GCTGAGGCAG GAGAATCGCT TGAACCCCAG GGACAGAGGT    240

TGCAGTGAGC TGAGATCGCA CCACTGCACT CCAGCCTGGG TGACACAGCG AGACTCCATT    300

TAAAAAAAAA AAAATGCCTA GAGCCAAATG CTCACAGAGC CATTTACTGC ATGGCTTTGG    360

GCAAGTCAAA GGAGTCCGCC TCTCCTGTCA GAAGAGTCTG TTGCAGTCTT CATCACAAGA    420

CTGTTGTGGG GATTAAACAA GATGGCAAGT GGGAAGTTGG GAAATGTAGT GTGCACCCAA    480

CCAATATTTG TTTCTTCCTG CCTGCCTACA TATGAGGCCA CACAGAATTC CAACTTTGTT    540

TCTCTGATAA CTAACACAGT TACTTGTTTT TCTTTCTGAT CCAGGCCTTC ACC ATG    596
    Met
    1

GAT CAG TTC CCT GAA TCA GTG ACA GAA AAC TTT GAG TAC GAT GAT TTG    644
Asp Gln Phe Pro Glu Ser Val Thr Glu Asn Phe Glu Tyr Asp Asp Leu

| | | | | | | | | | | | | | | | | |
|---|---|---|---|---|---|---|---|---|---|---|---|---|---|---|---|---|
| | | | | 5 | | | | | 10 | | | | | 15 | | |
| GCT | GAG | GCC | TGT | TAT | ATT | GGG | GAC | ATC | GTG | GTC | TTT | GGG | ACT | GTG | TTC | 692 |
| Ala | Glu | Ala | Cys | Tyr | Ile | Gly | Asp | Ile | Val | Val | Phe | Gly | Thr | Val | Phe | |
| | | 20 | | | | | 25 | | | | | 30 | | | | |
| CTG | TCC | ATA | TTC | TAC | TCC | GTC | ATC | TTT | GCC | ATT | GGC | CTG | GTG | GGA | AAT | 740 |
| Leu | Ser | Ile | Phe | Tyr | Ser | Val | Ile | Phe | Ala | Ile | Gly | Leu | Val | Gly | Asn | |
| | 35 | | | | | 40 | | | | | 45 | | | | | |
| TTG | TTG | GTA | GTG | TTT | GCC | CTC | ACC | AAC | AGC | AAG | AAG | CCC | AAG | AGT | GTC | 788 |
| Leu | Leu | Val | Val | Phe | Ala | Leu | Thr | Asn | Ser | Lys | Lys | Pro | Lys | Ser | Val | |
| 50 | | | | | 55 | | | | | 60 | | | | | 65 | |
| ACC | GAC | ATT | TAC | CTC | CTG | AAC | CTG | GCC | TTG | TCT | GAT | CTG | CTG | TTT | GTA | 836 |
| Thr | Asp | Ile | Tyr | Leu | Leu | Asn | Leu | Ala | Leu | Ser | Asp | Leu | Leu | Phe | Val | |
| | | | | 70 | | | | | 75 | | | | | 80 | | |
| GCC | ACT | TTG | CCC | TTC | TGG | ACT | CAC | TAT | TTG | ATA | AAT | GAA | AAG | GGC | CTC | 884 |
| Ala | Thr | Leu | Pro | Phe | Trp | Thr | His | Tyr | Leu | Ile | Asn | Glu | Lys | Gly | Leu | |
| | | | | 85 | | | | | 90 | | | | | 95 | | |
| CAC | AAT | GCC | ATG | TGC | AAA | TTC | ACT | ACC | GCC | TTC | TTC | TTC | ATC | GGC | TTT | 932 |
| His | Asn | Ala | Met | Cys | Lys | Phe | Thr | Thr | Ala | Phe | Phe | Phe | Ile | Gly | Phe | |
| | | 100 | | | | | 105 | | | | | 110 | | | | |
| TTT | GGA | AGC | ATA | TTC | TTC | ATC | ACC | GTC | ATC | AGC | ATT | GAT | AGG | TAC | CTG | 980 |
| Phe | Gly | Ser | Ile | Phe | Phe | Ile | Thr | Val | Ile | Ser | Ile | Asp | Arg | Tyr | Leu | |
| | 115 | | | | | 120 | | | | | 125 | | | | | |
| GCC | ATC | GTC | CTG | GCC | GCC | AAC | TCC | ATG | AAC | AAC | CGG | ACC | GTG | CAG | CAT | 1028 |
| Ala | Ile | Val | Leu | Ala | Ala | Asn | Ser | Met | Asn | Asn | Arg | Thr | Val | Gln | His | |
| 130 | | | | | 135 | | | | | 140 | | | | | 145 | |
| GGC | GTC | ACC | ATC | AGC | CTA | GGC | GTC | TGG | GCA | GCA | GCC | ATT | TTG | GTG | GCA | 1076 |
| Gly | Val | Thr | Ile | Ser | Leu | Gly | Val | Trp | Ala | Ala | Ala | Ile | Leu | Val | Ala | |
| | | | | 150 | | | | | 155 | | | | | 160 | | |
| GCA | CCC | CAG | TTC | ATG | TTC | ACA | AAG | CAG | AAA | GAA | AAT | GAA | TGC | CTT | GGT | 1124 |
| Ala | Pro | Gln | Phe | Met | Phe | Thr | Lys | Gln | Lys | Glu | Asn | Glu | Cys | Leu | Gly | |
| | | | | 165 | | | | | 170 | | | | | 175 | | |
| GAC | TAC | CCC | GAG | GTC | CTC | CAG | GAA | ATC | TGG | CCC | GTG | CTC | CGC | AAT | GTG | 1172 |
| Asp | Tyr | Pro | Glu | Val | Leu | Gln | Glu | Ile | Trp | Pro | Val | Leu | Arg | Asn | Val | |
| | | 180 | | | | | 185 | | | | | 190 | | | | |
| GAA | ACA | AAT | TTT | CTT | GGC | TTC | CTA | CTC | CCC | CTG | CTC | ATT | ATG | AGT | TAT | 1220 |
| Glu | Thr | Asn | Phe | Leu | Gly | Phe | Leu | Leu | Pro | Leu | Leu | Ile | Met | Ser | Tyr | |
| | 195 | | | | | 200 | | | | | 205 | | | | | |
| TGC | TAC | TTC | AGA | ATC | ATC | CAG | ACG | CTG | TTT | TCC | TGC | AAG | AAC | CAC | AAG | 1268 |
| Cys | Tyr | Phe | Arg | Ile | Ile | Gln | Thr | Leu | Phe | Ser | Cys | Lys | Asn | His | Lys | |
| 210 | | | | | 215 | | | | | 220 | | | | | 225 | |
| AAA | GCC | AAA | GCC | ATT | AAA | CTG | ATC | CTT | CTG | GTG | GTC | ATC | GTG | TTT | TTC | 1316 |
| Lys | Ala | Lys | Ala | Ile | Lys | Leu | Ile | Leu | Leu | Val | Val | Ile | Val | Phe | Phe | |
| | | | | 230 | | | | | 235 | | | | | 240 | | |
| CTC | TTC | TGG | ACA | CCC | TAC | AAC | GTT | ATG | ATT | TTC | CTG | GAG | ACG | CTT | AAG | 1364 |
| Leu | Phe | Trp | Thr | Pro | Tyr | Asn | Val | Met | Ile | Phe | Leu | Glu | Thr | Leu | Lys | |
| | | | | 245 | | | | | 250 | | | | | 255 | | |
| CTC | TAT | GAC | TTC | TTT | CCC | AGT | TGT | GAC | ATG | AGG | AAG | GAT | CTG | AGG | CTG | 1412 |
| Leu | Tyr | Asp | Phe | Phe | Pro | Ser | Cys | Asp | Met | Arg | Lys | Asp | Leu | Arg | Leu | |
| | | 260 | | | | | 265 | | | | | 270 | | | | |
| GCC | CTC | AGT | GTG | ACT | GAG | ACG | GTT | GCA | TTT | AGC | CAT | TGT | TGC | CTG | AAT | 1460 |
| Ala | Leu | Ser | Val | Thr | Glu | Thr | Val | Ala | Phe | Ser | His | Cys | Cys | Leu | Asn | |
| | 275 | | | | | 280 | | | | | 285 | | | | | |
| CCT | CTC | ATC | TAT | GCA | TTT | GCT | GGG | GAG | AAG | TTC | AGA | AGA | TAC | CTT | TAC | 1508 |
| Pro | Leu | Ile | Tyr | Ala | Phe | Ala | Gly | Glu | Lys | Phe | Arg | Arg | Tyr | Leu | Tyr | |
| 290 | | | | | 295 | | | | | 300 | | | | | 305 | |
| CAC | CTG | TAT | GGG | AAA | TGC | CTG | GCT | GTC | CTG | TGT | GGG | CGC | TCA | GTC | CAC | 1556 |
| His | Leu | Tyr | Gly | Lys | Cys | Leu | Ala | Val | Leu | Cys | Gly | Arg | Ser | Val | His | |
| | | | | 310 | | | | | 315 | | | | | 320 | | |
| GTT | GAT | TTC | TCC | TCA | TCT | GAA | TCA | CAA | AGG | AGC | AGG | CAT | GGA | AGT | GTT | 1604 |
| Val | Asp | Phe | Ser | Ser | Ser | Glu | Ser | Gln | Arg | Ser | Arg | His | Gly | Ser | Val | |

| | | | | | | | | | | | | | | |
|---|---|---|---|---|---|---|---|---|---|---|---|---|---|---|
| | | | 325 | | | | | 330 | | | | | 335 | |
| CTG | AGC | AGC | AAT | TTT | ACT | TAC | CAC | ACG | AGT | GAT | GGA | GAT | GCA | TTG CTC | 1652
| Leu | Ser | Ser | Asn | Phe | Thr | Tyr | His | Thr | Ser | Asp | Gly | Asp | Ala | Leu Leu |
| | | 340 | | | | | 345 | | | | | 350 | | |

```
CTT CTC TGAAGGGAAT CCCAAAGCCT TGTGTCTACA GAGAACCTGG AGTTCCTGAA         1708
Leu Leu
    355

CCTGATGCTG ACTAGTGAGG AAAGATTTTT GTTGTTATTT CTTACAGGCA CAAAATGATG     1768

GACCCAATGC ACACAAAACA ACCCTAGAGT GTTGTTGAGA ATTGTGCTCA AAATTTGAAG     1828

AATGAACAAA TTGAACTCTT TGAATGACAA AGAGTAGACA TTTCTCTTAC TGCAAATGTC     1888

ATCAGAACTT TTTGGTTTGC AGATGACAAA AATTCAATCT AGACTAGTTT AGTTAAATGA     1948

GGGTGGTGAA TATTGTTCAT ATTGTGGCAC AAGCAAAAGG GTGTCTGAGC CCTCAAAGTG     2008

AGGGGAAACC AGGCCTGAGC CAAGCTAGAA TTCCCTCTCT CTGACTCTCA AATCTTTTAG     2068

TCATTATAGA TCCCCCAGAC TTTACATGAC ACAGCTTTAT CACCAGAGAG GGACTGTCTC     2128

CCATGTTTCT CTGCGCCCAA GGGCAAAATT CCCAGGGAAG TGCTCTGATA GGCCAAGTTT     2188

GTATCAGGTG CCCATCCCTG GAAGGTGCTG TTATCCATGG GGAAGGGATA TATAAGATGG     2248

AAGCTT                                                                2254
```

( 2 ) INFORMATION FOR SEQ ID NO:28:

( i ) SEQUENCE CHARACTERISTICS:
    ( A ) LENGTH: 355 amino acids
    ( B ) TYPE: amino acid
    ( D ) TOPOLOGY: linear ( i i ) MOLECULE TYPE: protein ( x i ) SEQUENCE DESCRIPTION: SEQ ID NO:28:

```
Met Asp Gln Phe Pro Glu Ser Val Thr Glu Asn Phe Glu Tyr Asp Asp
 1               5                  10                  15

Leu Ala Glu Ala Cys Tyr Ile Gly Asp Ile Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205
```

| Tyr | Cys | Tyr | Phe | Arg | Ile | Ile | Gln | Thr | Leu | Phe | Ser | Cys | Lys | Asn | His |
|---|---|---|---|---|---|---|---|---|---|---|---|---|---|---|---|
| | 210 | | | | | 215 | | | | 220 | | | | | |

| Lys | Lys | Ala | Lys | Ala | Ile | Lys | Leu | Ile | Leu | Leu | Val | Val | Ile | Val | Phe |
|---|---|---|---|---|---|---|---|---|---|---|---|---|---|---|---|
| 225 | | | | | 230 | | | | 235 | | | | | | 240 |

| Phe | Leu | Phe | Trp | Thr | Pro | Tyr | Asn | Val | Met | Ile | Phe | Leu | Glu | Thr | Leu |
|---|---|---|---|---|---|---|---|---|---|---|---|---|---|---|---|
| | | | | 245 | | | | | 250 | | | | | 255 | |

| Lys | Leu | Tyr | Asp | Phe | Phe | Pro | Ser | Cys | Asp | Met | Arg | Lys | Asp | Leu | Arg |
|---|---|---|---|---|---|---|---|---|---|---|---|---|---|---|---|
| | | | 260 | | | | | 265 | | | | | 270 | | |

| Leu | Ala | Leu | Ser | Val | Thr | Glu | Thr | Val | Ala | Phe | Ser | His | Cys | Cys | Leu |
|---|---|---|---|---|---|---|---|---|---|---|---|---|---|---|---|
| | | 275 | | | | 280 | | | | | 285 | | | | |

| Asn | Pro | Leu | Ile | Tyr | Ala | Phe | Ala | Gly | Glu | Lys | Phe | Arg | Arg | Tyr | Leu |
|---|---|---|---|---|---|---|---|---|---|---|---|---|---|---|---|
| | 290 | | | | | 295 | | | | | 300 | | | | |

| Tyr | His | Leu | Tyr | Gly | Lys | Cys | Leu | Ala | Val | Leu | Cys | Gly | Arg | Ser | Val |
|---|---|---|---|---|---|---|---|---|---|---|---|---|---|---|---|
| 305 | | | | | 310 | | | | | 315 | | | | | 320 |

| His | Val | Asp | Phe | Ser | Ser | Ser | Glu | Ser | Gln | Arg | Ser | Arg | His | Gly | Ser |
|---|---|---|---|---|---|---|---|---|---|---|---|---|---|---|---|
| | | | | 325 | | | | | 330 | | | | | 335 | |

| Val | Leu | Ser | Ser | Asn | Phe | Thr | Tyr | His | Thr | Ser | Asp | Gly | Asp | Ala | Leu |
|---|---|---|---|---|---|---|---|---|---|---|---|---|---|---|---|
| | | | 340 | | | | | 345 | | | | | 350 | | |

| Leu | Leu | Leu |
|---|---|---|
| | | 355 |

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TGGACTCACT ATTTGATAAA         20

(2) INFORMATION FOR SEQ ID NO:30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AAGATTTGAG AGTCAGAG         18

(2) INFORMATION FOR SEQ ID NO:31:

(i) SEQUENCE CHARACTERISTICS:
        (A) LENGTH: 1161 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 7..80

(ix) FEATURE:
        (A) NAME/KEY: CDS
        (B) LOCATION: 94..1158

( x i ) SEQUENCE DESCRIPTION: SEQ ID NO:31:

| | | | | | | | | | | |
|---|---|---|---|---|---|---|---|---|---|---|
| GAATTCACTC | GTCTCTGGTA | AAGTCTGAGC | AGGACAGGGT | GGCTGACTGG | CAGATCCAGA | | | | | 60 |

| | | | | | | | | | | | | | | |
|---|---|---|---|---|---|---|---|---|---|---|---|---|---|---|
| GGTTCCCTTG | GCAGTCCACG | CCAGGCCTTC | ACC | ATG | GAT | CAG | TTC | CCT | GAA | TCA | | | | 114 |
| | | | | Met | Asp | Gln | Phe | Pro | Glu | Ser | | | | |
| | | | | 1 | | | | 5 | | | | | | |

| GTG | ACA | GAA | AAC | TTT | GAG | TAC | GAT | GAT | TTG | GCT | GAG | GCC | TGT | TAT | ATT | 162 |
|---|---|---|---|---|---|---|---|---|---|---|---|---|---|---|---|---|
| Val | Thr | Glu | Asn | Phe | Glu | Tyr | Asp | Asp | Leu | Ala | Glu | Ala | Cys | Tyr | Ile | |
| | | 10 | | | | | 15 | | | | | 20 | | | | |

| GGG | GAC | ATC | GTG | GTC | TTT | GGG | ACT | GTG | TTC | CTG | TCC | ATA | TTC | TAC | TCC | 210 |
|---|---|---|---|---|---|---|---|---|---|---|---|---|---|---|---|---|
| Gly | Asp | Ile | Val | Val | Phe | Gly | Thr | Val | Phe | Leu | Ser | Ile | Phe | Tyr | Ser | |
| | | 25 | | | | 30 | | | | | 35 | | | | | |

| GTC | ATC | TTT | GCC | ATT | GGC | CTG | GTG | GGA | AAT | TTG | TTG | GTA | GTG | TTT | GCC | 258 |
|---|---|---|---|---|---|---|---|---|---|---|---|---|---|---|---|---|
| Val | Ile | Phe | Ala | Ile | Gly | Leu | Val | Gly | Asn | Leu | Leu | Val | Val | Phe | Ala | |
| 40 | | | | | 45 | | | | | 50 | | | | | 55 | |

| CTC | ACC | AAC | AGC | AAG | AAG | CCC | AAG | AGT | GTC | ACC | GAC | ATT | TAC | CTC | CTG | 306 |
|---|---|---|---|---|---|---|---|---|---|---|---|---|---|---|---|---|
| Leu | Thr | Asn | Ser | Lys | Lys | Pro | Lys | Ser | Val | Thr | Asp | Ile | Tyr | Leu | Leu | |
| | | | | 60 | | | | | 65 | | | | | 70 | | |

| AAC | CTG | GCC | TTG | TCT | GAT | CTG | CTG | TTT | GTA | GCC | ACT | TTG | CCC | TTC | TGG | 354 |
|---|---|---|---|---|---|---|---|---|---|---|---|---|---|---|---|---|
| Asn | Leu | Ala | Leu | Ser | Asp | Leu | Leu | Phe | Val | Ala | Thr | Leu | Pro | Phe | Trp | |
| | | | 75 | | | | | 80 | | | | | 85 | | | |

| ACT | CAC | TAT | TTG | ATA | AAT | GAA | AAG | GGC | CTC | CAC | AAT | GCC | ATG | TGC | AAA | 402 |
|---|---|---|---|---|---|---|---|---|---|---|---|---|---|---|---|---|
| Thr | His | Tyr | Leu | Ile | Asn | Glu | Lys | Gly | Leu | His | Asn | Ala | Met | Cys | Lys | |
| | | 90 | | | | | 95 | | | | | 100 | | | | |

| TTC | ACT | ACC | GCC | TTC | TTC | TTC | ATC | GGC | TTT | TTT | GGA | AGC | ATA | TTC | TTC | 450 |
|---|---|---|---|---|---|---|---|---|---|---|---|---|---|---|---|---|
| Phe | Thr | Thr | Ala | Phe | Phe | Phe | Ile | Gly | Phe | Phe | Gly | Ser | Ile | Phe | Phe | |
| | 105 | | | | | 110 | | | | | 115 | | | | | |

| ATC | ACC | GTC | ATC | AGC | ATT | GAT | AGG | TAC | CTG | GCC | ATC | GTC | CTG | GCC | GCC | 498 |
|---|---|---|---|---|---|---|---|---|---|---|---|---|---|---|---|---|
| Ile | Thr | Val | Ile | Ser | Ile | Asp | Arg | Tyr | Leu | Ala | Ile | Val | Leu | Ala | Ala | |
| 120 | | | | | 125 | | | | | 130 | | | | | 135 | |

| AAC | TCC | ATG | AAC | AAC | CGG | ACC | GTG | CAG | CAT | GGC | GTC | ACC | ATC | AGC | CTA | 546 |
|---|---|---|---|---|---|---|---|---|---|---|---|---|---|---|---|---|
| Asn | Ser | Met | Asn | Asn | Arg | Thr | Val | Gln | His | Gly | Val | Thr | Ile | Ser | Leu | |
| | | | | 140 | | | | | 145 | | | | | 150 | | |

| GGC | GTC | TGG | GCA | GCA | GCC | ATT | TTG | GTG | GCA | GCA | CCC | CAG | TTC | ATG | TTC | 594 |
|---|---|---|---|---|---|---|---|---|---|---|---|---|---|---|---|---|
| Gly | Val | Trp | Ala | Ala | Ala | Ile | Leu | Val | Ala | Ala | Pro | Gln | Phe | Met | Phe | |
| | | | 155 | | | | | 160 | | | | | 165 | | | |

| ACA | AAG | CAG | AAA | GAA | AAT | GAA | TGC | CTT | GGT | GAC | TAC | CCC | GAG | GTC | CTC | 642 |
|---|---|---|---|---|---|---|---|---|---|---|---|---|---|---|---|---|
| Thr | Lys | Gln | Lys | Glu | Asn | Glu | Cys | Leu | Gly | Asp | Tyr | Pro | Glu | Val | Leu | |
| | | 170 | | | | | 175 | | | | | 180 | | | | |

| CAG | GAA | ATC | TGG | CCC | GTG | CTC | CGC | AAT | GTG | GAA | ACA | AAT | TTT | CTT | GGC | 690 |
|---|---|---|---|---|---|---|---|---|---|---|---|---|---|---|---|---|
| Gln | Glu | Ile | Trp | Pro | Val | Leu | Arg | Asn | Val | Glu | Thr | Asn | Phe | Leu | Gly | |
| | 185 | | | | | 190 | | | | | 195 | | | | | |

| TTC | CTA | CTC | CCC | CTG | CTC | ATT | ATG | AGT | TAT | TGC | TAC | TTC | AGA | ATC | ATC | 738 |
|---|---|---|---|---|---|---|---|---|---|---|---|---|---|---|---|---|
| Phe | Leu | Leu | Pro | Leu | Leu | Ile | Met | Ser | Tyr | Cys | Tyr | Phe | Arg | Ile | Ile | |
| 200 | | | | | 205 | | | | | 210 | | | | | 215 | |

| CAG | ACG | CTG | TTT | TCC | TGC | AAG | AAC | CAC | AAG | AAA | GCC | AAA | GCC | ATT | AAA | 786 |
|---|---|---|---|---|---|---|---|---|---|---|---|---|---|---|---|---|
| Gln | Thr | Leu | Phe | Ser | Cys | Lys | Asn | His | Lys | Lys | Ala | Lys | Ala | Ile | Lys | |
| | | | | 220 | | | | | 225 | | | | | 230 | | |

| CTG | ATC | CTT | CTG | GTG | GTC | ATC | GTG | TTT | TTC | CTC | TTC | TGG | ACA | CCC | TAC | 834 |
|---|---|---|---|---|---|---|---|---|---|---|---|---|---|---|---|---|
| Leu | Ile | Leu | Leu | Val | Val | Ile | Val | Phe | Phe | Leu | Phe | Trp | Thr | Pro | Tyr | |
| | | | 235 | | | | | 240 | | | | | 245 | | | |

| AAC | GTT | ATG | ATT | TTC | CTG | GAG | ACG | CTT | AAG | CTC | TAT | GAC | TTC | TTT | CCC | 882 |
|---|---|---|---|---|---|---|---|---|---|---|---|---|---|---|---|---|
| Asn | Val | Met | Ile | Phe | Leu | Glu | Thr | Leu | Lys | Leu | Tyr | Asp | Phe | Phe | Pro | |
| | | 250 | | | | | 255 | | | | | 260 | | | | |

| AGT | TGT | GAC | ATG | AGG | AAG | GAT | CTG | AGG | CTG | GCC | CTC | AGT | GTG | ACT | GAG | 930 |
|---|---|---|---|---|---|---|---|---|---|---|---|---|---|---|---|---|
| Ser | Cys | Asp | Met | Arg | Lys | Asp | Leu | Arg | Leu | Ala | Leu | Ser | Val | Thr | Glu | |
| | 265 | | | | | 270 | | | | | 275 | | | | | |

| ACG | GTT | GCA | TTT | AGC | CAT | TGT | TGC | CTG | AAT | CCT | CTC | ATC | TAT | GCA | TTT | 978 |
|---|---|---|---|---|---|---|---|---|---|---|---|---|---|---|---|---|
| Thr | Val | Ala | Phe | Ser | His | Cys | Cys | Leu | Asn | Pro | Leu | Ile | Tyr | Ala | Phe | |
| 280 | | | | | 285 | | | | | 290 | | | | | 295 | |

| | | | | | | | | | | | | | | | | |
|---|---|---|---|---|---|---|---|---|---|---|---|---|---|---|---|---|
| GCT | GGG | GAG | AAG | TTC | AGA | AGA | TAC | CTT | TAC | CAC | CTG | TAT | GGG | AAA | TGC | 1026 |
| Ala | Gly | Glu | Lys | Phe | Arg | Arg | Tyr | Leu | Tyr | His | Leu | Tyr | Gly | Lys | Cys | |
| | | | 300 | | | | | 305 | | | | | 310 | | | |
| CTG | GCT | GTC | CTG | TGT | GGG | CGC | TCA | GTC | CAC | GTT | GAT | TTC | TCC | TCA | TCT | 1074 |
| Leu | Ala | Val | Leu | Cys | Gly | Arg | Ser | Val | His | Val | Asp | Phe | Ser | Ser | Ser | |
| | | | 315 | | | | | 320 | | | | | 325 | | | |
| GAA | TCA | CAA | AGG | AGC | AGG | CAT | GGA | AGT | GTT | CTG | AGC | AGC | AAT | TTT | ACT | 1122 |
| Glu | Ser | Gln | Arg | Ser | Arg | His | Gly | Ser | Val | Leu | Ser | Ser | Asn | Phe | Thr | |
| | | | 330 | | | | | 335 | | | | | 340 | | | |
| TAC | CAC | ACG | AGT | GAT | GGA | GAT | GCA | TTG | CTC | CTT | CTC | TGA | | | | 1161 |
| Tyr | His | Thr | Ser | Asp | Gly | Asp | Ala | Leu | Leu | Leu | Leu | | | | | |
| | | | 345 | | | | | 350 | | | | | 355 | | | |

( 2 ) INFORMATION FOR SEQ ID NO:32:

( i ) SEQUENCE CHARACTERISTICS:
        ( A ) LENGTH: 355 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Met Asp Gln Phe Pro Glu Ser Val Thr Glu Asn Phe Glu Tyr Asp Asp
 1               5                  10                  15

Leu Ala Glu Ala Cys Tyr Ile Gly Asp Ile Val Phe Gly Thr Val
                20                  25                  30

Phe Leu Ser Ile Phe Tyr Ser Val Ile Phe Ala Ile Gly Leu Val Gly
            35                  40                  45

Asn Leu Leu Val Val Phe Ala Leu Thr Asn Ser Lys Lys Pro Lys Ser
        50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
                100                 105                 110

Phe Phe Gly Ser Ile Phe Phe Ile Thr Val Ile Ser Ile Asp Arg Tyr
            115                 120                 125

Leu Ala Ile Val Leu Ala Ala Asn Ser Met Asn Asn Arg Thr Val Gln
        130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
        210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
```

|  | 275 |  |  |  | 280 |  |  |  |  | 285 |  |  |  |
|---|---|---|---|---|---|---|---|---|---|---|---|---|---|

Asn Pro Leu Ile Tyr Ala Phe Ala Gly Glu Lys Phe Arg Arg Tyr Leu
    290                            295                                300

Tyr His Leu Tyr Gly Lys Cys Leu Ala Val Leu Cys Gly Arg Ser Val
305                                  310                                315                            320

His Val Asp Phe Ser Ser Ser Glu Ser Gln Arg Ser Arg His Gly Ser
                          325                                330                            335

Val Leu Ser Ser Asn Phe Thr Tyr His Thr Ser Asp Gly Asp Ala Leu
                340                                345                              350

Leu Leu Leu
        355

( 2 ) INFORMATION FOR SEQ ID NO:33:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

TGGGTGGATA AAGAAGCATC TC                                                                                        22

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

AACACTCATG CAAGTGAGCA                                                                                            20

( 2 ) INFORMATION FOR SEQ ID NO:35:

( i ) SEQUENCE CHARACTERISTICS:
        ( A ) LENGTH: 720 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 258..719

( x i ) SEQUENCE DESCRIPTION: SEQ ID NO:35:

GAATTCTTTT TGTATTCTAA TACAGTTCAA ATCAGTGTGG CTGGTTCATT TCAACTCCTT    60

CACTACCAAA CTAGGAGGCA GGGACTGGCT TCAGTTTTTC TGCCTTCTCT TTTTCACTGA   120

TGACCAGGGT ATAAAGATAT CTGCTGCATC GAACTTTAAA CTTCACATTG TCCTTATTTT   180

TCTTGATCTT GACAGATTCA GCATCCTTTC ATTGGGCTGT GAACAGAAAG TCCAGATTTG   240

GAATCTGCTC TTTGGTG ATG GAC CCA GAA GAA ACT TCA GTT TAT TTG GAT    290
                            Met Asp Pro Glu Glu Thr Ser Val Tyr Leu Asp
                             1                    5                      10

TAT TAC TAT GCT ACG AGC CCA AAC TCT GAC ATC AGG GAG ACC CAC TCC   338
Tyr Tyr Tyr Ala Thr Ser Pro Asn Ser Asp Ile Arg Glu Thr His Ser
               15                      20                        25

| | | | | | | | | | | | | | | | | |
|---|---|---|---|---|---|---|---|---|---|---|---|---|---|---|---|---|
| CAT | GTT | CCT | TAC | ACC | TCT | GTC | TTC | CTT | CCA | GTC | TTT | TAC | ACA | GCT | GTG | 386 |
| His | Val | Pro | Tyr | Thr | Ser | Val | Phe | Leu | Pro | Val | Phe | Tyr | Thr | Ala | Val | |
| | | 30 | | | | 35 | | | | | 40 | | | | | |
| TTC | CTG | ACT | GGA | GTG | CTG | GGG | AAC | CTT | GTT | CTC | ATG | GGA | GCG | TTG | CAT | 434 |
| Phe | Leu | Thr | Gly | Val | Leu | Gly | Asn | Leu | Val | Leu | Met | Gly | Ala | Leu | His | |
| | 45 | | | | 50 | | | | | 55 | | | | | | |
| TTC | AAA | CCC | GGC | AGC | CGA | AGA | CTG | ATC | GAC | ATC | TTT | ATC | ATC | AAT | CTG | 482 |
| Phe | Lys | Pro | Gly | Ser | Arg | Arg | Leu | Ile | Asp | Ile | Phe | Ile | Ile | Asn | Leu | |
| 60 | | | | | 65 | | | | 70 | | | | | | 75 | |
| GCT | GCC | TCT | GAC | TTC | ATT | TTT | CTT | GTC | ACA | TTG | CCT | CTC | TGG | GTG | GAT | 530 |
| Ala | Ala | Ser | Asp | Phe | Ile | Phe | Leu | Val | Thr | Leu | Pro | Leu | Trp | Val | Asp | |
| | | | | 80 | | | | | 85 | | | | | 90 | | |
| AAA | GAA | GCA | TCT | CTA | GGA | CTG | TGG | CGG | ACG | GGC | TCC | TTC | CTG | TGC | AAA | 578 |
| Lys | Glu | Ala | Ser | Leu | Gly | Leu | Trp | Arg | Thr | Gly | Ser | Phe | Leu | Cys | Lys | |
| | | | 95 | | | | 100 | | | | | 105 | | | | |
| GGG | AGC | TCC | TAC | ATG | ATC | TCC | GTC | AAT | ATG | CAC | TGC | AGT | GTC | CTC | CTG | 626 |
| Gly | Ser | Ser | Tyr | Met | Ile | Ser | Val | Asn | Met | His | Cys | Ser | Val | Leu | Leu | |
| | | 110 | | | | 115 | | | | | 120 | | | | | |
| CTC | ACT | TGC | ATG | AGT | GTT | GAC | CGC | TAC | CTG | GCC | ATT | GTG | TGG | CCA | GTC | 674 |
| Leu | Thr | Cys | Met | Ser | Val | Asp | Arg | Tyr | Leu | Ala | Ile | Val | Trp | Pro | Val | |
| | 125 | | | | 130 | | | | | 135 | | | | | | |
| GTA | TCC | AGG | AAA | TTC | AGA | AGG | ACA | GAC | TGT | GCA | TAT | GTA | GTC | TGT | G | 720 |
| Val | Ser | Arg | Lys | Phe | Arg | Arg | Thr | Asp | Cys | Ala | Tyr | Val | Val | Cys | | |
| 140 | | | | 145 | | | | | 150 | | | | | | | |

( 2 ) INFORMATION FOR SEQ ID NO:36:

( i ) SEQUENCE CHARACTERISTICS:
        ( A ) LENGTH: 154 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| | | | | | | | | | | | | | | |
|---|---|---|---|---|---|---|---|---|---|---|---|---|---|---|
| Met | Asp | Pro | Glu | Glu | Thr | Ser | Val | Tyr | Leu | Asp | Tyr | Tyr | Ala | Thr |
| 1 | | | | 5 | | | | | 10 | | | | | 15 |
| Ser | Pro | Asn | Ser | Asp | Ile | Arg | Glu | Thr | His | Ser | His | Val | Pro | Tyr | Thr |
| | | | 20 | | | | | 25 | | | | | 30 | | |
| Ser | Val | Phe | Leu | Pro | Val | Phe | Tyr | Thr | Ala | Val | Phe | Leu | Thr | Gly | Val |
| | | | 35 | | | | 40 | | | | | 45 | | | |
| Leu | Gly | Asn | Leu | Val | Leu | Met | Gly | Ala | Leu | His | Phe | Lys | Pro | Gly | Ser |
| | 50 | | | | | 55 | | | | | 60 | | | | |
| Arg | Arg | Leu | Ile | Asp | Ile | Phe | Ile | Ile | Asn | Leu | Ala | Ala | Ser | Asp | Phe |
| 65 | | | | | 70 | | | | | 75 | | | | | 80 |
| Ile | Phe | Leu | Val | Thr | Leu | Pro | Leu | Trp | Val | Asp | Lys | Glu | Ala | Ser | Leu |
| | | | | 85 | | | | | 90 | | | | | 95 | |
| Gly | Leu | Trp | Arg | Thr | Gly | Ser | Phe | Leu | Cys | Lys | Gly | Ser | Ser | Tyr | Met |
| | | | 100 | | | | | 105 | | | | | 110 | | |
| Ile | Ser | Val | Asn | Met | His | Cys | Ser | Val | Leu | Leu | Leu | Thr | Cys | Met | Ser |
| | | 115 | | | | | 120 | | | | | 125 | | | |
| Val | Asp | Arg | Tyr | Leu | Ala | Ile | Val | Trp | Pro | Val | Val | Ser | Arg | Lys | Phe |
| | 130 | | | | | 135 | | | | | 140 | | | | |
| Arg | Arg | Thr | Asp | Cys | Ala | Tyr | Val | Val | Cys | | | | | | |
| 145 | | | | | 150 | | | | | | | | | | |

( 2 ) INFORMATION FOR SEQ ID NO:37:

( i ) SEQUENCE CHARACTERISTICS:
        ( A ) LENGTH: 21 base pairs
        ( B ) TYPE: nucleic acid

```
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

CTACACGTAC CGGGACTATG A                                                        21

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

AGAAGACGCT GGCGTACATG                                                          20

( 2 ) INFORMATION FOR SEQ ID NO:39:

( i ) SEQUENCE CHARACTERISTICS:
        ( A ) LENGTH: 1872 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 202..1341

( x i ) SEQUENCE DESCRIPTION: SEQ ID NO:39:
```

```
CTGCAGGAGA CAGGCTTCCT CCAGGGTCTG GAGAACCCAG AGGCAGCTCC TCCTGAGTGC      60

TGGGAAGGAC TCTGGGCATC TTCAGCCCTT CTTACTCTCT GAGGCTCAAG CCAGAAATTC     120

AGGCTGCTTG CAGAGTGGGT GACAGAGCCA CGGAGCTGGT GTCCCTGGGA CCCTCTGCCC     180

GTCTTCTCTC CACTCCCCAG C ATG GAG GAA GGT GGT GAT TTT GAC AAC TAC       231
                        Met Glu Glu Gly Gly Asp Phe Asp Asn Tyr
                         1               5                   10

TAT GGG GCA GAC AAC CAG TCT GAG TGT GAG TAC ACA GAC TGG AAA TCC       279
Tyr Gly Ala Asp Asn Gln Ser Glu Cys Glu Tyr Thr Asp Trp Lys Ser
            15                  20                  25

TCG GGG GCC CTC ATC CCT GCC ATC TAC ATG TTG GTC TTC CTC CTG GGC       327
Ser Gly Ala Leu Ile Pro Ala Ile Tyr Met Leu Val Phe Leu Leu Gly
        30                  35                  40

ACC ACG GGA AAC GGT CTG GTG CTC TGG ACC GTG TTT CGG AGC AGC CGG       375
Thr Thr Gly Asn Gly Leu Val Leu Trp Thr Val Phe Arg Ser Ser Arg
        45                  50                  55

GAG AAG AGG CGC TCA GCT GAT ATC TTC ATT GCT AGC CTG GCG GTG GCT       423
Glu Lys Arg Arg Ser Ala Asp Ile Phe Ile Ala Ser Leu Ala Val Ala
    60                  65                  70

GAC CTG ACC TTC GTG GTG ACG CTG CCC CTG TGG GCT ACC TAC ACG TAC       471
Asp Leu Thr Phe Val Val Thr Leu Pro Leu Trp Ala Thr Tyr Thr Tyr
75                  80                  85                  90

CGG GAC TAT GAC TGG CCC TTT GGG ACC TTC TTC TGC AAG CTC AGC AGC       519
Arg Asp Tyr Asp Trp Pro Phe Gly Thr Phe Phe Cys Lys Leu Ser Ser
                95                 100                 105

TAC CTC ATC TTC GTC AAC ATG TAC GCC AGC GTC TTC TGC CTC ACC GGC       567
Tyr Leu Ile Phe Val Asn Met Tyr Ala Ser Val Phe Cys Leu Thr Gly
            110                 115                 120

CTC AGC TTC GAC CGC TAC CTG GCC ATC GTG AGG CCA GTG GCC AAT GCT       615
```

|       |       |       |       |       |       |       |       |       |       |       |       |       |       |       |      |
|-------|-------|-------|-------|-------|-------|-------|-------|-------|-------|-------|-------|-------|-------|-------|------|
| Leu   | Ser   | Phe   | Asp   | Arg   | Tyr   | Leu   | Ala   | Ile   | Val   | Arg   | Pro   | Val   | Ala   | Asn   | Ala  |
|       |       | 125   |       |       |       |       | 130   |       |       |       |       | 135   |       |       |      |

| CGG | CTG | AGG | CTG | CGG | GTC | AGC | GGG | GCC | GTG | GCC | ACG | GCA | GTT | CTT | TGG | 663 |
|-----|-----|-----|-----|-----|-----|-----|-----|-----|-----|-----|-----|-----|-----|-----|-----|-----|
| Arg | Leu | Arg | Leu | Arg | Val | Ser | Gly | Ala | Val | Ala | Thr | Ala | Val | Leu | Trp |     |
|     | 140 |     |     |     |     | 145 |     |     |     |     | 150 |     |     |     |     |     |

| GTG | CTG | GCC | GCC | CTC | CTG | GCC | ATG | CCT | GTC | ATG | GTG | TTA | CGC | ACC | ACC | 711 |
|-----|-----|-----|-----|-----|-----|-----|-----|-----|-----|-----|-----|-----|-----|-----|-----|-----|
| Val | Leu | Ala | Ala | Leu | Leu | Ala | Met | Pro | Val | Met | Val | Leu | Arg | Thr | Thr |     |
| 155 |     |     |     |     | 160 |     |     |     |     | 165 |     |     |     |     | 170 |     |

| GGG | GAC | TTG | GAG | AAC | ACC | ACT | AAG | GTG | CAG | TGC | TAC | ATG | GAC | TAC | TCC | 759 |
|-----|-----|-----|-----|-----|-----|-----|-----|-----|-----|-----|-----|-----|-----|-----|-----|-----|
| Gly | Asp | Leu | Glu | Asn | Thr | Thr | Lys | Val | Gln | Cys | Tyr | Met | Asp | Tyr | Ser |     |
|     |     |     |     | 175 |     |     |     |     | 180 |     |     |     |     | 185 |     |     |

| ATG | GTG | GCC | ACT | GTG | AGC | TCA | GAG | TGG | GCC | TGG | GAG | GTG | GGC | CTT | GGG | 807 |
|-----|-----|-----|-----|-----|-----|-----|-----|-----|-----|-----|-----|-----|-----|-----|-----|-----|
| Met | Val | Ala | Thr | Val | Ser | Ser | Glu | Trp | Ala | Trp | Glu | Val | Gly | Leu | Gly |     |
|     |     |     | 190 |     |     |     |     | 195 |     |     |     |     | 200 |     |     |     |

| GTC | TCG | TCC | ACC | ACC | GTG | GGC | TTT | GTG | GTG | CCC | TTC | ACC | ATC | ATG | CTG | 855 |
|-----|-----|-----|-----|-----|-----|-----|-----|-----|-----|-----|-----|-----|-----|-----|-----|-----|
| Val | Ser | Ser | Thr | Thr | Val | Gly | Phe | Val | Val | Pro | Phe | Thr | Ile | Met | Leu |     |
|     |     | 205 |     |     |     |     | 210 |     |     |     |     | 215 |     |     |     |     |

| ACC | TGT | TAC | TTC | TTC | ATC | GCC | CAA | ACC | ATC | GCT | GGC | CAC | TTC | CGC | AAG | 903 |
|-----|-----|-----|-----|-----|-----|-----|-----|-----|-----|-----|-----|-----|-----|-----|-----|-----|
| Thr | Cys | Tyr | Phe | Phe | Ile | Ala | Gln | Thr | Ile | Ala | Gly | His | Phe | Arg | Lys |     |
|     | 220 |     |     |     |     | 225 |     |     |     |     | 230 |     |     |     |     |     |

| GAA | CGC | ATC | GAG | GGC | CTG | CGG | AAG | CGG | CGC | CGG | CTG | CTC | AGC | ATC | ATC | 951 |
|-----|-----|-----|-----|-----|-----|-----|-----|-----|-----|-----|-----|-----|-----|-----|-----|-----|
| Glu | Arg | Ile | Glu | Gly | Leu | Arg | Lys | Arg | Arg | Arg | Leu | Leu | Ser | Ile | Ile |     |
| 235 |     |     |     |     | 240 |     |     |     |     | 245 |     |     |     |     | 250 |     |

| GTG | GTG | CTG | GTG | GTG | ACC | TTT | GCC | CTG | TGC | TGG | ATG | CCC | TAC | CAC | CTG | 999 |
|-----|-----|-----|-----|-----|-----|-----|-----|-----|-----|-----|-----|-----|-----|-----|-----|-----|
| Val | Val | Leu | Val | Val | Thr | Phe | Ala | Leu | Cys | Trp | Met | Pro | Tyr | His | Leu |     |
|     |     |     |     | 255 |     |     |     |     | 260 |     |     |     |     | 265 |     |     |

| GTG | AAG | ACG | CTG | TAC | ATG | CTG | GGC | AGC | CTG | CTG | CAC | TGG | CCC | TGT | GAC | 1047 |
|-----|-----|-----|-----|-----|-----|-----|-----|-----|-----|-----|-----|-----|-----|-----|-----|------|
| Val | Lys | Thr | Leu | Tyr | Met | Leu | Gly | Ser | Leu | Leu | His | Trp | Pro | Cys | Asp |      |
|     |     |     | 270 |     |     |     |     | 275 |     |     |     |     | 280 |     |     |      |

| TTT | GAC | CTC | TTC | CTC | ATG | AAC | ATC | TTC | CCC | TAC | TGC | ACC | TGC | ATC | AGC | 1095 |
|-----|-----|-----|-----|-----|-----|-----|-----|-----|-----|-----|-----|-----|-----|-----|-----|------|
| Phe | Asp | Leu | Phe | Leu | Met | Asn | Ile | Phe | Pro | Tyr | Cys | Thr | Cys | Ile | Ser |      |
|     |     | 285 |     |     |     |     | 290 |     |     |     |     | 295 |     |     |     |      |

| TAC | GTC | AAC | AGC | TGC | CTC | AAC | CCC | TTC | CTC | TAT | GCC | TTT | TTC | GAC | CCC | 1143 |
|-----|-----|-----|-----|-----|-----|-----|-----|-----|-----|-----|-----|-----|-----|-----|-----|------|
| Tyr | Val | Asn | Ser | Cys | Leu | Asn | Pro | Phe | Leu | Tyr | Ala | Phe | Phe | Asp | Pro |      |
|     | 300 |     |     |     |     | 305 |     |     |     |     | 310 |     |     |     |     |      |

| CGC | TTC | CGC | CAG | GCC | TGC | ACC | TCC | ATG | CTC | TGC | TGT | GGC | CAG | AGC | AGG | 1191 |
|-----|-----|-----|-----|-----|-----|-----|-----|-----|-----|-----|-----|-----|-----|-----|-----|------|
| Arg | Phe | Arg | Gln | Ala | Cys | Thr | Ser | Met | Leu | Cys | Cys | Gly | Gln | Ser | Arg |      |
| 315 |     |     |     |     | 320 |     |     |     |     | 325 |     |     |     |     | 330 |      |

| TGC | GCA | GGC | ACC | TCC | CAC | AGC | AGC | AGT | GGG | GAG | AAG | TCA | GCC | AGC | TAC | 1239 |
|-----|-----|-----|-----|-----|-----|-----|-----|-----|-----|-----|-----|-----|-----|-----|-----|------|
| Cys | Ala | Gly | Thr | Ser | His | Ser | Ser | Ser | Gly | Glu | Lys | Ser | Ala | Ser | Tyr |      |
|     |     |     |     | 335 |     |     |     |     | 340 |     |     |     |     | 345 |     |      |

| TCT | TCG | GGG | CAC | AGC | CAG | GGG | CCC | GGC | CCC | AAC | ATG | GGC | AAG | GGT | GGA | 1287 |
|-----|-----|-----|-----|-----|-----|-----|-----|-----|-----|-----|-----|-----|-----|-----|-----|------|
| Ser | Ser | Gly | His | Ser | Gln | Gly | Pro | Gly | Pro | Asn | Met | Gly | Lys | Gly | Gly |      |
|     |     |     | 350 |     |     |     |     | 355 |     |     |     |     | 360 |     |     |      |

| GAA | CAG | ATG | CAC | GAG | AAA | TCC | ATC | CCC | TAC | AGC | CAG | GAG | ACC | CTT | GTG | 1335 |
|-----|-----|-----|-----|-----|-----|-----|-----|-----|-----|-----|-----|-----|-----|-----|-----|------|
| Glu | Gln | Met | His | Glu | Lys | Ser | Ile | Pro | Tyr | Ser | Gln | Glu | Thr | Leu | Val |      |
|     |     | 365 |     |     |     |     | 370 |     |     |     |     | 375 |     |     |     |      |

| GTT | GAC | TAGGGCTGGG | AGCAGAGAGA | AGCCTGGCGC | CCTCGGCCCT | CCCCGGCCTT | 1391 |
|-----|-----|------------|------------|------------|------------|------------|------|
| Val | Asp |            |            |            |            |            |      |
|     | 380 |            |            |            |            |            |      |

| TGCCCTTGCT | TTCTGAAAAT | CAGGTAGTGT | GGCTACTCCC | TTGTCCTATG | CACATCCTTT | 1451 |
|------------|------------|------------|------------|------------|------------|------|
| AACTGTCCCC | TGATTCTGCC | CGCCCTGTCC | TCCTCTACTG | CTTTATTCTT | TCTCAGAGGT | 1511 |
| TTGTGGTTTA | GGGGAAAGAG | ACTGGGCTCT | ACAGACCTGA | CCCTGCACAA | GCCATTTAAT | 1571 |
| CTCACTCAGC | CTCAGTTTCT | CCATTGGTAT | GAAATGGGGG | AAAGTCATAT | TGATCCTAAA | 1631 |
| ATGTTGAAGC | CTGAGTCTGG | ACGCAGTAAA | AGCTTGTTTC | CCTCTGCTGC | TTTCTTAGAT | 1691 |
| CTGCAATCGT | CTTTCCTCCC | CTCTTTCCTT | GTAGTTTTTC | CCCNCACNAC | TCTCTGCACG | 1751 |
| TGCCGCTCNT | TATCCCNGCT | TCTGGCACCA | ATCCCCTCCT | ACAGCTCGTC | CCCCTCNCTC | 1811 |

```
GATCCATCCT TCTCGCCTGT CTACTTTCTT GTTCTGAAGG GCTACTAAGG GTTAAGGATC      1871
C                                                                      1872
```

( 2 ) INFORMATION FOR SEQ ID NO:40:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Met Glu Glu Gly Gly Asp Phe Asp Asn Tyr Tyr Gly Ala Asp Asn Gln
  1               5                  10                  15

Ser Glu Cys Glu Tyr Thr Asp Trp Lys Ser Ser Gly Ala Leu Ile Pro
             20                  25                  30

Ala Ile Tyr Met Leu Val Phe Leu Leu Gly Thr Thr Gly Asn Gly Leu
             35                  40                  45

Val Leu Trp Thr Val Phe Arg Ser Ser Arg Glu Lys Arg Arg Ser Ala
 50                  55                  60

Asp Ile Phe Ile Ala Ser Leu Ala Val Ala Asp Leu Thr Phe Val Val
 65                  70                  75                  80

Thr Leu Pro Leu Trp Ala Thr Tyr Thr Tyr Arg Asp Tyr Asp Trp Pro
                 85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
        130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335
```

| | | | | | | | | | | | | | | |
|---|---|---|---|---|---|---|---|---|---|---|---|---|---|---|
| Ser | Ser | Ser | Gly<br>340 | Glu | Lys | Ser | Ala | Ser<br>345 | Tyr | Ser | Ser | Gly | His<br>350 | Ser Gln |
| Gly | Pro | Gly<br>355 | Pro | Asn | Met | Gly | Lys<br>360 | Gly | Gly | Glu | Gln | Met<br>365 | His | Glu Lys |
| Ser | Ile<br>370 | Pro | Tyr | Ser | Gln<br>375 | Glu | Thr | Leu | Val | Val<br>380 | Asp | | | |

( 2 ) INFORMATION FOR SEQ ID NO:41:

( i ) SEQUENCE CHARACTERISTICS:
        ( A ) LENGTH: 2098 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 551..1681

( x i ) SEQUENCE DESCRIPTION: SEQ ID NO:41:

```
AGTTTCCTGG GAGCGGCCGT GGTTGTGGTG GTGGTGGGAC AGTGTGCAGC CATGAAAGAA    60

GGTGCAAAGG AATCTCCAAA GAAAGCCTGA CCAGCGTAAA AAGTTGGGAG GCTTTGTCCT    120

TGTCACTTGT CCACTAAACT CCTCCCCTCC CTGTTATCCT GGTTGACCCT GGGCATCTCT    180

GGGGACAGTA GGCAGGTGAT TGGGAAAGTT AATGGGATTG AGGGGCTGAG GGCTGGCAGG    240

GGGCAAAAAG ACTGGCCTTT CAAGGGGTGC AGCATTGGTA GGAACTCTGT TTGGTTCTGG    300

GCTTTAGGGT CTCCTAAGGG AGGAGACTGA AAAGGTCTGG AAATGCTGCT GCTGCTGTGG    360

TCACTGTATA TTTTGCAATT GGGTCTGTGG ACAGGAAGGG GCCGCATGAC CCAGTTAGGA    420

AACTAGTCTT TGTACTCAAC CAGATCCCTT TAAGTTGTCA GTCTGCAGCG ATGGGGGCAG    480

TATATTTCAG GGGGACCTCT GATGCTGCTG ACCCTGGAGA TAGACTAGAG TTCTCAGCCT    540
```

| | | | | | | | | | | | | | |
|---|---|---|---|---|---|---|---|---|---|---|---|---|---|
| AGGTGTGTCC | ATG<br>Met<br>1 | GCG<br>Ala | TCA<br>Ser | GGA<br>Gly | AAC<br>Asn | CCT<br>Pro<br>5 | TGG<br>Trp | TCC<br>Ser | TCT<br>Ser | ACT<br>Thr | CTC<br>Leu | ATG<br>Met<br>10 | CGT<br>Arg | 589 |
| GTG<br>Val | TCC<br>Ser<br>15 | GCC<br>Ala | CTC<br>Leu | ACT<br>Thr | CTC<br>Leu | CAG<br>Gln<br>20 | GTC<br>Val | CTC<br>Leu | CCG<br>Pro | ACG<br>Thr | GCC<br>Ala<br>25 | ATG<br>Met | AAC<br>Asn | ACT<br>Thr | ACA<br>Thr | 637 |
| TCT<br>Ser | TCT<br>Ser<br>30 | GCA<br>Ala | GCA<br>Ala | CCC<br>Pro | CCC<br>Pro<br>35 | TCA<br>Ser | CTA<br>Leu | GGT<br>Gly | GTA<br>Val | GAG<br>Glu<br>40 | TTC<br>Phe | ATC<br>Ile | TCT<br>Ser | CTG<br>Leu | CTG<br>Leu<br>45 | 685 |
| GCT<br>Ala | ATC<br>Ile | ATC<br>Ile | CTG<br>Leu | CTG<br>Leu<br>50 | TCA<br>Ser | GTG<br>Val | GCG<br>Ala | CTG<br>Leu | GCT<br>Ala<br>55 | GTG<br>Val | GGG<br>Gly | CTT<br>Leu | CCC<br>Pro | GGC<br>Gly<br>60 | AAC<br>Asn | 733 |
| AGC<br>Ser | TTT<br>Phe | GTG<br>Val | GTG<br>Val<br>65 | TGG<br>Trp | AGT<br>Ser | ATC<br>Ile | CTG<br>Leu | AAA<br>Lys<br>70 | AGG<br>Arg | ATG<br>Met | CAG<br>Gln | AAG<br>Lys | CGC<br>Arg<br>75 | TCT<br>Ser | GTC<br>Val | 781 |
| ACT<br>Thr | GCC<br>Ala | CTG<br>Leu<br>80 | ATG<br>Met | GTG<br>Val | CTG<br>Leu | AAC<br>Asn | CTG<br>Leu<br>85 | GCC<br>Ala | CTG<br>Leu | GCC<br>Ala | GAC<br>Asp | CTG<br>Leu<br>90 | GCC<br>Ala | GTA<br>Val | TTG<br>Leu | 829 |
| CTC<br>Leu | ACT<br>Thr<br>95 | GCT<br>Ala | CCC<br>Pro | TTT<br>Phe | TTC<br>Phe<br>100 | CTT<br>Leu | CAC<br>His | TTC<br>Phe | CTG<br>Leu | GCC<br>Ala<br>105 | CAA<br>Gln | GGC<br>Gly | ACC<br>Thr | TGG<br>Trp | AGT<br>Ser | 877 |
| TTT<br>Phe<br>110 | GGA<br>Gly | CTG<br>Leu | GCT<br>Ala | GGT<br>Gly | TGC<br>Cys<br>115 | CGC<br>Arg | CTG<br>Leu | TGT<br>Cys | CAC<br>His | TAT<br>Tyr<br>120 | GTC<br>Val | TGC<br>Cys | GGA<br>Gly | GTC<br>Val | AGC<br>Ser<br>125 | 925 |
| ATG<br>Met | TAC<br>Tyr | GCC<br>Ala | AGC<br>Ser<br>130 | GTC<br>Val | CTG<br>Leu | CTT<br>Leu | ATC<br>Ile | ACG<br>Thr<br>135 | GCC<br>Ala | ATG<br>Met | AGT<br>Ser | CTA<br>Leu | GAC<br>Asp<br>140 | CGC<br>Arg | TCA<br>Ser | 973 |

-continued

| | | | | | | | | | | | | | | | | |
|---|---|---|---|---|---|---|---|---|---|---|---|---|---|---|---|---|
| CTG | GCG | GTG | GCC | CGC | CCC | TTT | GTG | TCC | CAG | AAG | CTA | CGC | ACC | AAG | GCG | 1021 |
| Leu | Ala | Val | Ala | Arg | Pro | Phe | Val | Ser | Gln | Lys | Leu | Arg | Thr | Lys | Ala | |
| | | | 145 | | | | | 150 | | | | | 155 | | | |
| ATG | GCC | CGG | CGG | GTG | CTG | GCA | GGC | ATC | TGG | GTG | TTG | TCC | TTT | CTG | CTG | 1069 |
| Met | Ala | Arg | Arg | Val | Leu | Ala | Gly | Ile | Trp | Val | Leu | Ser | Phe | Leu | Leu | |
| | | 160 | | | | | 165 | | | | | 170 | | | | |
| GCC | ACA | CCC | GTC | CTC | GCG | TAC | CGC | ACA | GTA | GTG | CCC | TGG | AAA | ACG | AAC | 1117 |
| Ala | Thr | Pro | Val | Leu | Ala | Tyr | Arg | Thr | Val | Val | Pro | Trp | Lys | Thr | Asn | |
| | 175 | | | | | 180 | | | | | 185 | | | | | |
| ATG | AGC | CTG | TGC | TTC | CCG | CGG | TAC | CCC | AGC | GAA | GGG | CAC | CGG | GCC | TTC | 1165 |
| Met | Ser | Leu | Cys | Phe | Pro | Arg | Tyr | Pro | Ser | Glu | Gly | His | Arg | Ala | Phe | |
| 190 | | | | | 195 | | | | | 200 | | | | | 205 | |
| CAT | CTA | ATC | TTC | GAG | GCT | GTC | ACG | GGC | TTC | CTG | CTG | CCC | TTC | CTG | GCT | 1213 |
| His | Leu | Ile | Phe | Glu | Ala | Val | Thr | Gly | Phe | Leu | Leu | Pro | Phe | Leu | Ala | |
| | | | | 210 | | | | | 215 | | | | | 220 | | |
| GTG | GTG | GCC | AGC | TAC | TCG | GAC | ATA | GGG | CGT | CGG | CTA | CAG | GCC | CGG | CGC | 1261 |
| Val | Val | Ala | Ser | Tyr | Ser | Asp | Ile | Gly | Arg | Arg | Leu | Gln | Ala | Arg | Arg | |
| | | | 225 | | | | | 230 | | | | | 235 | | | |
| TTC | CGC | CGC | AGC | CGC | CGC | ACC | GGC | CGC | CTG | GTG | GTG | CTC | ATC | ATC | CTG | 1309 |
| Phe | Arg | Arg | Ser | Arg | Arg | Thr | Gly | Arg | Leu | Val | Val | Leu | Ile | Ile | Leu | |
| | | 240 | | | | | 245 | | | | | 250 | | | | |
| ACC | TTC | GCC | GCC | TTC | TGG | CTG | CCC | TAC | CAC | GTG | GTG | AAC | CTG | GCT | GAG | 1357 |
| Thr | Phe | Ala | Ala | Phe | Trp | Leu | Pro | Tyr | His | Val | Val | Asn | Leu | Ala | Glu | |
| | 255 | | | | | 260 | | | | | 265 | | | | | |
| GCC | CGC | CGC | GCG | CTG | GCC | GGC | CAG | GCC | GCC | GGG | TTA | GGG | CTC | GTG | GGG | 1405 |
| Ala | Arg | Arg | Ala | Leu | Ala | Gly | Gln | Ala | Ala | Gly | Leu | Gly | Leu | Val | Gly | |
| 270 | | | | | 275 | | | | | 280 | | | | | 285 | |
| AAG | CGG | CTG | AGC | CTG | GCC | CGC | AAC | GTG | CTC | ATC | GCA | CTC | GCC | TTC | CTG | 1453 |
| Lys | Arg | Leu | Ser | Leu | Ala | Arg | Asn | Val | Leu | Ile | Ala | Leu | Ala | Phe | Leu | |
| | | | 290 | | | | | 295 | | | | | 300 | | | |
| AGC | AGC | AGC | GTG | AAC | CCC | GTG | CTG | TAC | GCG | TGC | GCC | GGC | GGC | GGC | CTG | 1501 |
| Ser | Ser | Ser | Val | Asn | Pro | Val | Leu | Tyr | Ala | Cys | Ala | Gly | Gly | Gly | Leu | |
| | | | 305 | | | | | 310 | | | | | 315 | | | |
| CTG | CGC | TCG | GCG | GGC | GTG | GGC | TTC | GTC | GCC | AAG | CTG | CTG | GAG | GGC | ACG | 1549 |
| Leu | Arg | Ser | Ala | Gly | Val | Gly | Phe | Val | Ala | Lys | Leu | Leu | Glu | Gly | Thr | |
| | | 320 | | | | | 325 | | | | | 330 | | | | |
| GGC | TCC | GAG | GCG | TCC | AGC | ACG | CGC | CGC | GGG | GGC | AGC | CTG | GGC | CAG | ACC | 1597 |
| Gly | Ser | Glu | Ala | Ser | Ser | Thr | Arg | Arg | Gly | Gly | Ser | Leu | Gly | Gln | Thr | |
| | 335 | | | | | 340 | | | | | 345 | | | | | |
| GCT | AGG | AGC | GGC | CCC | GCC | GCT | CTG | GAG | CCC | GGC | CCT | TCC | GAG | AGC | CTC | 1645 |
| Ala | Arg | Ser | Gly | Pro | Ala | Ala | Leu | Glu | Pro | Gly | Pro | Ser | Glu | Ser | Leu | |
| 350 | | | | | 355 | | | | | 360 | | | | | 365 | |
| ACT | GCC | TCC | AGC | CCT | CTC | AAG | TTA | AAC | GAA | CTG | AAC | TAGGCCTGGT | | | | 1691 |
| Thr | Ala | Ser | Ser | Pro | Leu | Lys | Leu | Asn | Glu | Leu | Asn | | | | | |
| | | | | 370 | | | | | 375 | | | | | | | |

GGAAGGAGGC GCACTTTCCT CCTGGCAGAA TCGTAGCTCT GAGCCAGTTC AGTACCTGGA 1751

GGAGGAGCAG GGGCGTGGAG GGCGTGGAGG GCGTGGGAGC GTGGGAGGCG GGAGTGGAGT 1811

GGAAGAAGAG GGAGAGATGG AGCAAAGTGA GGGCCGAGTG AGAGCGTGCT CCAGCCTGGC 1871

TCCCACAGGC AGCTTTAACC ATTAAAACTG AAGTCTGAAA TTTGGTCAAC CTTGTGAGTG 1931

GGGTACATGT GCTGTGGGTA TCGGGGTGCT CGTGGGCGCC CTGGTGGGGC CCTCTCGGT 1991

AGTTGAGAGT CACGTCCTTT AGTTCCCCAT GATTTACAAT TTTGGAAGGG ACACAAAGAA 2051

ACATAGACTG CCCCCATCCC AGATGATTCC GAGTACATAG TCTGCAG 2098

( 2 ) INFORMATION FOR SEQ ID NO:42:

( i ) SEQUENCE CHARACTERISTICS:
        ( A ) LENGTH: 377 amino acids
        ( B ) TYPE: amino acid (D) TOPOLOGY: linear (ii) MOLECULE TYPE: protein (xi) SEQUENCE DESCRIPTION: SEQ ID NO:42:

| Met | Ala | Ser | Gly | Asn | Pro | Trp | Ser | Ser | Thr | Leu | Met | Arg | Val | Ser | Ala |
| 1 | | | | 5 | | | | | 10 | | | | | 15 | |

| Leu | Thr | Leu | Gln | Val | Leu | Pro | Thr | Ala | Met | Asn | Thr | Thr | Ser | Ser | Ala |
| | | | 20 | | | | | 25 | | | | | 30 | | |

| Ala | Pro | Pro | Ser | Leu | Gly | Val | Glu | Phe | Ile | Ser | Leu | Leu | Ala | Ile | Ile |
| | | 35 | | | | | 40 | | | | | 45 | | | |

| Leu | Leu | Ser | Val | Ala | Leu | Ala | Val | Gly | Leu | Pro | Gly | Asn | Ser | Phe | Val |
| | 50 | | | | | 55 | | | | | 60 | | | | |

| Val | Trp | Ser | Ile | Leu | Lys | Arg | Met | Gln | Lys | Arg | Ser | Val | Thr | Ala | Leu |
| 65 | | | | | 70 | | | | | 75 | | | | | 80 |

| Met | Val | Leu | Asn | Leu | Ala | Leu | Ala | Asp | Leu | Ala | Val | Leu | Leu | Thr | Ala |
| | | | | 85 | | | | | 90 | | | | | 95 | |

| Pro | Phe | Phe | Leu | His | Phe | Leu | Ala | Gln | Gly | Thr | Trp | Ser | Phe | Gly | Leu |
| | | | 100 | | | | | 105 | | | | | 110 | | |

| Ala | Gly | Cys | Arg | Leu | Cys | His | Tyr | Val | Cys | Gly | Val | Ser | Met | Tyr | Ala |
| | | | 115 | | | | 120 | | | | | 125 | | | |

| Ser | Val | Leu | Leu | Ile | Thr | Ala | Met | Ser | Leu | Asp | Arg | Ser | Leu | Ala | Val |
| | 130 | | | | | 135 | | | | | 140 | | | | |

| Ala | Arg | Pro | Phe | Val | Ser | Gln | Lys | Leu | Arg | Thr | Lys | Ala | Met | Ala | Arg |
| 145 | | | | | 150 | | | | | 155 | | | | | 160 |

| Arg | Val | Leu | Ala | Gly | Ile | Trp | Val | Leu | Ser | Phe | Leu | Leu | Ala | Thr | Pro |
| | | | | 165 | | | | | 170 | | | | | 175 | |

| Val | Leu | Ala | Tyr | Arg | Thr | Val | Val | Pro | Trp | Lys | Thr | Asn | Met | Ser | Leu |
| | | | 180 | | | | | 185 | | | | | 190 | | |

| Cys | Phe | Pro | Arg | Tyr | Pro | Ser | Glu | Gly | His | Arg | Ala | Phe | His | Leu | Ile |
| | | 195 | | | | | 200 | | | | | 205 | | | |

| Phe | Glu | Ala | Val | Thr | Gly | Phe | Leu | Leu | Pro | Phe | Leu | Ala | Val | Val | Ala |
| | 210 | | | | | 215 | | | | | 220 | | | | |

| Ser | Tyr | Ser | Asp | Ile | Gly | Arg | Arg | Leu | Gln | Ala | Arg | Arg | Phe | Arg | Arg |
| 225 | | | | | 230 | | | | | 235 | | | | | 240 |

| Ser | Arg | Arg | Thr | Gly | Arg | Leu | Val | Val | Leu | Ile | Ile | Leu | Thr | Phe | Ala |
| | | | | 245 | | | | | 250 | | | | | 255 | |

| Ala | Phe | Trp | Leu | Pro | Tyr | His | Val | Val | Asn | Leu | Ala | Glu | Ala | Arg | Arg |
| | | | 260 | | | | | 265 | | | | | 270 | | |

| Ala | Leu | Ala | Gly | Gln | Ala | Ala | Gly | Leu | Gly | Leu | Val | Gly | Lys | Arg | Leu |
| | | 275 | | | | | 280 | | | | | 285 | | | |

| Ser | Leu | Ala | Arg | Asn | Val | Leu | Ile | Ala | Leu | Ala | Phe | Leu | Ser | Ser | Ser |
| | 290 | | | | | 295 | | | | | 300 | | | | |

| Val | Asn | Pro | Val | Leu | Tyr | Ala | Cys | Ala | Gly | Gly | Gly | Leu | Leu | Arg | Ser |
| 305 | | | | | 310 | | | | | 315 | | | | | 320 |

| Ala | Gly | Val | Gly | Phe | Val | Ala | Lys | Leu | Leu | Glu | Gly | Thr | Gly | Ser | Glu |
| | | | | 325 | | | | | 330 | | | | | 335 | |

| Ala | Ser | Ser | Thr | Arg | Arg | Gly | Gly | Ser | Leu | Gly | Gln | Thr | Ala | Arg | Ser |
| | | | 340 | | | | | 345 | | | | | 350 | | |

| Gly | Pro | Ala | Ala | Leu | Glu | Pro | Gly | Pro | Ser | Glu | Ser | Leu | Thr | Ala | Ser |
| | | 355 | | | | | 360 | | | | | 365 | | | |

| Ser | Pro | Leu | Lys | Leu | Asn | Glu | Leu | Asn |
| | 370 | | | | 375 | | | |

(2) INFORMATION FOR SEQ ID NO:43:

( i ) SEQUENCE CHARACTERISTICS:
    ( A ) LENGTH: 1901 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 701..1717

( x i ) SEQUENCE DESCRIPTION: SEQ ID NO:43:

```
GGATCCAGAA AGCCCCCAAG AGAGATGCTG AAACTCTCAG GTGGGTAAAA AGAGTAGACC        60

TCTGACGTCC CAGGGTACAG CCCTTGCTGC CATCCTGGGG GCACCCTCCT AAGTGCCAGG       120

GGCAAGCCAT GGTCAGGGGA AGCAGAAAGC GGTGACACCC CGGCCACTGC ACCTGTGGGC       180

AGGTGGGTCA GGGAGGGTCC AGGCACTCAG GATGAACAGA ACTCACCTGC CAAGGCTTGG       240

GCTGAGGAGG AGCTGGAATC CTGGAGACAC ACTGCCCCCG CCCCTCACCA CCCCTGTCAC       300

TCAGACAGCA CACCTCAGAG GCAGAACAGA AAACCCAGAG CCTCACCCAG GCAAGGCTCA       360

CGTCCCATTC CCCGCCATGG CACTGACCCG GTCCTCCCAG CTCTGAGGAG CCTCAGATCT       420

CCTGGGTGGC AGGGGTGCAG CTGCATAGCG CCGAAATTCC AAGCCCTGGT TCTGCGTTTG       480

CCTTGTGCTG AAGTTCAGAA TGCCTCTGAC GCTCACGCAC ACCAAATGGA CAAGGAGGTC       540

CCCTCAGCAG CCCCGTGGGC GGTGCTGAGC TTGAAAGTGG GAGGTTCTGA AGGCATTGGA       600

GGCCTGACTT CTGGACTTCA GAGAGCGTGA AGCTGCCTAG ATCGCAAGCT CATTGTGAAC       660

TGTTTGCTTG TTCCCTCCAG GCTCTGACTC CAGCCAAAGC ATG AAT GGC CTT GAA        715
                                              Met Asn Gly Leu Glu
                                               1               5

GTG GCT CCC CCA GGT CTG ATC ACC AAC TTC TCC CTG GCC ACG GCA GAG        763
Val Ala Pro Pro Gly Leu Ile Thr Asn Phe Ser Leu Ala Thr Ala Glu
             10                  15                  20

CAA TGT GGC CAG GAG ACG CCA CTG GAG AAC ATG CTG TTC GCC TCC TTC        811
Gln Cys Gly Gln Glu Thr Pro Leu Glu Asn Met Leu Phe Ala Ser Phe
         25                  30                  35

TAC CTT CTG GAT TTT ATC CTG GCT TTA GTT GGC AAT ACC CTG GCT CTG        859
Tyr Leu Leu Asp Phe Ile Leu Ala Leu Val Gly Asn Thr Leu Ala Leu
             40                  45                  50

TGG CTT TTC ATC CGA GAC CAC AAG TCC GGG ACC CCG GCC AAC GTG TTC        907
Trp Leu Phe Ile Arg Asp His Lys Ser Gly Thr Pro Ala Asn Val Phe
 55                  60                  65

CTG ATG CAT CTG GCC GTG GCC GAC TTG TCG TGC GTG CTG GTC CTG CCC        955
Leu Met His Leu Ala Val Ala Asp Leu Ser Cys Val Leu Val Leu Pro
 70                  75                  80                      85

ACC CGC CTG GTC TAC CAC TTC TCT GGG AAC CAC TGG CCA TTT GGG GAA       1003
Thr Arg Leu Val Tyr His Phe Ser Gly Asn His Trp Pro Phe Gly Glu
                     90                  95                 100

ATC GCA TGC CGT CTC ACC GGC TTC CTC TTC TAC CTC AAC ATG TAC GCC       1051
Ile Ala Cys Arg Leu Thr Gly Phe Leu Phe Tyr Leu Asn Met Tyr Ala
                105                 110                 115

AGC ATC TAC TTC CTC ACC TGC ATC AGC GCC GAC CGT TTC CTG GCC ATT       1099
Ser Ile Tyr Phe Leu Thr Cys Ile Ser Ala Asp Arg Phe Leu Ala Ile
            120                 125                 130

GTG CAC CCG GTC AAG TCC CTC AAG CTC CGC AGG CCC CTC TAC GCA CAC       1147
Val His Pro Val Lys Ser Leu Lys Leu Arg Arg Pro Leu Tyr Ala His
        135                 140                 145

CTG GCC TGT GCC TTC CTG TGG GTG GTG GTG GCT GTG GCC ATG GCC CCG       1195
Leu Ala Cys Ala Phe Leu Trp Val Val Val Ala Val Ala Met Ala Pro
150                 155                 160                 165
```

| | | | | | | | | | | | | | | | | |
|---|---|---|---|---|---|---|---|---|---|---|---|---|---|---|---|---|
| CTG | CTG | GTG | AGC | CCA | CAG | ACC | GTG | CAG | ACC | AAC | CAC | ACG | GTG | GTC | TGC | 1243 |
| Leu | Leu | Val | Ser | Pro | Gln | Thr | Val | Gln | Thr | Asn | His | Thr | Val | Val | Cys | |
| | | | | 170 | | | | 175 | | | | | | 180 | | |
| CTG | CAG | CTG | TAC | CGG | GAG | AAG | GCC | TCC | CAC | CAT | GCC | CTG | GTG | TCC | CTG | 1291 |
| Leu | Gln | Leu | Tyr | Arg | Glu | Lys | Ala | Ser | His | His | Ala | Leu | Val | Ser | Leu | |
| | | | 185 | | | | | 190 | | | | | 195 | | | |
| GCA | GTG | GCC | TTC | ACC | TTC | CCG | TTC | ATC | ACC | ACG | GTC | ACC | TGC | TAC | CTG | 1339 |
| Ala | Val | Ala | Phe | Thr | Phe | Pro | Phe | Ile | Thr | Thr | Val | Thr | Cys | Tyr | Leu | |
| | | 200 | | | | | 205 | | | | | 210 | | | | |
| CTG | ATC | ATC | CGC | AGC | CTG | CGG | CAG | GGC | CTG | CGT | GTG | GAG | AAG | CGC | CTC | 1387 |
| Leu | Ile | Ile | Arg | Ser | Leu | Arg | Gln | Gly | Leu | Arg | Val | Glu | Lys | Arg | Leu | |
| | 215 | | | | | 220 | | | | | 225 | | | | | |
| AAG | ACC | AAG | GCA | GTG | CGC | ATG | ATC | GCC | ATA | GTG | CTG | GCC | ATC | TTC | CTG | 1435 |
| Lys | Thr | Lys | Ala | Val | Arg | Met | Ile | Ala | Ile | Val | Leu | Ala | Ile | Phe | Leu | |
| 230 | | | | | 235 | | | | | 240 | | | | | 245 | |
| GTC | TGC | TTC | GTG | CCC | TAC | CAC | GTC | AAC | CGC | TCC | GTC | TAC | GTG | CTG | CAC | 1483 |
| Val | Cys | Phe | Val | Pro | Tyr | His | Val | Asn | Arg | Ser | Val | Tyr | Val | Leu | His | |
| | | | | 250 | | | | | 255 | | | | | 260 | | |
| TAC | CGC | AGC | CAT | GGG | GCC | TCC | TGC | GCC | ACC | CAG | CGC | ATC | CTG | GCC | CTG | 1531 |
| Tyr | Arg | Ser | His | Gly | Ala | Ser | Cys | Ala | Thr | Gln | Arg | Ile | Leu | Ala | Leu | |
| | | | 265 | | | | | 270 | | | | | 275 | | | |
| GCA | AAC | CGC | ATC | ACC | TCC | TGC | CTC | ACC | AGC | CTC | AAC | GGG | GCA | CTC | GAC | 1579 |
| Ala | Asn | Arg | Ile | Thr | Ser | Cys | Leu | Thr | Ser | Leu | Asn | Gly | Ala | Leu | Asp | |
| | | 280 | | | | | 285 | | | | | 290 | | | | |
| CCC | ATC | ATG | TAT | TTC | TTC | GTG | GCT | GAG | AAG | TTC | CGC | CAC | GCC | CTG | TGC | 1627 |
| Pro | Ile | Met | Tyr | Phe | Phe | Val | Ala | Glu | Lys | Phe | Arg | His | Ala | Leu | Cys | |
| | 295 | | | | | 300 | | | | | 305 | | | | | |
| AAC | TTG | CTC | TGT | GGC | AAA | AGG | CTC | AAG | GGC | CCG | CCC | CCC | AGC | TTC | GAA | 1675 |
| Asn | Leu | Leu | Cys | Gly | Lys | Arg | Leu | Lys | Gly | Pro | Pro | Pro | Ser | Phe | Glu | |
| 310 | | | | | 315 | | | | | 320 | | | | | 325 | |
| GGG | AAA | ACC | AAC | GAG | AGC | TCG | CTG | AGT | GCC | AAG | TCA | GAG | CTG | | | 1717 |
| Gly | Lys | Thr | Asn | Glu | Ser | Ser | Leu | Ser | Ala | Lys | Ser | Glu | Leu | | | |
| | | | | 330 | | | | | 335 | | | | | | | |

```
TGAGCGGGGG GCGCCGTCCA GCGCGAGCGC AGACTGTTTA GGACTCAGCA GACCCAGCAA    1777

GAGGCATCTG CCCTTTCCCC AGCCACCTCC CCGGCAAGCA ACCTGAAATC TCAGCAGATG    1837

CCCACCATTT CTCTAGATCG CCTAGTCTCA ACCCATAAAA AGGAAGAACT GACAAAGGGG    1897

ATCC                                                                  1901
```

( 2 ) INFORMATION FOR SEQ ID NO:44:

( i ) SEQUENCE CHARACTERISTICS:
        ( A ) LENGTH: 339 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| | | | | | | | | | | | | | | |
|---|---|---|---|---|---|---|---|---|---|---|---|---|---|---|
| Met | Asn | Gly | Leu | Glu | Val | Ala | Pro | Pro | Gly | Leu | Ile | Thr | Asn | Phe | Ser |
| 1 | | | | 5 | | | | | 10 | | | | | 15 | |
| Leu | Ala | Thr | Ala | Glu | Gln | Cys | Gly | Gln | Glu | Thr | Pro | Leu | Glu | Asn | Met |
| | | | 20 | | | | | 25 | | | | | 30 | | |
| Leu | Phe | Ala | Ser | Phe | Tyr | Leu | Leu | Asp | Phe | Ile | Leu | Ala | Leu | Val | Gly |
| | | 35 | | | | | 40 | | | | | 45 | | | |
| Asn | Thr | Leu | Ala | Leu | Trp | Leu | Phe | Ile | Arg | Asp | His | Lys | Ser | Gly | Thr |
| | 50 | | | | | 55 | | | | | 60 | | | | |
| Pro | Ala | Asn | Val | Phe | Leu | Met | His | Leu | Ala | Val | Ala | Asp | Leu | Ser | Cys |
| 65 | | | | | 70 | | | | | 75 | | | | | 80 |

|     |     |     |     |     |     |     |     |     |     |     |     |     |     |     |     |
|-----|-----|-----|-----|-----|-----|-----|-----|-----|-----|-----|-----|-----|-----|-----|-----|
| Val | Leu | Val | Leu | Pro 85 | Thr | Arg | Leu | Val | Tyr 90 | His | Phe | Ser | Gly | Asn 95 | His |
| Trp | Pro | Phe | Gly 100 | Glu | Ile | Ala | Cys | Arg 105 | Leu | Thr | Gly | Phe | Leu 110 | Phe | Tyr |
| Leu | Asn | Met 115 | Tyr | Ala | Ser | Ile | Tyr 120 | Phe | Leu | Thr | Cys | Ile 125 | Ser | Ala | Asp |
| Arg | Phe 130 | Leu | Ala | Ile | Val | His 135 | Pro | Val | Lys | Ser | Leu 140 | Lys | Leu | Arg | Arg |
| Pro 145 | Leu | Tyr | Ala | His | Leu 150 | Ala | Cys | Ala | Phe | Leu 155 | Trp | Val | Val | Val | Ala 160 |
| Val | Ala | Met | Ala | Pro 165 | Leu | Leu | Val | Ser | Pro 170 | Gln | Thr | Val | Gln | Thr 175 | Asn |
| His | Thr | Val | Val 180 | Cys | Leu | Gln | Leu | Tyr 185 | Arg | Glu | Lys | Ala | Ser 190 | His | His |
| Ala | Leu | Val 195 | Ser | Leu | Ala | Val | Ala 200 | Phe | Thr | Phe | Pro | Phe 205 | Ile | Thr | Thr |
| Val | Thr 210 | Cys | Tyr | Leu | Leu | Ile 215 | Ile | Arg | Ser | Leu | Arg 220 | Gln | Gly | Leu | Arg |
| Val 225 | Glu | Lys | Arg | Leu | Lys 230 | Thr | Lys | Ala | Val | Arg 235 | Met | Ile | Ala | Ile | Val 240 |
| Leu | Ala | Ile | Phe | Leu 245 | Val | Cys | Phe | Val | Pro 250 | Tyr | His | Val | Asn | Arg 255 | Ser |
| Val | Tyr | Val | Leu 260 | His | Tyr | Arg | Ser | His 265 | Gly | Ala | Ser | Cys | Ala 270 | Thr | Gln |
| Arg | Ile | Leu 275 | Ala | Leu | Ala | Asn | Arg 280 | Ile | Thr | Ser | Cys | Leu 285 | Thr | Ser | Leu |
| Asn | Gly 290 | Ala | Leu | Asp | Pro | Ile 295 | Met | Tyr | Phe | Phe | Val 300 | Ala | Glu | Lys | Phe |
| Arg 305 | His | Ala | Leu | Cys | Asn 310 | Leu | Leu | Cys | Gly | Lys 315 | Arg | Leu | Lys | Gly | Pro 320 |
| Pro | Pro | Ser | Phe | Glu 325 | Gly | Lys | Thr | Asn | Glu 330 | Ser | Ser | Leu | Ser | Ala 335 | Lys |
| Ser | Glu | Leu |     |     |     |     |     |     |     |     |     |     |     |     |     |

( 2 ) INFORMATION FOR SEQ ID NO:45:

( i ) SEQUENCE CHARACTERISTICS:
        ( A ) LENGTH: 1317 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 201..1211

( x i ) SEQUENCE DESCRIPTION: SEQ ID NO:45:

```
GAGTTGTAGG  ATTCTACATT  AATTCTCTTG  TGCCCTTAGC  CCACTACTTC  AGAATTTCCT        60

GAAGAAAGCA  AGCCTGAATT  GGTTTTTTAA  ATTGCTTTAA  AAATTTTTTT  TAACTGGGTT       120

AATGCTTGCT  GAATTGGAAG  TGAATGTCCA  TTCCTTTGCC  TCTTTTGCAG  ATATACACTT       180

CAGATAACTA  CACCGAGGAA  ATG  GGC  TCA  GGG  GAC  TAT  GAC  TCC  ATG  AAG       230
                       Met  Gly  Ser  Gly  Asp  Tyr  Asp  Ser  Met  Lys
                         1                5                         10

GAA  CCC  TGT  TTC  CGT  GAA  GAA  AAT  GCT  AAT  TTC  AAT  AAA  ATC  TTC  CTG   278
Glu  Pro  Cys  Phe  Arg  Glu  Glu  Asn  Ala  Asn  Phe  Asn  Lys  Ile  Phe  Leu
              15                         20                         25
```

| | | | | | | | | | | | | | | | | |
|---|---|---|---|---|---|---|---|---|---|---|---|---|---|---|---|---|
| CCC | ACC | ATC | TAC | TCC | ATC | ATC | TTC | TTA | ACT | GGC | ATT | GTG | GGC | AAT | GGA | 326 |
| Pro | Thr | Ile | Tyr | Ser | Ile | Ile | Phe | Leu | Thr | Gly | Ile | Val | Gly | Asn | Gly | |
| | | | 30 | | | | 35 | | | | | 40 | | | | |
| TTG | GTC | ATC | CTG | GTC | ATG | GGT | TAC | CAG | AAG | AAA | CTG | AGA | AGC | ATG | ACG | 374 |
| Leu | Val | Ile | Leu | Val | Met | Gly | Tyr | Gln | Lys | Lys | Leu | Arg | Ser | Met | Thr | |
| | | 45 | | | | | 50 | | | | | 55 | | | | |
| GAC | AAG | TAC | AGG | CTG | CAC | CTG | TCA | GTG | GCC | GAC | CTC | CTC | TTT | GTC | ATC | 422 |
| Asp | Lys | Tyr | Arg | Leu | His | Leu | Ser | Val | Ala | Asp | Leu | Leu | Phe | Val | Ile | |
| | 60 | | | | 65 | | | | | 70 | | | | | | |
| ACG | CTT | CCC | TTC | TGG | GCA | GTT | GAT | GCC | GTG | GCA | AAC | TGG | TAC | TTT | GGG | 470 |
| Thr | Leu | Pro | Phe | Trp | Ala | Val | Asp | Ala | Val | Ala | Asn | Trp | Tyr | Phe | Gly | |
| 75 | | | | | 80 | | | | | 85 | | | | | 90 | |
| AAC | TTC | CTA | TGC | AAG | GCA | GTC | CAT | GTC | ATC | TAC | ACA | GTC | AAC | CTC | TAC | 518 |
| Asn | Phe | Leu | Cys | Lys | Ala | Val | His | Val | Ile | Tyr | Thr | Val | Asn | Leu | Tyr | |
| | | | | 95 | | | | | 100 | | | | | 105 | | |
| AGC | AGT | GTC | CTC | ATC | CTG | GCC | TTC | ATC | AGT | CTG | GAC | CGC | TAC | CTG | GCC | 566 |
| Ser | Ser | Val | Leu | Ile | Leu | Ala | Phe | Ile | Ser | Leu | Asp | Arg | Tyr | Leu | Ala | |
| | | | 110 | | | | | 115 | | | | | 120 | | | |
| ATC | GTC | CAC | GCC | ACC | AAC | AGT | CAG | AGG | CCA | AGG | AAG | CTG | TTG | GCT | GAA | 614 |
| Ile | Val | His | Ala | Thr | Asn | Ser | Gln | Arg | Pro | Arg | Lys | Leu | Leu | Ala | Glu | |
| | | 125 | | | | | 130 | | | | | 135 | | | | |
| AAG | GTG | GTC | TAT | GTT | GGC | GTC | TGG | ATC | CCT | GCC | CTC | CTG | CTG | ACT | ATT | 662 |
| Lys | Val | Val | Tyr | Val | Gly | Val | Trp | Ile | Pro | Ala | Leu | Leu | Leu | Thr | Ile | |
| | 140 | | | | | 145 | | | | | 150 | | | | | |
| CCC | GAC | TTC | ATC | TTT | GCC | AAC | GTC | AGT | GAG | GCA | GAT | GAC | AGA | TAT | ATC | 710 |
| Pro | Asp | Phe | Ile | Phe | Ala | Asn | Val | Ser | Glu | Ala | Asp | Asp | Arg | Tyr | Ile | |
| 155 | | | | | 160 | | | | | 165 | | | | | 170 | |
| TGT | GAC | CGC | TTC | TAC | CCC | AAT | GAC | TTG | TGG | GTG | GTT | GTG | TTC | CAG | TTT | 758 |
| Cys | Asp | Arg | Phe | Tyr | Pro | Asn | Asp | Leu | Trp | Val | Val | Val | Phe | Gln | Phe | |
| | | | | 175 | | | | | 180 | | | | | 185 | | |
| CAG | CAC | ATC | ATG | GTT | GGC | CTT | ATC | CTG | CCT | GGT | ATT | GTC | ATC | CTG | TCC | 806 |
| Gln | His | Ile | Met | Val | Gly | Leu | Ile | Leu | Pro | Gly | Ile | Val | Ile | Leu | Ser | |
| | | | 190 | | | | | 195 | | | | | 200 | | | |
| TGC | TAT | TGC | ATT | ATC | ATC | TCC | AAG | CTG | TCA | CAC | TCC | AAG | GGC | CAC | CAG | 854 |
| Cys | Tyr | Cys | Ile | Ile | Ile | Ser | Lys | Leu | Ser | His | Ser | Lys | Gly | His | Gln | |
| | | 205 | | | | | 210 | | | | | 215 | | | | |
| AAG | CGC | AAG | GCC | CTC | AAG | ACC | ACA | GTC | ATC | CTC | ATC | CTG | GCT | TTC | TTC | 902 |
| Lys | Arg | Lys | Ala | Leu | Lys | Thr | Thr | Val | Ile | Leu | Ile | Leu | Ala | Phe | Phe | |
| | 220 | | | | | 225 | | | | | 230 | | | | | |
| GCC | TGT | TGG | CTG | CCT | TAC | TAC | ATT | GGG | ATC | AGC | ATC | GAC | TCC | TTC | ATC | 950 |
| Ala | Cys | Trp | Leu | Pro | Tyr | Tyr | Ile | Gly | Ile | Ser | Ile | Asp | Ser | Phe | Ile | |
| 235 | | | | | 240 | | | | | 245 | | | | | 250 | |
| CTC | CTG | GAA | ATC | ATC | AAG | CAA | GGG | TGT | GAG | TTT | GAG | AAC | ACT | GTG | CAC | 998 |
| Leu | Leu | Glu | Ile | Ile | Lys | Gln | Gly | Cys | Glu | Phe | Glu | Asn | Thr | Val | His | |
| | | | | 255 | | | | | 260 | | | | | 265 | | |
| AAG | TGG | ATT | TCC | ATC | ACC | GAG | GCC | CTA | GCT | TTC | TTC | CAC | TGT | TGT | CTG | 1046 |
| Lys | Trp | Ile | Ser | Ile | Thr | Glu | Ala | Leu | Ala | Phe | Phe | His | Cys | Cys | Leu | |
| | | | 270 | | | | | 275 | | | | | 280 | | | |
| AAC | CCC | ATC | CTC | TAT | GCT | TTC | CTT | GGA | GCC | AAA | TTT | AAA | ACC | TCT | GCC | 1094 |
| Asn | Pro | Ile | Leu | Tyr | Ala | Phe | Leu | Gly | Ala | Lys | Phe | Lys | Thr | Ser | Ala | |
| | | 285 | | | | | 290 | | | | | 295 | | | | |
| CAG | CAC | GCA | CTC | ACC | TCT | GTG | AGC | AGA | GGG | TCC | AGC | CTC | AAG | ATC | CTC | 1142 |
| Gln | His | Ala | Leu | Thr | Ser | Val | Ser | Arg | Gly | Ser | Ser | Leu | Lys | Ile | Leu | |
| | 300 | | | | | 305 | | | | | 310 | | | | | |
| TCC | AAA | GGA | AAG | CGA | GGT | GGA | CAT | TCA | TCT | GTT | TCC | ACT | GAG | TCT | GAG | 1190 |
| Ser | Lys | Gly | Lys | Arg | Gly | Gly | His | Ser | Ser | Val | Ser | Thr | Glu | Ser | Glu | |
| 315 | | | | | 320 | | | | | 325 | | | | | 330 | |
| TCT | TCA | AGT | TTT | CAC | TCC | AGC | TAACACAGAT | GTAAAAGACT | TTTTTATAC | | | | | | | 1241 |
| Ser | Ser | Ser | Phe | His | Ser | Ser | | | | | | | | | | |
| | | | | 335 | | | | | | | | | | | | |

```
GATAAATAAC CTTTTTTTAA GTTACACATT TTTCAGATAT AAAAGACTGA CCAATATTGA      1301

AAAAAAAAAA AAAAA                                                      1317
```

( 2 ) INFORMATION FOR SEQ ID NO:46:

( i ) SEQUENCE CHARACTERISTICS:
    ( A ) LENGTH: 337 amino acids
    ( B ) TYPE: amino acid
    ( D ) TOPOLOGY: linear ( i i ) MOLECULE TYPE: protein ( x i ) SEQUENCE DESCRIPTION: SEQ ID NO:46:

| Met | Gly | Ser | Gly | Asp | Tyr | Asp | Ser | Met | Lys | Glu | Pro | Cys | Phe | Arg | Glu |
|---|---|---|---|---|---|---|---|---|---|---|---|---|---|---|---|
| 1 | | | | 5 | | | | | 10 | | | | | 15 | |

| Glu | Asn | Ala | Asn | Phe | Asn | Lys | Ile | Phe | Leu | Pro | Thr | Ile | Tyr | Ser | Ile |
|---|---|---|---|---|---|---|---|---|---|---|---|---|---|---|---|
| | | | 20 | | | | | 25 | | | | | 30 | | |

| Ile | Phe | Leu | Thr | Gly | Ile | Val | Gly | Asn | Gly | Leu | Val | Ile | Leu | Val | Met |
|---|---|---|---|---|---|---|---|---|---|---|---|---|---|---|---|
| | | | 35 | | | | 40 | | | | | 45 | | | |

| Gly | Tyr | Gln | Lys | Lys | Leu | Arg | Ser | Met | Thr | Asp | Lys | Tyr | Arg | Leu | His |
|---|---|---|---|---|---|---|---|---|---|---|---|---|---|---|---|
| | 50 | | | | | 55 | | | | | 60 | | | | |

| Leu | Ser | Val | Ala | Asp | Leu | Leu | Phe | Val | Ile | Thr | Leu | Pro | Phe | Trp | Ala |
|---|---|---|---|---|---|---|---|---|---|---|---|---|---|---|---|
| 65 | | | | | 70 | | | | | 75 | | | | | 80 |

| Val | Asp | Ala | Val | Ala | Asn | Trp | Tyr | Phe | Gly | Asn | Phe | Leu | Cys | Lys | Ala |
|---|---|---|---|---|---|---|---|---|---|---|---|---|---|---|---|
| | | | | 85 | | | | | 90 | | | | | 95 | |

| Val | His | Val | Ile | Tyr | Thr | Val | Asn | Leu | Tyr | Ser | Ser | Val | Leu | Ile | Leu |
|---|---|---|---|---|---|---|---|---|---|---|---|---|---|---|---|
| | | | 100 | | | | | 105 | | | | | 110 | | |

| Ala | Phe | Ile | Ser | Leu | Asp | Arg | Tyr | Leu | Ala | Ile | Val | His | Ala | Thr | Asn |
|---|---|---|---|---|---|---|---|---|---|---|---|---|---|---|---|
| | | 115 | | | | | 120 | | | | | 125 | | | |

| Ser | Gln | Arg | Pro | Arg | Lys | Leu | Leu | Ala | Glu | Lys | Val | Val | Tyr | Val | Gly |
|---|---|---|---|---|---|---|---|---|---|---|---|---|---|---|---|
| | 130 | | | | | 135 | | | | | 140 | | | | |

| Val | Trp | Ile | Pro | Ala | Leu | Leu | Leu | Thr | Ile | Pro | Asp | Phe | Ile | Phe | Ala |
|---|---|---|---|---|---|---|---|---|---|---|---|---|---|---|---|
| 145 | | | | | 150 | | | | | 155 | | | | | 160 |

| Asn | Val | Ser | Glu | Ala | Asp | Asp | Arg | Tyr | Ile | Cys | Asp | Arg | Phe | Tyr | Pro |
|---|---|---|---|---|---|---|---|---|---|---|---|---|---|---|---|
| | | | | 165 | | | | | 170 | | | | | 175 | |

| Asn | Asp | Leu | Trp | Val | Val | Val | Phe | Gln | Phe | Gln | His | Ile | Met | Val | Gly |
|---|---|---|---|---|---|---|---|---|---|---|---|---|---|---|---|
| | | | 180 | | | | | 185 | | | | | 190 | | |

| Leu | Ile | Leu | Pro | Gly | Ile | Val | Ile | Leu | Ser | Cys | Tyr | Cys | Ile | Ile | Ile |
|---|---|---|---|---|---|---|---|---|---|---|---|---|---|---|---|
| | | 195 | | | | | 200 | | | | | 205 | | | |

| Ser | Lys | Leu | Ser | His | Ser | Lys | Gly | His | Gln | Lys | Arg | Lys | Ala | Leu | Lys |
|---|---|---|---|---|---|---|---|---|---|---|---|---|---|---|---|
| | 210 | | | | | 215 | | | | | 220 | | | | |

| Thr | Thr | Val | Ile | Leu | Ile | Leu | Ala | Phe | Phe | Ala | Cys | Trp | Leu | Pro | Tyr |
|---|---|---|---|---|---|---|---|---|---|---|---|---|---|---|---|
| 225 | | | | | 230 | | | | | 235 | | | | | 240 |

| Tyr | Ile | Gly | Ile | Ser | Ile | Asp | Ser | Phe | Ile | Leu | Leu | Glu | Ile | Ile | Lys |
|---|---|---|---|---|---|---|---|---|---|---|---|---|---|---|---|
| | | | | 245 | | | | | 250 | | | | | 255 | |

| Gln | Gly | Cys | Glu | Phe | Glu | Asn | Thr | Val | His | Lys | Trp | Ile | Ser | Ile | Thr |
|---|---|---|---|---|---|---|---|---|---|---|---|---|---|---|---|
| | | | 260 | | | | | 265 | | | | | 270 | | |

| Glu | Ala | Leu | Ala | Phe | Phe | His | Cys | Cys | Leu | Asn | Pro | Ile | Leu | Tyr | Ala |
|---|---|---|---|---|---|---|---|---|---|---|---|---|---|---|---|
| | | 275 | | | | | 280 | | | | | 285 | | | |

| Phe | Leu | Gly | Ala | Lys | Phe | Lys | Thr | Ser | Ala | Gln | His | Ala | Leu | Thr | Ser |
|---|---|---|---|---|---|---|---|---|---|---|---|---|---|---|---|
| | 290 | | | | | 295 | | | | | 300 | | | | |

| Val | Ser | Arg | Gly | Ser | Ser | Leu | Lys | Ile | Leu | Ser | Lys | Gly | Lys | Arg | Gly |
|---|---|---|---|---|---|---|---|---|---|---|---|---|---|---|---|
| 305 | | | | | 310 | | | | | 315 | | | | | 320 |

| Gly | His | Ser | Ser | Val | Ser | Thr | Glu | Ser | Glu | Ser | Ser | Ser | Phe | His | Ser |
|---|---|---|---|---|---|---|---|---|---|---|---|---|---|---|---|
| | | | | 325 | | | | | 330 | | | | | 335 | |

Ser (2) INFORMATION FOR SEQ ID NO:47:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GTTGGATCCA TGATTGCACC ACTGCA     26

(2) INFORMATION FOR SEQ ID NO:48:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

CGCGCTGTAG GCCCAGGCTT TAAAGTTCC     29

(2) INFORMATION FOR SEQ ID NO:49:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

TTTAAAGCCT GGGCCTACAG CGCGGCCAA     29

(2) INFORMATION FOR SEQ ID NO:50:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

GTCACTGTAC AGGAGCTTGC AAAAGTGGA     29

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

TTTTGCAAGC TCCTGTACAG TGACCTCCAG     30

(2) INFORMATION FOR SEQ ID NO:52:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:52:

CTGGGCCAGG ACGATAAAGG CCTCCACATG  30

( 2 ) INFORMATION FOR SEQ ID NO:53:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:53:

GAGGCCTTTA TCGTCCTGGC CCAGACGGT  29

( 2 ) INFORMATION FOR SEQ ID NO:54:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:54:

TCAGAATTCA GGTGACGTCG TAGGCGA  27

( 2 ) INFORMATION FOR SEQ ID NO:55:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:55:

ACTGAATTCT ATGGGGAGAA GGTGG  25

( 2 ) INFORMATION FOR SEQ ID NO:56:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:56:

GGTGAATTCA GGCTTTAAAG TTCCGCAC  28

( 2 ) INFORMATION FOR SEQ ID NO:57:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear (  i  i  ) MOLECULE TYPE: DNA (  x  i  ) SEQUENCE DESCRIPTION: SEQ ID NO:57:

CTGGATCCAT GGAGGAAGGT GGT    23

( 2 ) INFORMATION FOR SEQ ID NO:58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

ATAGTCCCGG TACGTGGCCC CCGAGGATTT    30

( 2 ) INFORMATION FOR SEQ ID NO:59:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

AAATCCTCGG GGGCCACGTA CCGGGACTAT    30

( 2 ) INFORMATION FOR SEQ ID NO:60:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

CCCGGTGGTG CGTAAGAGGT AGCTGCTGAG CT    32

( 2 ) INFORMATION FOR SEQ ID NO:61:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

CTCAGCAGCT ACCTCTTACG CACCACCGGG GAC    33

( 2 ) INFORMATION FOR SEQ ID NO:62:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:62:

```
GTACAGCGTC TTCACAAGCC CACGGTGGTG G                                          31
```

( 2 ) INFORMATION FOR SEQ ID NO:63:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

```
ACCACCGTGG GCTTTGTGAA AGACGCTGTA CAT                                        33
```

( 2 ) INFORMATION FOR SEQ ID NO:64:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

```
AGGAATTCTA GAAGAGGTCA AAGTCACA                                              28
```